United States Patent
Ma et al.

(10) Patent No.: US 12,257,298 B2
(45) Date of Patent: Mar. 25, 2025

(54) CORONAVIRUS VACCINE

(71) Applicant: ACADEMIA SINICA, Taipei (TW)

(72) Inventors: Che Ma, New Taipei (TW); Chi-Huey Wong, Taipei (TW); Han-Yi Huang, Taoyuan (TW)

(73) Assignee: ACADEMIA SINICA, Taipei (TW)

( * ) Notice: Subject to any disclaimer, the term of this patent is extended or adjusted under 35 U.S.C. 154(b) by 57 days.

(21) Appl. No.: 18/005,573

(22) PCT Filed: Apr. 12, 2022

(86) PCT No.: PCT/US2022/071682
§ 371 (c)(1),
(2) Date: Jan. 13, 2023

(87) PCT Pub. No.: WO2022/221837
PCT Pub. Date: Oct. 20, 2022

(65) Prior Publication Data
US 2024/0016917 A1 Jan. 18, 2024

Related U.S. Application Data

(60) Provisional application No. 63/190,199, filed on May 18, 2021, provisional application No. 63/173,752, filed on Apr. 12, 2021.

(51) Int. Cl.
*A61K 39/215* (2006.01)
*A61P 31/04* (2006.01)
*A61K 39/00* (2006.01)

(52) U.S. Cl.
CPC ............ *A61K 39/215* (2013.01); *A61P 31/04* (2018.01); *A61K 2039/55505* (2013.01); *A61K 2039/575* (2013.01)

(58) Field of Classification Search
None
See application file for complete search history.

(56) References Cited

U.S. PATENT DOCUMENTS

| | | | |
|---|---|---|---|
| 7,871,626 B2 | 1/2011 | Hoffmann et al. | |
| 7,981,428 B2 | 7/2011 | Wong | |
| 10,301,377 B2 | 5/2019 | Graham et al. | |
| 10,906,944 B2 | 2/2021 | He et al. | |
| 10,953,089 B1 | 3/2021 | Smith et al. | |
| 10,954,289 B1 | 3/2021 | Babb et al. | |
| 11,480,391 B2 | 10/2022 | Wong et al. | |
| 11,866,485 B2 | 1/2024 | Lin et al. | |
| 11,918,641 B2 | 3/2024 | Wong | |
| 2010/0041740 A1 | 2/2010 | Wong et al. | |
| 2010/0247571 A1* | 9/2010 | Wong ................ | C07K 16/1018 435/68.1 |
| 2015/0132330 A1 | 5/2015 | Garcia-Sastre et al. | |
| 2016/0199481 A1 | 7/2016 | Bloom | |
| 2016/0376321 A1 | 12/2016 | Hotez et al. | |
| 2018/0043007 A1 | 2/2018 | LeFebvre et al. | |
| 2020/0046826 A1 | 2/2020 | Wong et al. | |
| 2021/0017563 A1 | 1/2021 | Bhatnagar et al. | |
| 2023/0000741 A1 | 3/2023 | Wong et al. | |
| 2023/0074185 A1 | 3/2023 | Wong | |
| 2023/0105209 A1 | 4/2023 | Lin | |
| 2023/0002790 A1 | 9/2023 | Lin et al. | |
| 2023/0279080 A1 | 9/2023 | Lin | |
| 2023/0302114 A1 | 9/2023 | Wong | |
| 2024/0016917 A1 | 1/2024 | Ma et al. | |
| 2024/0066113 A1 | 2/2024 | Wong et al. | |
| 2024/0100147 A1 | 3/2024 | Wong et al. | |

FOREIGN PATENT DOCUMENTS

| | | |
|---|---|---|
| CN | 105934441 A | 9/2016 |
| CN | 112626124 A | 4/2021 |
| EP | 1987068 A1 | 11/2008 |
| EP | 2949665 A1 | 12/2015 |
| JP | 2017518989 A | 7/2017 |
| RU | 2720614 C1 | 5/2020 |
| RU | 2730897 C1 | 8/2020 |
| WO | 2004099240 A2 | 11/2004 |
| WO | 2004099240 A3 | 11/2004 |
| WO | 2007008918 A2 | 1/2007 |
| WO | 2007095506 A1 | 8/2007 |
| WO | 2009002516 A1 | 12/2008 |
| WO | 2009007427 A2 | 1/2009 |

(Continued)

OTHER PUBLICATIONS

Yang, et al. Inhibition of SARS-CoV-2 viral entry upon blocking N- and O-glycan elaboration. Elife. Oct. 26, 2020;9:e61552. doi: 10.7554/eLife.61552. PMID: 33103998. (Year: 2020).*
NCBI Reference Sequence: YP_009724390.1 (Jan. 13, 2020). (Year: 2020).*
Watanabe Y, Allen JD, Wrapp D, McLellan JS, Crispin M. Site-specific glycan analysis of the SARS-CoV-2 spike. Science. Jul. 17, 2020;369(6501):330-333. doi: 10.1126/science.abb9983. Epub May 4, 2020. PMID

(56) References Cited

FOREIGN PATENT DOCUMENTS

| | | | |
|---|---|---|---|
| WO | 2010022737 | A1 | 3/2010 |
| WO | 2010111687 | A2 | 9/2010 |
| WO | 2010148511 | A1 | 12/2010 |
| WO | 2012054907 | A2 | 4/2012 |
| WO | 2012088428 | A1 | 6/2012 |
| WO | 2013043729 | A1 | 3/2013 |
| WO | 2013067652 | A1 | 5/2013 |
| WO | 2014115797 | A1 | 7/2014 |
| WO | 2015057942 | A1 | 4/2015 |
| WO | 2015073727 | A1 | 5/2015 |
| WO | 2015184004 | A1 | 12/2015 |
| WO | 2017062496 | A2 | 4/2017 |
| WO | WO2017081082 | A2 | 5/2017 |
| WO | 2018089407 | | 11/2017 |
| WO | 2019028190 | A1 | 2/2019 |
| WO | 2015028478 | A1 | 6/2019 |
| WO | 2019246363 | A1 | 12/2019 |
| WO | 2020011275 | A1 | 1/2020 |
| WO | WO2020205034 | A1 | 3/2020 |
| WO | 2019246363 | | 4/2020 |
| WO | 2020172072 | A1 | 8/2020 |
| WO | 2020198865 | A1 | 10/2020 |
| WO | 2021019102 | A2 | 2/2021 |
| WO | 2021035325 | A1 | 3/2021 |
| WO | 2021045836 | A1 | 3/2021 |
| WO | 2021174128 | A1 | 9/2021 |
| WO | 2021180602 | A1 | 9/2021 |
| WO | 2021183195 | A1 | 9/2021 |
| WO | 2021219897 | A1 | 11/2021 |
| WO | 2021226533 | A1 | 11/2021 |
| WO | 2022221835 | | 4/2022 |
| WO | 2022221835 | A2 | 10/2022 |
| WO | 2022221837 | A2 | 10/2022 |
| WO | 2023056482 | | 10/2022 |
| WO | 2023129928 | | 12/2022 |
| WO | 2023056482 | A1 | 4/2023 |
| WO | 2023129928 | A2 | 7/2023 |

OTHER PUBLICATIONS

GenBank Accession: QHD43416.1, (Mar. 18, 2020) [Described in the Office Action as Appendix A] (Year: 2020).*

Cao, Yiwei et al., "Dynamic Interactions of Fully Glycosylated SARS-CoV-2 Spike Protein with Various Antibodies," JCTC, Sep. 16, 2021, vol. 17, pp. 6559-6569.

Castrucci, M.R. et al., "Biologic importance of neuramindase stalk length in influenza A virus", Journal of Virology, 1993, vol. 67, No. 2, pp. 759-764.

Chokhawala, H.A. et al., "Enzymatic Synthesis of Fluorinated Mechanistic Proves for Sialidases and Sialyltransferases", J.Am. Chem. Soc., 2007, p. 10630; scheme 1.

Dowling, W. et al., "Influences of Glycosylation on Antigenicity, Immunogenicity, and Protective Efficacy of Ebola Virus GP DNA Vaccines", J. of Virology, 2007, vol. 81, No. 4, pp. 1821-1837, p. 1822, second column, fourth paragraph; p. 1823, second column, third paragraph; doi:10.1128/JVI.02098-06.

Feng et al., "A Glycolipid Adjuvant, 7DW8-5, Enhances the Protective Immune Response to the Current Slpit Influenza Vaccine in Mice", Frontiers in Microbiology, Sep. 18, 2019, vol. 10, No. 2157M, pp. 1-9; abstract.

Galili, "Amplifying immunogenicity of prospective Covid-19 vaccines by glycoengineering the coronavirus glycan-shield to present alpha-gal epitopes", Vaccine, Aug. 19, 2020; abstract; Fig. 1; DOI: 10.1016/j.vaccine.2020.08032.

GenBank Accession CCH23214, haemagglutinin [Influenza A virus (A/WSN/1933(H1N1))], 2013.

GenBank Accession, ACF54601, neuraminidase [Influenza A virus (A/WSN/1933(H1N1))], 2008.

Gillian, M. Air, "Influenza neuraminidase", Influenza and Other Respiratory Viruses, 2011.

Hayashi, T. et al., "Stereospecific α-Sialylation by Site-Selective Fluorination", Agnew. Chem. Int. Ed., Jan. 25, 2019, vol. 58, pp. 3814-3818. (Whole Document).

Hughes et al., "Adaptation of Influenza A Viruses to Cells Expressing Low Levels of Sialic Acid Leads to Loss of Neuraminidase Activity", Journal of Virology, 2001, vol. 75, No. 8, pp. 3766-3770.

Li, et al., Glycosylation of Neuraminidase Determines the Neurovirulence of Influenza A/WSN/33 Virus, 1993, Journal of Virology, vol. 67, No. 11, pp. 6667-6673.

Liu, Wen-Chun et al., "Unmasking Stem-Specific Neutralizing Epitopes by Abolishing N-Linked Glycosylation Sites of Influenza Virus Hemagglutinin Proteins for Vaccine Design", Journal of Virology, vol. 90 No. 19, Oct. 2016.

Lo, H.-J. et al., "Synthesis of Sialidase-Resistant Oligosaccharide and Antibody Glycoform Containing α2,6-Linked 3Fax—Neu5Ac", J. Am. Chem. Soc., Apr. 10, 2019, vol. 141, No. 16, pp. 6484-6488. (Whole Document.).

Medina, Rafael A. et al., "Glycosylations in the globular head of the hemagglutinin protein modulate the virulence and antigenic properties of the H1N1 influenza viruses", Sci Transl Med., May 29, 2013.

Nobusawa et al., "Comparison of Complete Amino Acid Sequences and Receptor-Binding Properties among 13 Serotypes of Hemagglutinins of Influenza A Viruses", Virology, 182, 475-485 (1991).

Okamoto, K. et al., "An effective synthesis of α-glycosides of N-acetylneuraminic acid by use of 2β-halo-3β-hydroxy-4,7,8,9-tetra-O-acetyl-N-acetylneuraminic acid methyl ester", Tetrahedron Letters, 1986, vol. 27, No. 43, pp. 5233-5236.

Rahman, M Shaminur et al., "Epitope-based chimeric peptide vaccine design against S, M, and E proteins of SARS-CoV-2, the etiologic agent of COVID-19 pandemic, an in silico approach", PeerJ, Jul. 27, 2020 (publication date), DOI 10.7717/peerj.9572, Internal pp. 1-30, Supplemental Information pp. 1, 2. Abstract; and supplemental information pp. 1, 2.

Roberts, Paul C. et al., "Role of Conserved Glycosylation Sites in Maturation and Transport of Influenza A Virus Hemagglutinin", Journal of Virology, Jun. 1993, p. 3048-3060.

Sun et al., "N-Linked Glycosylation of the Hemagglutinin Protein Influences Virulence and Antigenicity of the 1918 Pandemic and Seasonal H1N1 Influenza A Viruses", 2013, Journal of Virology, vol. 87, No. 15, pp. 8756-8766.

Wu, Chung-Yi et al., "Influenza A surface glycosylation and vaccine design", PNAS, Jan. 2017, (Epub Dec. 27, 2016), vol. 114, No. 2, pp. 280-285.

Yang, Zhiwei et al., "Mutation effects of neuraminidases and their docking with ligands: a molecular dynamics and free energy calculation study", J Comput Aided Mol Des, 27: 935-950, 2013.

Zaraket, Hassan et al., "Full Genome Characterization of Human Influenza A/H3N2 Isolates from Asian Countries Reveals a Rare Amantadine Resistance-Conferring Mutation and Novel PB1-F2 Polymorphisms", Frontiers in Microbiology, vol. 7, Article 262, Mar. 2016.

Zhang, Xiaojian et al., "Role of stem glycans attached haemagglutinin in the biological characteristics of H5N1 avian influenza virus", Journal of General Virology, 96, 1248-1257, 2015.

Zhang, Yan et al., "Glycosylation on Hemagglutinin Affects the Virulence and Pathogenicity of Pandemic H1N1/2009 Influenza A Virus in Mice", PLOS ONE, vol. 8, Issue 4, Apr. 2013.

Zhao, "Glycans of SARS-CoV-2 Spike Protein in Virus Infection and Antibody Production", Frontiers in Molecular Biosciences, Apr. 13, 2021; Entire Document; DOI: 10.3389/fmolb.2021.629873.

Zheng, J. et al., "Identification of N-linked glycosylation sites in the spike protein and their functional impact on the replication and infectivity of coronavirus infectious bronchitis virus in cell culture", Virology, Oct. 13, 2017, vol. 513, pp. 65-74; abstract; p. 65, 1st column, second paragraph; p. 66, col. 5th paragraph; p. 68, first column, first, third paragraphs; Table 3; figure 5; http://dx.doi.org/10.1016/j.virol.2017.10.003.

Office Action issued on Nov. 14, 2022, in Israel Patent Application No. 293502.

Office Action issued on May 17, 2023 in U.S. Appl. No. 17/998,208.

U.S. Appl. No. 18/005,573, filed Jan. 13, 2023, Che Ma.

U.S. Appl. No. 18/029,758, filed Mar. 31, 2023, Chi-Huey Wong.

(56) References Cited

OTHER PUBLICATIONS

U.S. Appl. No. 18/501,578, filed Nov. 3, 2023, Chi-Huey Wong.
U.S. Appl. No. 63/266,008, filed Dec. 27, 2021, Kuo-I Lin.
U.S. Appl. No. 63/458,102, filed Apr. 8, 2023, Chi-Huey Wong.
U.S. Appl. No. 63/581,389, filed Sep. 8, 2023, Chi-Huey Wong.
Dang, Juanjuan et al., "Multivalency-assisted membrane-penetrating siRNA delivery sensitizes photothermal ablation via inhibition of tumor glycolysis metabolism," Biomaterials, vol. 223, Dec. 2019, 119463.
Lostalé-Seijo, Irene and Montenegro, Javier, "Synthetic materials at the forefront of gene delivery," Nature Reviews Chemistry, vol. 2, Sep. 21, 2018, pp. 258-277.
Office Action issued in Taiwan Patent Application No. 111113932 on Oct. 16, 2023.
Sanda, Miloslav et al., "N- and O-Glycosylation of the SARS-COV-2 Spike Protein," Anal. Chem., vol. 93, No. 4, Jan. 7, 2021, pp. 2003-2009.
Torres-Vanegas, Julian D., "Delivery Systems for Nucleic Acids and Proteins: Barriers, Cell Capture Pathways and Nanocarriers," Pharmaceutics, vol. 13, No. 3, Mar. 22, 2021, pp. 428.
Vogel, Annette B. et al. "BNT162b vaccines protect rhesus macaques from SARS-COV-2," Nature, vol. 592, Feb. 1, 2021, pp. 283-289.
Bosch, Berend Jan et al.,"Coronavirus Escape from Heptad Repeat 2 (HR2)-Derived Peptide Entry Inhibition as a Result of Mutations in the HR1 Domain of the Spike Fusion Protein," J of Virol., Mar. 2008, vol. 82, No. 5, pp. 2580-2585.
Galili, Uri, "Amplifying immunogenicity of prospective Covid-19 vaccines by glycoengineering the coronavirus glycan-shield to present [alpha]-gal epitopes," Vaccine, 2020, vol. 38, pp. 6487-6499.
GenBank Accession BCN86353.1 accessed on Jan. 22, 2021. https://www.ncbi.nlm.nih.gov/protein/BCN86353.1?report=genbank&log$=protalign&blast_rank=2&RID=EYKWWEAA016.
GenBank: QLB39105.1 accessed on Jan. 1, 2020. https://www.ncbi.nlm.nih.gov/protein/QLB39105.1?report=genbank&log$=protalign&blast_rank=1&RID=EYKWWEAA016.
GenBank: QTA38985.1 accessed Mar. 21, 2021. https://www.ncbi.nlm.nih.gov/protein/QTA38985.1?report=genbank&log$=protalign&blast_rank=3&RID=EYKWWEAA016.
International Search Report and Written Opinion issued on Jun. 22, 2023 in International Patent Application No. PCT/US22/82428.
Official Action, dated Aug. 31, 2023, received in Russia Patent Application No. 2023100504. English translation provided.
Search Report, dated Aug. 31, 2023, received in Russia Patent Application No. 2023100504.
Tai, Wanbo et al., "Characterization of the receptor-binding domain (RBD) of 2019 novel coronavirus: implication for development of RBD protein as a viral attachment inhibitor and vaccine," Cell Mol Immunol. Jun. 2020;17(6):613-620 https://pubmed.ncbi.nlm.nih.gov/32203189/.
Tian, Jing-Hui et al., "SARS-CoV-2 spike glycoprotein vaccine candidate NVX-CoV2373 immunogenicity in baboons and protection in mice," Nature Communications, 2021, 14 pages. Downloaded Sep. 27, 2023: https://doi.org/10.1038/s41467-020-20653-8.
Weissman, Drew et al., "D614G Spike Mutation Increases SARS CoV-2 Susceptibility to Neutralization," Cell Host & Microbe, Jan. 13, 2021, vol. 29, pp. 23-31 (e1-e4).
Edwards, et al., "The Remarkable Flexibility of the Human Antibody Repertoire; Isolation of Over One Thousand Different Antibodies to a Single Protein, BLyS," J. Mol. Biol., Nov. 2003, 14:334(1):103-18; doi: 10.1016/j.jmb.2003.09.054. PMID 14596803.
Goel, Manisha et al., "Plasticity within the Antigen-Combining Site May Manifest as Molecular Mimicry in the Humoral Immune Response," J. Immunol., Dec. 15, 2004, 173(12):7358-67 PMID: 15585860 DOI: 10.4049/jimmunol.173.12.7358.
Janeway Jr., Charles A et al., "Immunobiology: The Immune System in Health and Disease," 3rd edition, Garland Publishing Inc., 1997, pp. 3:1-3:11.
Kanyavuz, Alexia et al., "Breaking the law: unconventional strategies for antibody diversification," Nat Rev Immunol., Jun. 2019, 19(6):355-368. doi:10.1038/S41577-019-0126-7. PMID: 30718829.
Lescar et al., "Crystal Structure of a Cross-reaction Complex between Fab F9.13.7 and Guinea Fowl Lysozyme," J Biol Chem., Jul. 1995, 270(30):18067-76. doi: 10.1074/jbc.270.30.18067. PMID: 7629116.
Lloyd, C. et al., "Modelling the human immune response: performance of a 10(11) human antibody repertoire against a broad panel of therapeutically relevant antigens," Protein Engineering Design & Selection, 2009, vol. 22, No. 3, pp. 159-168. doi: 10.1093/protein/gzn058.
Non-Final Office Action issued in U.S. Appl. No. 17/937,744 dated Jul. 5, 2023.
Rees-Spear, Chloe et al., "The effect of spike mutations on SARS-CoV-2 neutralization," Cell Rep., Mar. 2023, 34(12): 108890. Published online Mar. 6, 2021. doi: 10.1016/j.celrep.2021.108890: 10.1016/j.celrep.2021.108890 PMCID: PMC7936541 PMID: 33713594.
Rudikoff et al., "Single amino acid substitution altering antigen-binding specificity," Proc. Natl Acad Sci U S A, Mar. 1982, vol. 79(6), pp. 1979-1983. doi: 10.1073/pnas.79.6.1979. PC/D: 6804947.
Focosi, Daniele, "Neutralising antibody escape of SARS-CoV-2 spike protein: Risk assessment for antibody-based Covid-19 therapeutics and vaccines," Rev. Med Virol., 2021, vol. 31, 21 pages. e2231.
Magazine, Nicholas et al., "Mutations and Evolution of the SARS-CoV-2 Spike Protein," Viruses, 2022, vol. 14, 640, 11 pgs.
Office Action and Search Report issued in Taiwan Patent Application No. 111113933 on Mar. 26, 2024. English translation of search report.
Bernstein, David et al., "Immunogenicity of chimeric haemagglutinin-based, universal influenza virus vaccine candidates: interim results of a randomized, placebo-controlled, phase 1 clinical trial", The Lancet Infectious Disease, Elsevier, Amerstdam, NL, vol. 20, No. 1, Oct. 17, 2019, pp. 80-91, XP085982810. ISSN: 1473-3099, DOI: 10.1016/S1473-3099(19)30393-7.
Huang et al., "Impact of glycosylation on SARS-CoV-2 infection and broadly protective vaccine design," BioRxiv, May 25, 2021, DOI: https://doi.org/10.1101/2021.05.25.445523, internal pp. 1-48.
Galili, Uri, "COVID-19 variants as moving targets and how to sop them by glycoengineered whole-virus vaccines," Virulence, 12:1, 1717-1720, DOI: 10.1080/21505594.2021.1939924. (https://doi.org/10.1080/21505594.2021.1939924).
Watanabe, Yasunori et al., "Exploitation of glycosylation in enveloped virus pathobiology," BBA—General Subjects 1863, 2019), pp. 1480-1497.

* cited by examiner

| Position | 18 | 69 | 70 | 80 | 145 | 215 | 242 | 243 | 244 | 246 | 417 | 484 | 501 | 570 | 614 | 681 | 701 | 716 | 982 | 1118 |
|---|---|---|---|---|---|---|---|---|---|---|---|---|---|---|---|---|---|---|---|---|
| WT | L | H | V | Y | D | D | L | A | L | R | K | E | N | A | D | P | A | T | S | D |
| D614G | | | | | | | | | | | | | | | G | | | | | |
| B.1.1.7 | | - | - | | - | | | | | | | | Y | D | G | H | | I | A | H |
| B.1.351 | F | | | A | | | - | - | - | | N | K | Y | | G | | V | | | |
| RaGT13 | 97.4 % identity to SARS-CoV-2 | | | | | | | | | | | | | | | | | | | |
| SARS-CoV | 76.5 % identity to SARS-CoV-2 | | | | | | | | | | | | | | | | | | | |

CORONAVIRUS VACCINE

CROSS-REFERENCE TO RELATED APPLICATIONS

This application is a 371 National Phase of PCT/US22/71682, filed on Apr. 12, 2022, which claims priority to and benefit of U.S. Provisional Patent Application No. 63/173,752, filed on Apr. 12, 2021, and to U.S. Provisional Patent Application No. 63/63/190,199 filed on May 18, 2021, the contents of which are hereby incorporated by reference in their entirety.

SEQUENCE LISTING

The instant application contains a Sequence Listing which is submitted electronically in text format and is hereby incorporated by reference in its entirety. The text copy, created on Jan. 13, 2023, is named "A1000-00900NP_SeqListing_20230113.txt" and is 37 kilobytes in size.

BACKGROUND OF THE PRESENT DISCLOSURE

Covid-19 outbreak has caused over three millions of deaths worldwide since the first case reported in December, 2019. Currently several COVID-19 vaccines against SARS-CoV-2 infection are being developed in clinical trial stage, and some vaccines have been authorized for human usage. Although a number of approved vaccines demonstrated high efficacy, genetic variants of SARS-CoV-2 have been emerging and circulating around the world throughout the COVID-19 pandemic.

Therefore, there is an urgent need for improved COVID-19 vaccines for better prevention of the emerging coronavirus infections and/or reducing the severity of life-threatening coronavirus infections.

SUMMARY OF THE PRESENT DISCLOSURE

The spike protein of SARS-CoV-2 is extensively glycosylated. The present disclosure stems from the recognition that immunization with a modified SARS-CoV-2 spike protein lacking glycan shields or being less shielded by glycans elicited an enhanced immune response against SARS-CoV-2 and the variants of concern (e.g. alpha, gamma, delta and omicron), as compared to a native spike protein of SARS-CoV-2 or a variant thereof 12 highly conserved epitopes (SEQ ID: 41-52) located in the receptor-binding domain (RBD) and the subunit 2 (S2) including the heptad repeat 2 (HR2) domain were identified based on the alignment of more than 6 million S protein sequences from GISAID. Removal of the glycan shields by N-glycan trimming to better expose these highly conserved epitopes offers an effective approach to developing broadly protective vaccines against SARS-CoV-2 and variants. N-glycan trimming of spike protein can be achieved by in vitro glycoengineering. The glycoengineered spike protein thereby exposes the highly conserved epitopes shielded by glycans and at the same time preserves the tertiary structure of the spike protein. The present disclosure therefore provides improved immunogens, vaccines, and methods for better prevention and treatment of the emerging coronavirus (e.g. SARS-CoV-2) infections.

Accordingly, the present disclosure provides an immunogen comprising a glycoengineered coronavirus spike protein comprising a plurality of truncated N-glycans and unmodified O-glycans (e.g. O-linked oligosaccharides). In some embodiments, the plurality of truncated N-glycans are located in the receptor-binding domain (RBD), thereby exposing a plurality of highly conserved epitopes having amino acid sequences of TESIVRFPNITNL (SEQ ID NO.: 41), NITNLCPFGEVFNATR (SEQ ID NO: 42), LYNSASFSTFK (SEQ ID NO: 43), LDSKVGGNYN (SEQ ID NO: 44), KSNLKPFERDIST (SEQ ID NO: 45), KPFERDISTEIYQAG (SEQ ID NO: 46) and/or GPKKSTNLVKNKC (SEQ ID NO: 47). In some embodiments, the plurality of truncated N-glycans are located in the heptad repeat 2 (HR2) domain, thereby exposing a plurality of highly conserved epitopes having amino acid sequences of NCDVVIGIVNNTVY (SEQ ID NO: 48), PELDSFKEELDKYFKNHTS (SEQ ID NO: 49), VNIQKEIDRLNEVA (SEQ ID NO: 50), NLNESLIDLQ (SEQ ID NO: 51) and/or LGKYEQYIKWP (SEQ ID NO: 52).

In some embodiments, the plurality of truncated N-glycans are located in the receptor-binding domain (RBD) and in the heptad repeat 2 (HR2) domain, thereby exposing a plurality of highly conserved epitopes having amino acid sequences of TESIVRFPNITNL (SEQ ID NO.: 41), NITNLCPFGEVFNATR (SEQ ID NO: 42), LYNSASF-STFK (SEQ ID NO: 43), LDSKVGGNYN (SEQ ID NO: 44), KSNLKPFERDIST (SEQ ID NO: 45), KPFERDIS-TEIYQAG (SEQ ID NO: 46), GPKKSTNLVKNKC (SEQ ID NO: 47), NCDVVIGIVNNTVY (SEQ ID NO: 48), PELDSFKEELDKYFKNHTS (SEQ ID NO: 49), VNIQKEIDRLNEVA (SEQ ID NO: 50), NLNESLIDLQ (SEQ ID NO: 51) and/or LGKYEQYIKWP (SEQ ID NO: 52).

The glycoengineered coronavirus spike protein described herein comprises the amino acid sequence of SEQ ID NO: 1 or a variant thereof having at least 90% sequence identity to the amino acid sequence of SEQ ID NO: 1, or an immunologically active fragment of the amino acid sequence or the variant.

In some embodiments, the glycoengineered coronavirus spike protein comprises a polypeptide consisting of an amino acid sequence of SEQ ID NO: 1, wherein the polypeptide consists of 22 truncated N-glycans, each having a GlcNAc moiety.

In some embodiments, the glycoengineered coronavirus spike protein comprises a polypeptide consisting of an amino acid sequence of SEQ ID NO: 2, wherein the polypeptide consists of 21 truncated N-glycans, each having a GlcNAc moiety.

In some embodiments, the truncated N-glycans are monosaccharides, disaccharides or trisaccharides. In some embodiments, the truncated N-glycans are monosaccharides. In preferred embodiments, the monosaccharides are N-acetylglucosamines (GlcNAc).

In preferred embodiments, the truncated N-glycans described herein are substantially homogeneous. The term "homogeneous" is intended to mean a glycosylation pattern represented by one desired glycan species. The terms "substantially homogeneous" used herein is intended to mean that at least 80%, at least 85%, at least 90%, 91%, 92%, 93%, 94%, 95%, 96%, 97%, 98%, or at least 99% of the glycoprotein present in the composition is represented by one desired glycoform (e.g., GlcNAc-decorated) with a trace amount of undesired glycoforms being present in the composition. By "trace amount" is intended that any given undesired glycoform that is present in the glycoprotein composition is present at less than 5%, preferably less than 4%, less than 3%, less than 2%, less than 1%, and even less than 0.5% or even less than 0.1% of the total glycoprotein.

As described herein, the terms "spike protein" and "spike glycoprotein" and "coronavirus spike protein" are used interchangeable. The glycoengineered spike protein described herein can be generated from a native coronavirus spike protein by glycoengineering (e.g., glycoengineering in vitro or in vivo). In some embodiments, the glycoengineered spike protein is generated using one or more of chemical or enzymatic methods. In some embodiments, the glycoengineered spike protein is generated using endoglycosidase H (Endo H).

In some embodiments, the native coronavirus spike protein described herein is the spike protein of severe acute respiratory syndrome coronavirus 2 (SAR-CoV-2) or variants thereof. SARS-CoV-2 described herein is the Wuhan strain of SARS-CoV-2 (hCoV/Wuhan/WH01/2019). The variants of SARS-CoV-2 described herein include, but are not limited to, D614G, Alpha (B.1.1.7 and Q lineages), Beta (B. 1.351 and descendent lineages), Gamma (P.1 and descendent lineages), Epsilon (B.1.427 and B.1.429), Eta (B.1.525), Iota (B.1.526), Kappa (B.1.617.1), 1.617.3, Mu (B.1.621, B.1.621.1), Zeta (P.2), Delta (B.1617.2 and AY lineages) and Omicron (B.1.1.529 and BA lineages). In some embodiments, the native coronavirus spike protein is the spike protein of bat coronavirus RaTG13 or variants thereof.

As described herein, the term "native coronavirus spike protein", "native coronavirus spike glycoprotein", "native spike glycoprotein" and "native spike protein" is interchangeable.

In some embodiments, the glycoengineered spike protein described herein is present as a trimer (e.g., a trimer in solution). The glycoengineered spike protein described herein may retain the same tertiary structure as its native coronavirus spike protein.

As described herein, the glycoengineered spike protein is capable of inducing an enhanced immune response relative to its native coronavirus spike protein. The enhanced immune response is an increased IgG titer, an increased IgM titer, an increased CD4 T cell response, an increased CD8 T cell response, an increased neutralization titer, or a combination thereof.

In another aspect, the present invention provides an immunogenic composition, comprising: (a) the immunogen of the disclosure, and (b) optionally, an adjuvant.

As described herein, the adjuvant may include, but is not limited to, aluminum hydroxide, aluminum phosphate, incomplete Freund's adjuvant (IFA), squalene, Alum, Alhydrogel, MF59, QS-21, CpG 1018, AS03, AS37, Matrix-M or a combination thereof.

The coronavirus described herein may include SARS-CoV-2 and its variants, and may include bat coronavirus RaTG13 or its variants. In preferred embodiments, the coronavirus infection is caused by SARS-CoV-2 and its variants.

As described herein, the immunogenic composition is capable of eliciting an enhanced immune response relative to a vaccine using its native SAR-CoV-2 spike protein, thereby serving as an improved COVID-19 vaccine against coronavirus infections caused by SAR-CoV-2 or a variant thereof.

In another aspect, the present invention provides a method for eliciting an immune response against SAR-CoV-2 or variants in a subject in need thereof, comprising administering to the subject an effective amount of an immunogenic composition of the present invention.

In another aspect, the present invention provides a method for protecting a subject in need thereof from infection with SAR-CoV-2 or variants, comprising administering to the subject an effective amount of the immunogenic composition of the present invention.

In another aspect, the present invention provides a method for preventing a subject in need thereof from contracting COVID-19 disease, comprising administering to the subject an effective amount of the immunogenic composition of the present invention.

In another aspect, the present invention provides use of the immunogenic composition of the present invention for eliciting an immune response against SARS-CoV-2 in a subject in need thereof.

In another aspect, the present invention provides use of the immunogenic composition of the present invention for protecting a subject in need thereof from infection with SARS-CoV-2.

In another aspect, the present invention provides use of the immunogenic composition of the present invention for preventing a subject in need thereof from contracting COVID-19 disease.

These and other aspects will become apparent from the following description of the preferred embodiment taken in conjunction with the following drawings, although variations and modifications therein may be affected without departing from the spirit and scope of the novel concepts of the disclosure.

BRIEF DESCRIPTION OF THE DRAWINGS

The subject patent application file contains at least one drawing executed in color. Copies of this patent or patent application publication with color drawing(s) will be provided by the U.S. Patent Office upon request and payment of the necessary fee. The following drawings form part of the present specification and are included to further demonstrate certain aspects of the present disclosure, the inventions of which can be better understood by reference to one or more of these drawings in combination with the detailed description of specific embodiments presented herein.

DETAILED DESCRIPTION OF THE INVENTION

Figure 1:
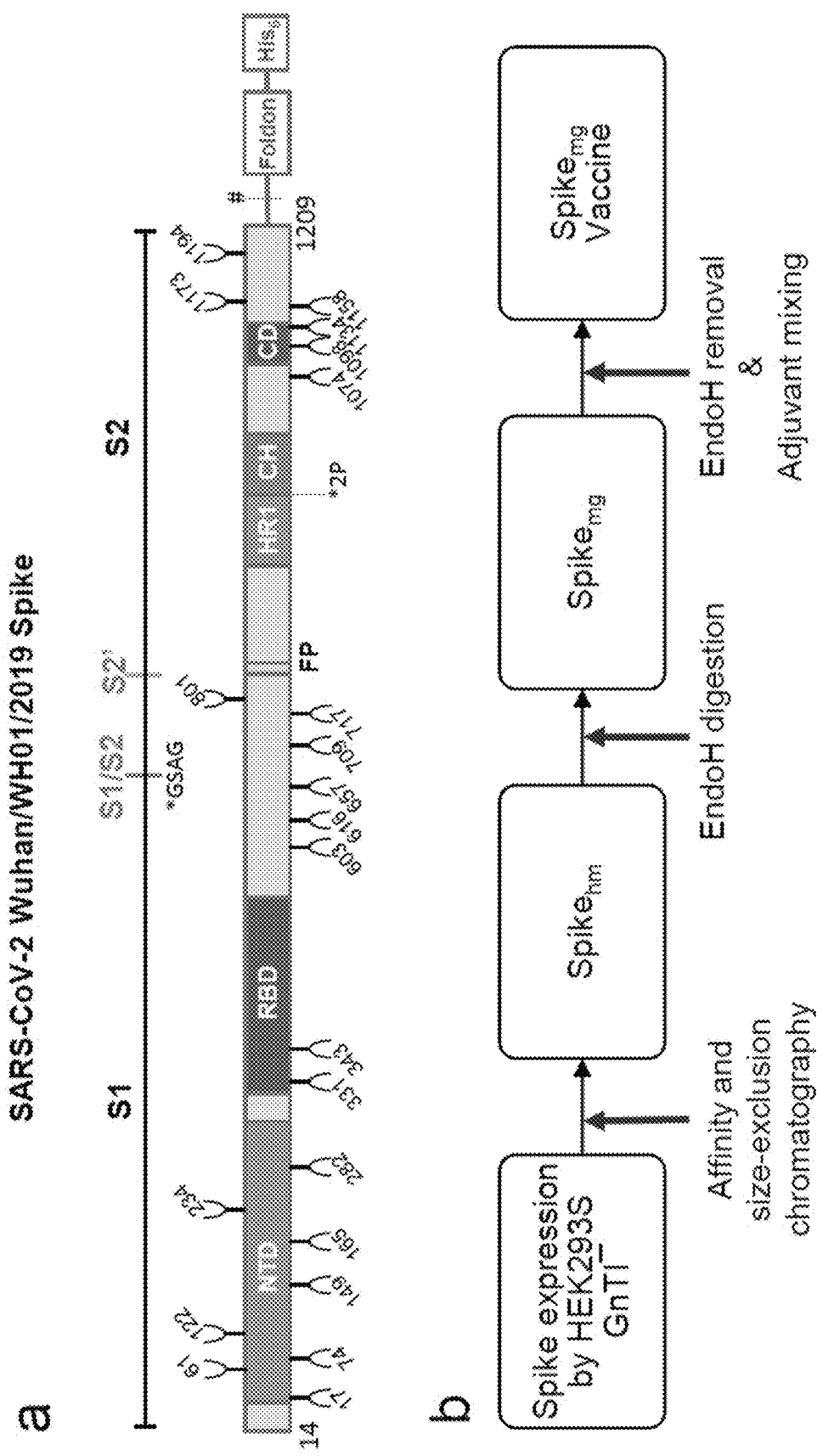
FIGS. 1 (*a*) to (*f*). Design and characterization of glycoengineered spike protein with mono-GlcNAc-decorated ($S_{MG}$) protein vaccine. (a) Schematic representation of the recombinant SARS-CoV-2 Spike glycoprotein construct. Protein domains are illustrated as N-terminal domain (NTD), receptor binding domain (RBD), fusion peptide (FP), heptad repeat 1 (HR1), heptad repeat 2 (H1R2), central helix (CH), and connector domain (CD). The C-terminus of soluble Spike protein is linked with fold on sequence and His-tag ($His_6$). The furin cleavage site was substituted by GSAG (SEQ ID NO: 9) residues and the two proline mutations (K986P, and V987P) fix the Spike protein in the prefusion state. The positions of N-linked glycosylation sequons (N-X-S/T, where X≠P) are shown as branches (N, Asn; X, any residue; S, Ser; T, Thr; P, Pro). The pound site represents the thrombin cleavage site. (b) Schematic overview of mono-GlcNAc decorated Spike vaccine production. $S_{HM}$, Spike with high mannose type N-glycans; $S_{MG}$, Spike with GlcNAc at its N-glycosylation sites. (c) Size-exclusion chromatography of purified $S_{MG}$. The black curve represents the $S_{MG}$ and the gray curve shows the protein molecular weight markers. (d) SDS-PAGE analysis of $S_{FG}$ (Spike with typical complex type N-glycans), $S_{HM}$ and $S_{MG}$. (e) Structure model of $S_{MG}$. Models were created with Protein Data Bank (PDB) ID code 7CN9 by adding glycan using Wincootmand displayed with program ChimeraX. (f) Mass Spectrometry analysis of the N-glycan compositions of the $S_{FG}$ and $S_{MG}$.
Figure 1:
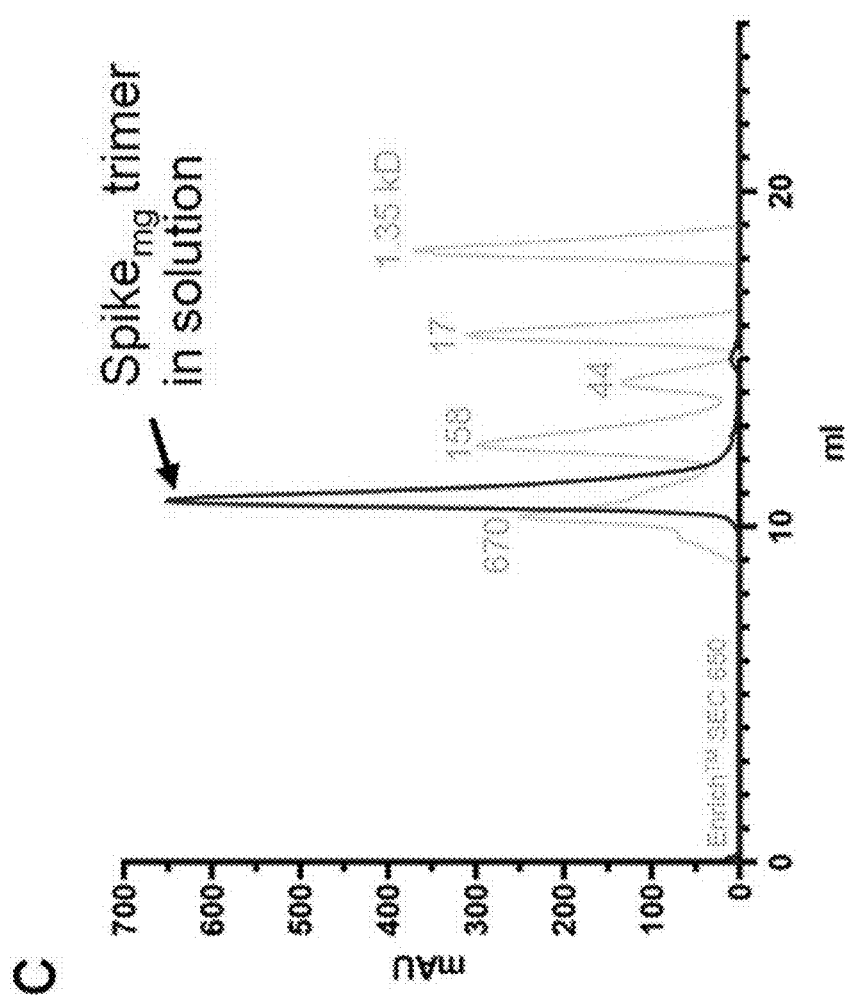
Figure 1:
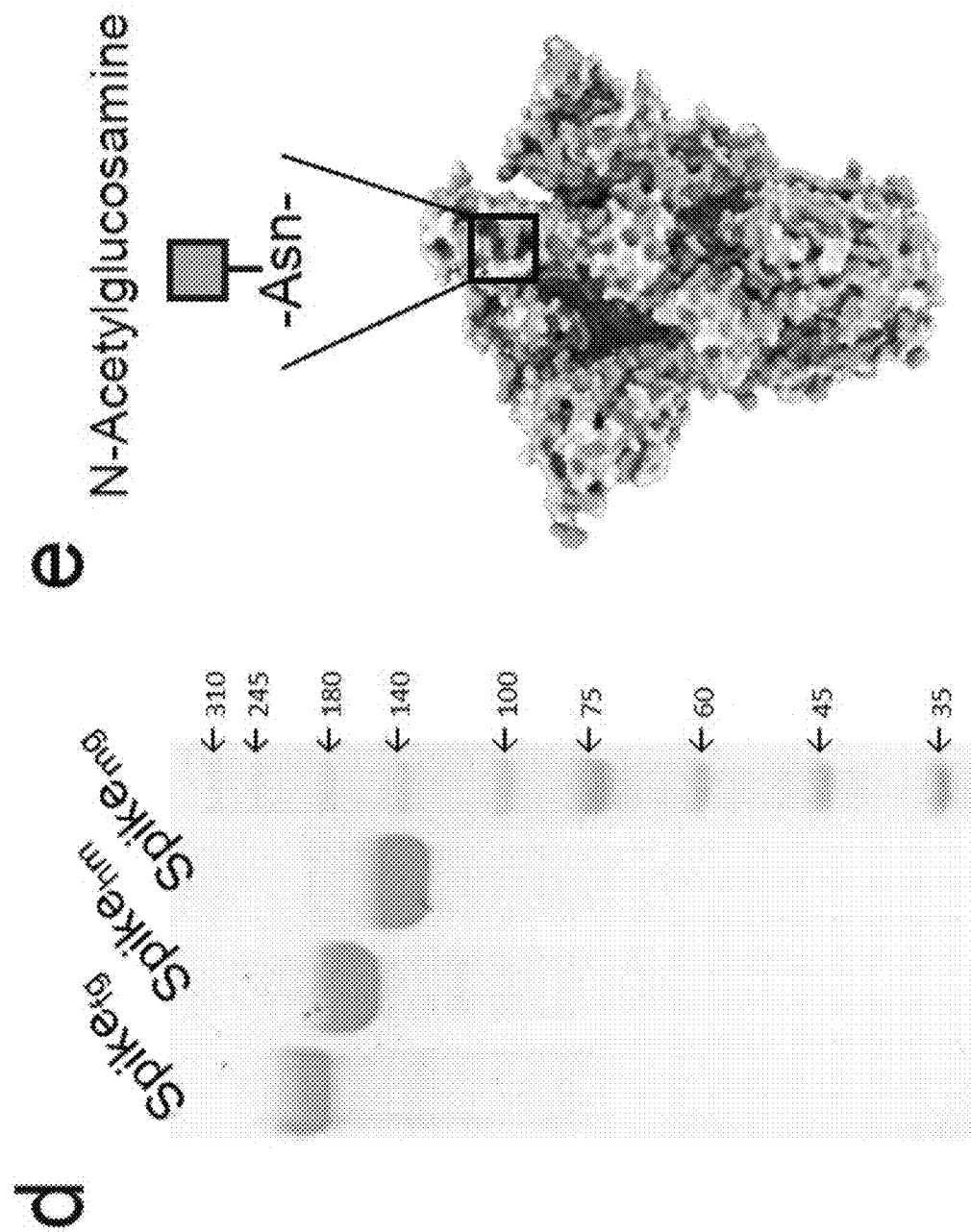
Figure 1:
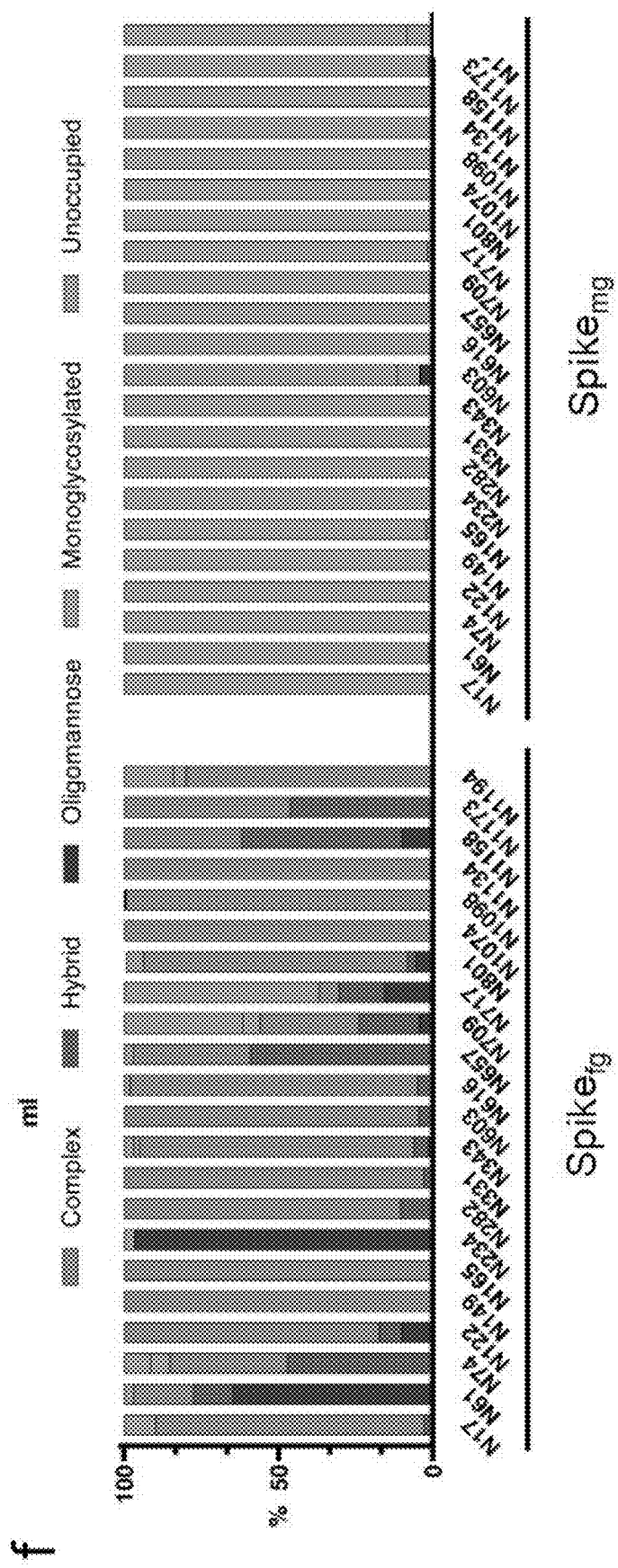

In the following detailed description of embodiments of the present disclosure, reference is made to the accompanying drawings in which like references indicate similar elements, and in which is shown by way of illustration specific embodiments in which the present disclosure may be practiced. These embodiments are described in sufficient detail to enable those skilled in the art to practice the present disclosure, and it is to be understood that other embodiments may be utilized and that logical, structural, functional, and other changes may be made without departing from the scope of the present disclosure. The following detailed description is, therefore, not to be taken in a limiting sense.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent or later-developed techniques which would be apparent to one of skill in the art. In addition, in order to more clearly and concisely describe the subject matter which is the invention, the following definitions are provided for certain terms which are used in the specification and appended claims.

As used herein, and in the appended claims, the singular forms "a", "an", and "the" include plural referents unless the context clearly dictates otherwise. Thus, for example, reference to "a protein" can refer to one protein or to mixtures of such protein, and reference to "the method" includes reference to equivalent steps and/or methods known to those skilled in the art, and so forth.

As used herein, the term "mutation" refers to a single change in a virus's genome (genetic code). Mutations happen frequently, but only sometimes change the characteristics of the virus.

As used herein, the term "lineage" refers to a group of closely related viruses with a common ancestor. SARS-CoV-2 has many lineages; all cause COVID-19.

As used herein, the term "variant" refers to a viral genome (genetic code) that may contain one or more mutations. In some cases, a group of variants with similar genetic changes, such as a lineage or group of lineages, may be designated by public health organizations as a Variant of Concern (VOC) or a Variant of Interest (VOI) due to shared attributes and characteristics that may require public health action.

As used herein, the term "adjuvant" refers to a compound that, when used in combination with an immunogen, augments or otherwise alters or modifies the immune response induced against the immunogen. Modification of the immune response may include intensification or broadening the specificity of either or both antibody and cellular immune responses.

As used herein, the term "about" or "approximately" when preceding a numerical value indicates the value plus or minus a range of 10%. For example, "about 100" encompasses 90 and 110.

As used herein, an "immunogenic composition" is a composition that comprises an antigen where administration of the composition to a subject results in the development in the subject of a humoral and/or a cellular immune response to the antigen.

As described herein, the terms "spike protein" and "spike glycoprotein" and "coronavirus spike protein" are used interchangeably.

The terms "substantially homogeneous" used herein is intended to mean that at least 80%, at least 85%, at least 90%, 91%, 92%, 93%, 94%, 95%, 96%, 97%, 98%, or at least 99% of the glycoprotein present in the composition is represented by one desired glycoform (e.g., mono-GlcNAc-decorated) with a trace amount of undesired glycoforms being present in the composition. By "trace amount" is intended that any given undesired glycoform that is present in the glycoprotein composition is present at less than 5%, preferably less than 4%, less than 3%, less than 2%, less than 1%, and even less than 0.5% or even less than 0.1% of the total glycoprotein.

The terms "treat," "treatment," and ""reating," as used herein, refer to an approach for obtaining beneficial or desired results, for example, clinical results. For the purposes of this disclosure, beneficial or desired results may include inhibiting or suppressing the initiation or progression of an infection or a disease; ameliorating, or reducing the development of, symptoms of an infection or disease; or a combination thereof.

The terms "preventing" and "prevention," as used herein, are used interchangeably with "prophylaxis" and can mean complete prevention of an infection, or prevention of the development of symptoms of that infection; a delay in the onset of an infection or its symptoms; or a decrease in the severity of a subsequently developed infection or its symptoms.

As used herein an "effective amount" refers to an amount of an immunogen sufficient to induce an immune response that reduces at least one symptom of pathogen infection. An effective dose or effective amount may be determined e.g., by measuring amounts of neutralizing secretory and/or serum antibodies, e.g., by plaque neutralization, complement fixation, enzyme-linked immunosorbent (ELISA), or microneutralization assay.

As used herein, the term "vaccine" refers to an immunogenic composition (with or without an adjuvant), such as an immunogen derived from a coronavirus, which is used to induce an immune response against the coronavirus that provides protective immunity (e.g., immunity that protects a subject against infection with the coronavirus and/or reduces the severity of the condition caused by infection with the coronavirus). The protective immune response may include formation of antibodies and/or a cell-mediated response.

Depending on context, the term "vaccine" may also refer to a suspension or solution of an immunogen that is administered to a subject to produce protective immunity.

As used herein, the term "subject" includes humans and other animals. Typically, the subject is a human. For example, the subject may be an adult, a teenager, a child (2 years to 14 years of age), an infant (birth to 2 year), or a neonate (up to 2 months). In particular aspects, the subject is up to 4 months old, or up to 6 months old. In some aspects, the adults are seniors about 65 years or older, or about 60 years or older. In some aspects, the subject is a pregnant woman or a woman intending to become pregnant. In other aspects, subject is not a human; for example a non-human primate; for example, a baboon, a chimpanzee, a gorilla, or a macaque. In certain aspects, the subject may be a pet, such as a dog or cat.

As used herein, the term "pharmaceutically acceptable" means being approved by a regulatory agency of a U.S. Federal or a state government or listed in the U.S. Pharmacopeia, European Pharmacopeia or other generally recognized pharmacopeia for use in mammals, and more particularly in humans. These compositions can be useful as a vaccine and/or antigenic compositions for inducing a protective immune response in a vertebrate.

Severe acute respiratory syndrome coronavirus 2 (SARS-CoV-2) is an enveloped, positive-sense, single-stranded RNA virus that causes coronavirus disease 2019 (COVID-19). Virus particles include the RNA genetic material and structural proteins needed for invasion of host cells. Once inside the cell the infecting RNA is used to encode structural proteins that make up virus particles, nonstructural proteins that direct virus assembly, transcription, replication and host control and accessory proteins whose function has not been determined. The structural proteins of SARS-CoV-2 include the envelope protein (E), spike or surface glycoprotein (S), membrane protein (M) and the nucleocapsid protein (N). The spike glycoprotein is found on the outside of the virus particle and gives coronavirus viruses their crown-like appearance. This glycoprotein mediates attachment of the virus particle and entry into the host cell.

S protein generated by lung epithelial cells has glycoforms associated with increased infectivity. Compared to the fully glycosylated S protein, immunization of S protein with N-glycans trimmed to the mono-GlcNAc decorated state ($S_{MG}$) elicited stronger immune responses and better protection for human angiotensin-converting enzyme 2 (hACE2) transgenic mice against variants of concern (VOCs). In addition, a broadly neutralizing monoclonal antibody was identified from $S_{MG}$-immunized mice that could neutralize wild-type SARS-CoV-2 and VOCs with subpicomolar potency.

A glycoengineered spike protein of the disclosure comprises a polypeptide having an amino acid sequence of SEQ ID NO: 1 or a variant thereof having at least 90% sequence identity to the amino acid sequence of SEQ TD NO: 1, or an immunologically active fragment of the amino acid sequence or the variant. The amino acid sequence of SEQ TD NO: 1 is shown below.

SEQ ID NO: 1

```
QCVNLTTRTQLPPAYTNSFTRGVYYPDKVFRSSVLHSTQDLFLPFFSNV

TWFHAIHVSGTNGTKRFDNPVLPFNDGVYFASTEKSNIIRGWIFGTTLD

SKTQSLLIVNNATNVVIKVCEFQFCNDPFLGVYYHKNNKSWMESEFRVY
```

-continued

```
SSANNCTFEYVSQPFLMDLEGKQGNFKNLREFVFKNIDGYFKIYSKHTP

INLVRDLPQGESALEPLVDLPIGINITRFQTLLALHRSYLTPGDSSSGW

TAGAAAYYVGYLQPRTELLKYNENGTITDAVDCALDPLSETKCTLKSFT

VEKGIYQTSNERVQPTESIVRFPNITNLCPFGEVENATRFASVYAWNRK

RISNCVADYSVLYNSASFSTFKCYGVSPTKLNDLCFTNVYADSFVIRGD

EVRQIAPGQTGKIADYNYKLPDDFTGCVIAWNSNNLDSKVGGNYNYLYR

LERKSNLKPFERDISTEIYQAGSTPCNGVEGENCYFPLQSYGFQPTNGV

GYQPYRVVVLSFELLHAPATVCGPKKSTNLVKNKCVNFNFNGLTGTGVL

TESNKKELPFQQFGRDIADTTDAVRDPQTLEILDITPCSFGGVSVITPG

TNTSNQVAVLYQDVNCTEVPVAIHADQLTPTWRVYSTGSNVFQTRAGCL

IGAEHVNNSYECDIPIGAGICASYQTQTNSPRRARSVASQSIIAYTMSL

GAENSVAYSNNSIAIPTNFTISVTTEILPVSMTKTSVDCTMYICGDSTE

CSNLLLQYGSFCTQLNRALTGIAVEQDKNTQEVFAQVKQIYKTPPIKDF

GGFNFSQILPDPSKPSKRSFIEDLLFNKVTLADAGFIKQYGDCLGDIAA

RDLICAQKENGLTVLPPLLTDEMIAQYTSALLAGTITSGWTFGAGAALQ

IPFAMQMAYRENGIGVTQNVLYENQKLIANQFNSAIGKIQDSLSSTASA

LGKLQDVVNQNAQALNTLVKQLSSNFGAISSVLNDILSRLDKVEAEVQI

DRLITGRLQSLQTYVTQQLIRAAEIRASANLAATKMSECVLGQSKRVDF

CGKGYHLMSFPQSAPHGVVFLHVTYVPAQEKNFTTAPAICHDGKAHFPR

EGVFVSNGTHWFVTQRNFYEPQIITTDNTFVSGNCDVVIGIVNNTVYDP

LQPELDSFKEELDKYFKNHTSPDVDLGDISGINASVVNIQKEIDRLNEV

AKNLNESLIDLQELGKYEQY
```

In one embodiment, the glycoengineered spike protein of the disclosure comprises a polypeptide having the amino acids as shown in SEQ TD NO: 2 below.

SEQ ID NO: 2

```
QCVNLRTRTQLPPAYTNSFTRGVYYPDKVFRSSVLHSTQDLFLPFFSNVT

WFHAIHVSGTNGTKRFDNPVLPFNDGVYFASTEKSNIIRGWIFGTTLDSK

TQSLLIVNNATNVVIKVCEFQFCNDPFLDVYYHKNNKSWMESGVYSSANN

CTFEYVSQPFLMDLEGKQGNFKNLREFVFKNIDGYFKIYSKHTPINLVRD

LPQGFSALEPLVDLPIGINITRFQTLLALHRSYLTPGDSSSGWTAGAAAY

YVGYLQPRTFLLKYNENGTITDAVDCALDPLSETKCTLKSFTVEKGIYQT

SNERVQPTESIVRFPNITNLCPFGEVENATRFASVYAWNRKRISNCVADY

SVLYNSASFSTFKCYGVSPTKLNDLCFTNVYADSFVIRGDEVRQIAPGQT

GKIADYNYKLPDDFTGCVIAWNSNNLDSKVGGNYNYRYRLFRKSNLKPFE

RDISTEIYQAGSKPCNGVEGENCYFPLQSYGFQPTNGVGYQPYRVVVLSF

ELLHAPATVCGPKKSTNLVKNKCVNFNFNGLTGTGVLTESNKKFLPFQQF

GRDIADTTDAVRDPQTLEILDITPCSFGGVSVITPGTNTSNQVAVLYQGV

NCTEVPVAIHADQLTPTWRVYSTGSNVFQTRAGCLIGAEHVNNSYECDIP

IGAGICASYQTQTNSRGSAGSVASQSIIAYTMSLGAENSVAYSNNSIAIP

TNFTISVTTEILPVSMTKTSVDCTMYICGDSTECSNLLLQYGSFCTQLNR
```

-continued
```
ALTGIAVEQDKNTQEVFAQVKQIYKTPPIKDFGGFNFSQILPDPSKPSKR

SFIEDLLENKVTLADAGFIKQYGDCLGDIAARDLICAQKFNGLTVLPPLL

TDEMIAQYTSALLAGTITSGWTFGAGAALQIPFAMQMAYRENGIGVTQNV

LYENQKLIANQFNSAIGKIQDSLSSTASALGKLQNVVNQNAQALNTLVKQ

LSSNFGAISSVLNDILSRLDPPEAEVQIDRLITGRLQSLQTYVTQQLIRA

AEIRASANLAATKMSECVLGQSKRVDFCGKGYHLMSFPQSAPHGVVFLHV

TYVPAQEKNFTTAPAICHDGKAHFPREGVFVSNGTHWFVTQRNFYEPQII

TTDNTFVSGNCDVVIGIVNNTVYDPLQPELDSFKEELDKYFKNHTSPDVD

LGDISGINASVVNIQKEIDRLNEVAKNLNESLIDLQELGKYEQ
```

As described herein, a glycoengineered spike protein of SARS-CoV-2 or a variant thereof may include those comprising an amino acid sequence which (i) are substantially identical to the amino acid sequences set forth in SEQ ID NO: 1 (e.g., at least 90%, 95% or 97% identical to SEQ ID NO: 1 such as SEQ ID NO:2); and (ii) are encoded by a nucleic acid sequence capable of hybridizing under at least moderately stringent conditions to any nucleic acid sequence encoding the spike protein set forth herein or capable of hybridizing under at least moderately stringent conditions to any nucleic acid sequence encoding the spike protein set forth herein, but for the use of synonymous codons (e.g. a codon which does not have the identical nucleotide sequence, but which encodes the identical amino acid).

The analysis of cell-specific glycoform distribution, sequence conservation, glycan shielding, and their mutual correlations led to the design of $S_{MG}$ vaccine, in which essentially all glycan shields are removed. SARS-CoV-2 S protein glycosylation has major influence on virus infection, protein integrity, and immune responses. The S protein from lung epithelial cells contains more sialylated complex-type glycans to facilitate receptor binding, and glycosites N801 and N1194 were shown to be essential for S protein folding and viral infection. This made the conserved epitopes better exposed to the immune system so that more effective and broadly protective B cell and T cell responses could be elicited against the virus and variants.

The glycoengineered coronavirus spike protein of the present disclosure targets the entire S protein ectodomain, particularly the conserved domains shielded by glycans, stimulating the elicitation of both RBD and non-RBD-neutralizing antibodies and CD8 T cell responses that are critical for cross protection.

In certain aspects, the present disclosure provides a vaccine or a pharmaceutical composition comprising the immunogen as described herein. The present disclosure also provides a method for treating or preventing coronavirus infection in which the method comprises administering to a subject (e.g., a mammal) in need thereof an effective amount of an immunogen, a pharmaceutical composition, or a vaccine as described herein.

In one embodiment, the vaccine may include an adjuvant. Exemplary adjuvants include, but are not limited to, aluminum hydroxide, aluminum phosphate, incomplete Freund's adjuvant (IFA), squalene, Alum, Alhydrogel, MF59, QS-21, CpG 1018, AS03, AS37, Matrix-M or a combination thereof.

The vaccine or pharmaceutical composition may be formulated using any suitable method. Formulation of with standard pharmaceutically acceptable carriers and/or excipients may be carried out using routine methods in the pharmaceutical art. The exact nature of a formulation will depend upon several factors including the vaccine to be administered and the desired route of administration. Suitable types of formulation are fully described in Remington's Pharmaceutical Sciences, 19th Edition, Mack Publishing Company, Eastern Pennsylvania, USA.

The vaccine or pharmaceutical composition as described herein may be administered by any route. Such methods comprise application e.g. parenterally, such as through all routes of injection into or through the skin: e.g. intramuscular, intravenous, intraperitoneal, intradermal, mucosal, submucosal, or subcutaneous. Also, they may be applied by topical application as a drop, spray, gel or ointment to the mucosal epithelium of the eye, nose, mouth, anus, or vagina, or onto the epidermis of the outer skin at any part of the body. Other possible routes of application are by spray, aerosol, or powder application through inhalation via the respiratory tract. Alternatively, application can be via the alimentary route. The effective amount of the vaccine composition may be dependent on any number of variables, including without limitation, the species, breed, size, height, weight, age, overall health of the patient, the type of formulation, or the mode or manner or administration. The appropriate effective amount can be routinely determined by those of skill in the art using routine optimization techniques and the skilled and informed judgment of the practitioner and other factors evident to those skilled in the art.

In one embodiment, The composition can comprises an additional therapeutic agent such as an anti-viral agent. The provided pharmaceutical composition is useful for treating a coronavirus infection. Examples of the additional anti-viral agent include, but are not limited to, ribavirin, penciclovir, nitazoxanide, nafamostat, chloroquine, remdesivir (GS-5734) and favipiravir (T-705), interferon, adefovir, tenofovir, acyclovir, brivudin, cidofovir, fomivirsen, foscarnet, ganciclovir, amantadine, rimantadine, zanamivir, rerndesivir, molnupiravir and paxlovid.

Unless otherwise defined, all technical and scientific terms used herein have the same meaning as commonly understood by one of ordinary skill in the art. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

Example 1: Gene Constructs

The SARS-CoV-2 spike sequences were designed based on the gene sequences downloaded from GISAID database. A total of 1,117,474 S protein sequences of all available SARS-CoV-2 strains were extracted from the GISAID (Global Initiative on Sharing Avian Influenza Data) database (version: 18 Apr. 2021).

DNA sequences of spike protein from SARS-CoV-2 Wuhan/WH01/2019 and Delta variant were synthesized with codons optimized for human cell expression. The furine cleavage site were replaced with GSAG (SEQ ID NO: 9) and the 2P substitutes were designed for protein to stay in prefusion state. The transmembrane domain was replaced with the thrombin cleavage site, foldon, and the histidine-tag at the C terminus of the spike. The modified HA sequence was cloned into pTT vector for protein expression and purification.

Example 2: SARS-CoV-2 S Protein Expression and Purification

The plasmid that encodes the secreted SARS-CoV-2 spike was transfected into the human embryonic kidney cell lines of either HEK293EBNA (ATCC number CRL-10852) or the HEK293S GnTI⁻ cells by using transfection reagent (either polyethyleneimine or FectoPRO) and were cultured in Freestyle 293 expression medium (Invitrogen) supplemented with 0.5% bovine calf serum. The supernatant was collected 5 days after transfection and cleared by centrifugation. Then, Spike proteins were purified with Nickel-chelation chromatography and eluted fractions were concentrated by a Millipore Amicon Ultra Filter (100 kDa) and loaded onto a Superpose™ 6 gel filtration column (10/300 GL; GE) pre-equilibrated in tris-based buffer (20 mM tris/HCl, 20 mM NaCl, 50 mM glutamate, 50 mM Arginine), and the corresponding trimer fractions were collected. The purified $S_{HM}$ were treated with Endo H (NEB) overnight at Room Temperature to produce Spike protein with a single GlcNAc at the glycosylation sites, the $Spike_{mg}$. For EndoH removal, $S_{MG}$ were further purified by buffer exchange using Millipore Amicon Ultra Filter (100 kDa). Expression and purification method is modified from the lab's previous research published in PNAS.

The production of glycan-engineered pseudoviruses in (FIG. 1D) followed previous studies (Y. Watanabe, J. D. Allen, D. Wrapp, J. S. McLellan, M. Crispin, Site-specific glycan analysis of the SARS-CoV-2 spike. *Science* 369, 330-333 (2020); Q. Yang, T. A. Hughes, A. Kelkar, X. Yu, K. Cheng, S. Park, W.-C. Huang, J. F. Lovell, S. Neelamegham, Inhibition of SARS-CoV-2 viral entry upon blocking N- and O-glycan elaboration. *eLife* 9, e61552 (2020)). For production of glycosite-specific S mutant pseudoviruses (FIG. 1F), HEK293T cells were transiently transfected with pVax-nCoV-SΔ19 construct carrying mutations at each glycosite and luciferase-expressing HIV-1 genome plasmid (pNL4-3.luc.RE).

Example 3: $S_{MG}$ Protein Characterization

To characterize the $S_{MG}$ protein, the size-exclusion chromatography using ENrich™ SEC 650 (10×300 column; Biorad) preequilibrated in tris-based buffer (20 mM tris/HCl, 20 mM NaCl, 50 mM glutamate, 50 mM Arginine) was performed. Then, to check the purity of protein sample, samples were combined with loading buffer, separated by 7.5% SDS-PAGE and stained by Coomassie Brilliant Blue-Plus (EBL).

Example 4: Glycopeptide Analysis by Mass Spectrometry

Two 20 μg aliquots of SARS-CoV-2 Spike protein, from Two biological replicates, were denatured in 55° C. for 1 h in 50 mM Triethylammonium bicarbonate buffer containing 10 mM of tris(2-carboxyethyl)phosphine. Next, the Spike protein were reduced and alkylated by adding 18 mM iodoacetamide (IAA) and incubated for 30 minutes in the dark. The alkylated Env proteins were digested separately using different combination of chymotrypsin or alpha lytic protease at a ratio of 1:10 (w/w), or trypsin at a ratio of 1:20(w/w). (Mass Spectrometry Grade, Promega) After an overnight digestion, the samples were dried in SpeedVac concentrator and processed for LC-MS/MS determination. Glycans categorization followed by previous study according to the composition detected and visualized by Graphpad Prism 9.0.0.

Example 5: Vaccination and Challenge Experiments

Female 6- to 7-week-old Golden Syrian Hamster (n=5) were immunized intramuscularly with 25 ug purified $S_{FG}$ or $S_{MG}$ proteins mixed with aluminum hydroxide 250 ug at day 0 and day 14. Blood was collected 28 days and 42 days after first immunization, and serum samples were collected from each hamster. Hamsters were challenged at 4 weeks after second vaccination with 1×10⁴ PFU of SARS-CoV-2 TCDC #4 (hCoV-19/Taiwan/4/2020, GISAID accession ID: EPI_ISL_411927) intranasally in a volume of 100 μL per hamster. Body weight for each hamster were recorded daily after infection. On days 3 after challenge, hamsters were euthanized by carbon dioxide. The right lung was collected for viral load determination (TCID50 assay). The left lung was fixed in 4% paraformaldehyde for histopathological examination. All animal experiments were evaluated and approved by the Institutional Animal Care and Use Committee of Academia Sinica.

Alternatively, for mice vaccination with a two-dose schedule, female 6- to 8-week-old BALB/c mice (n=5) were immunized intramuscularly with 10 μg of purified $S_{FG}$, $S_{HM}$, or $S_{MG}$ mixed with aluminum hydroxide (50 μg) at days 0 and 14. The serum was collected at day 28 after the first vaccination for evaluation of anti-S IgG abundance, IgG subtype, and neutralizing titers (described in the Supplementary Materials and Methods). The lymph nodes of $S_{FG}$- or $S_{MG}$-immunized mice were collected at day 21 after the first vaccination for T cell response analysis (described in the Supplementary Materials and Methods). For B cell repertoire analysis and serum titers against variants, female 6- to 8-week-old BALB/c mice (n=5) were immunized intramuscularly with 20 μg of purified $S_{FG}$ or $S_{MG}$ mixed with aluminum hydroxide (20 μg) at days 0, 14, and 56; mice were euthanized at day 84 to collect whole blood for anti-S IgG and neutralizing titer evaluation and spleens for sorting of S protein-specific B cells (described in the Supplementary Materials and Methods).

For hamster vaccination and virus challenge study, male 6- to 7-week-old golden Syrian hamsters (n=5) were immunized intramuscularly with 25 μg of purified $S_{FG}$ or $S_{MG}$ mixed with aluminum hydroxide (250 μg) at days 0 and 14. Four weeks after the second immunization, each hamster was intranasally challenged with 1×10⁴ $TCID_{50}$ of SARS-CoV-2 (hCoV-19/Taiwan/4/2020) in 100 μl of PBS. Body weight was recorded daily after infection. On day 3 after challenge, hamsters were euthanized by carbon dioxide. The superior lobe of the left lung was fixed in 10% paraformaldehyde for histopathological examination, and the rest of the lung was collected for viral load determination ($TCID_{50}$ assay).

For transgenic mouse vaccination and virus challenge study, male 6- to 8-week-old CAG-hACE2 transgenic mice or male 12-week-old K18-hACE2 transgenic mice (purchased from the Jackson Laboratory) were immunized intramuscularly with 10 ug of purified $S_{FG}$ or $S_{MG}$ mixed with aluminum hydroxide (50 μg) at days 0 and 14. CAG-hACE2 transgenic mice were challenged intranasally 4 weeks after the second immunization with 1×10³ $TCID_{50}$ of WT SARS-CoV-2. In the first trial (n=3), all mice were euthanized at 7 dpi for histopathological examination of superior lobe of the left lung; in the second trial (n=7), three mice were euthanized at 4 dpi for lung virus titer, and four mice were kept until 14 dpi for survival analysis. Serum was collected 1 day before virus challenge.

For challenge studies using VOCs, CAG-hACE2 mice were challenged with $1\times10^3$ $TCID_{50}$ of the alpha variant (hCoV-19/Taiwan/792/2020) (n=5) or the gamma variant (hCoV-19/Taiwan/906/2021) of SARS-CoV-2 in 50 µl of PBS per mouse. In addition, K18-hACE2 mice were challenged intranasally 4 weeks after the second immunization with $1\times10^4$ $TCID_{50}$ of the delta SARS-CoV-2 (hCoV-19/Taiwan/1144/2021) (n=4) in 50 µl of PBS per mice. For all SARS-CoV-2 variant challenge models, body weight for each mouse was recorded daily until 14 dpi.

For prophylactic protection test of antibody, male 8-week-old K18-hACE2 transgenic mice (n=3) were injected intraperitoneally with m31A7 (15 mg/kg) or PBS 1 day before being intranasally challenged with $1\times10^3$ $TCID_{50}$ of WT SARS-CoV-2 (hCoV-19/Taiwan/4/2020). Body weight and body temperature were recorded daily until 5 dpi. All animal experiments were evaluated and approved by the Institutional Animal Care and Use Committee of Academia Sinica (approval nos. 21-10-1716, 18-12-1272, and 20-10-1522).

Example 6: Histology and Immunohistochemistry (IHC) Staining

Hamster lungs at 3 dpi were immediately collected and placed in 10% neutral buffered formalin fixation for 24 h, then transferred into 70% ethanol for 72 hours. Paraffin-embedded lungs tissue was trimmed to the thickness of 5 mm. For histological staining, tissue was stained with hematoxylin and eosin (H & E). For immunohistochemistry (IHC) staining, the tissue sectioned were deparaffinized with xylene and rehydrated with ethanol gradient. Antigen retrieval was performed by heating the slides to 95° C. for 10 minutes in 10 mM sodium citrate buffer (pH 6.0) in a microwave oven. After cooling at room temperature and washing with PBS, 3% $H_2O_2$ apply to eliminate endogenous peroxidase activity. The tissue sectioned were blocking with 5% normal goat serum and 1% BSA in 1×PBST for 1 hour, followed by incubation with rabbit anti-N and anti-S primary antibodies at 1:50 dilution (Anti-SARS-CoV-2 polyclonal antibody) overnight at 4° C. Then the tissue was incubated with goat anti-rabbit HRP secondary antibody at 1:500 dilutions for 1 hour and visualized by incubation with 3,3-diaminobenzidine (DAB) substrate and counterstained with hematoxylin.

Example 7: Immunofluorescence (IF) Staining

For immunofluorescence staining, after antigen retrieval steps, tissue was permeabilized with Triton X-100 in PBS. The tissue sectioned were blocking with 5% normal goat serum and 1% BSA in 1×PBST for 1 hour. Then, incubated with an autofluorescence quencher for 5 minutes. The samples were subsequently incubated with rabbit anti-N and anti-S primary antibodies at 1:50 dilution (Anti-SARS-CoV-2 polyclonal antibody) overnight at 4° C., secondary antibody Alexa Fluor-488 (1:500, Thermo Fisher™) for 1 hour at room temperature, and 4,6-diamidino-2-phenylindole (DAPI), a nuclear dye for 3 minutes at room temperature. The coverslips were mounted on microscope slides and imaged under a Leica TCS SP8X confocal microscope with HC PL APO CS2 10×/1.40 lens (Leica AG, Wetzlar, Germany).

Example 8: Transgenic Mice Vaccination and Challenge Experiments

Male 8-week-old CAG-hACE2 transgenic mice (n=3) were immunized intramuscularly with 10 ug purified $S_{FG}$ or $S_{MG}$ proteins mixed with aluminum hydroxide 50 ug at day 0 and day 14.[14] Blood was collected 28 days and 42 days after first immunization, and serum samples were collected from each transgenic mouse. Hamsters were challenged at 6 weeks after second vaccination with $1\times10^3$ PFU of SARS-CoV-2 TCDC #4 (hCoV-19/Taiwan/4/2020, GISAID accession ID: EPI_ISL_411927) intranasally in a volume of 100 µL per mice. Body weight and survival rate for each transgenic mice were recorded daily after infection. On days 7 after challenge, all transgenic mice were euthanized by carbon dioxide. The lung was fixed in 4% paraformaldehyde for histopathological examination. All animal experiments were evaluated and approved by the Institutional Animal Care and Use Committee of Academia Sinica.

Example 9: Quantification of Viral Titer in Lung Tissue by Cell Culture Infectious Assay (TCID50)

The middle, inferior, and post-caval lung lobes of hamsters were homogenized in 600 µl of DMEM with 2% FBS and 1% penicillin/streptomycin using a homogenizer. Tissue homogenate was centrifuged at 15,000 rpm for 5 minutes and the supernatant was collected for live virus titration. Briefly, 10-fold serial dilutions of each sample were added onto Vero E6 cell monolayer in quadruplicate and incubated for 4 days. Cells were then fixed with 10% formaldehyde and stained with 0.5% crystal violet for 20 minutes. The plates were washed with tap water and scored for infection. The fifty-percent tissue culture infectious dose (TCID50)/mL was calculated by the Reed and Muench method.

Example 10: Mice Vaccination Studies

Female 6- to 8-week-old BALB/c mice (n=5) were immunized intramuscularly with 20 ug purified $S_{FG}$ or $S_{MG}$ proteins mixed with aluminum hydroxide 20 ug at day 0, day 14 and day 56. Blood was collected 14 days after third immunization, and serum samples were collected from each mouse. All animal experiments were evaluated and approved by the Institutional Animal Care and Use Committee of Academia Sinica.

Example 11: Sera Antibody Titer Evaluation

Anti-S ELISA were used to determine sera IgG titer. Plates were blocked with 5% skim milk, and mouse polyclonal anti-S primary antibody and HRP-conjugated secondary antibody were sequentially added. Peroxidase substrate solution (TMB) and 1M $H_2SO_4$ stop solution were used and absorbance (OD 450 nm) read by a microplate reader. Tested strain included SARS-CoV-2 (wild type, variants B.1.1.7 and B.1.135), RnGT13, and SARS-CoV-1.

m31A7 antibody was isolated by single B cell screening assay and then characterized. Primers were designed on the basis of a previous publication (T. Tiller, C. E Busse, H. Wardemann, Cloning and expression of murine Ig genes from single B cells. *J. Immunol. Methods* 350, 183-193 (2009)). Polymerase chain reaction (PCR) was performed at 50° C. for 30 min, 95° C. for 15 min, followed by 40 cycles of incubation at 94° C. for 30 s, 50° C. for 30 s, and 72° C. for 1 min, with a final extension at 72° C. for 10 min. Seminested second-round PCR was performed using KOD One PCR master mix (TOYOBO) with 1 µl of unpurified first-round PCR product at 98° C. for 2 min, followed by 45 cycles of incubation at 98° C. for 10 s, 55° C. for 10 s, and 68° C. for 10 s, with a final extension at 68° C. for 1 min. PCR products were then analyzed by electrophoresis and sequencing. The Ig V and L genes were identified on the international ImMunoGeneTics information system. Genes were then amplified from second-round PCR product with single gene-specific V and L gene primers containing restriction sites for cloning into the vectors containing human IgH or IgL expression backbone. The chimeric IgH and IgL expression constructs were cotransfected into Expi293 for antibody production. After m31A7 was isolated, the antibody was subsequently evaluated for S protein binding by ELISA and fluorescence-activated cell sorting, pseudovirus neutralization potency, binding kinetics, epitope mapping, and structure determination.

Example 12: Pseudovirus Neutralization Assay

To determine the infectious units of pseudotyped lentiviral vectors, we seeded 293T-ACE2 cells at appropriate density in 96-well (100 µL per well) tissue culture plates 1 day prior to infection. After incubate overnight (37° C., 5% $CO_2$), 100 mL three premixed pseudovirus supernatant and four-fold serial dilutions of immunized mouse sera were added in the plated cells. Cells were incubated for 48 h at 37° C./5% $CO_2$ to allow for expression of Nano-Luciferase reporter gene. Luciferase activities were measured by the ELISA reader. Percent inhibition was calculated by the following equation $100*[1-(RLU_{sample}/RLU_{mock-treatment})]$. Data was analyzed using Graphpad Prism and pNT50 values were calculated by taking the 50% inhibitory concentration value for all samples.

Example 13: Plaque Reduction Assays

Vero E6 cells were seeded into 24-well culture plates in DMEM with 10% FBS and antibiotics 1 day before infection. SARS-CoV-2 was incubated with antibodies for 1 h at 37° C. before adding to the cell monolayer for another hour. Subsequently, virus-antibody mixtures were removed, and the cell monolayer was washed once with PBS before covering with media containing 1% methylcellulose for 5-7 days. The cells were fixed with 10% formaldehyde overnight. After removal of the overlay media, the cells were stained with 0.7% crystal violet, and the plaques were counted. The percentage of inhibition was calculated as $[1-(VD/VC)] \times 100\%$, where VD and VC refer to the virus titers in the presence and absence of the sera, respectively.

For CPE-Based neutralization assay, Vero E6 cells were plated onto a 6-well plate at $2 \times 10^5$ cells/well overnight for 90% confluence. Serum and viruses were mixed before added onto the monolayer for another hour. The plates are allowed to solidify at room temperature for 30 minutes, then incubated at 37° C. until cytopathic effects (CPE) are observed.

Statistical analysis: All of the data are expressed as the means±standard errors of the means. For all of the analyses, P values were obtained from Student's t-test (unpaired, two tailed) except for the curve comparison using Student's t-test (paired, two tailed) tests. All of the graphs were generated with GraphPad Prism version 9.0.0 software.

Example 14: Design and Characterization of Glycoengineered Mono-GlcNAc-Decorated Spike ($S_{MG}$) Protein Vaccine The recombinant native with the sequence (amino acid 14-1209) from the original SARS-CoV-2 Wuhan strain (hCoV/Wuhan/WH01/2019) was codon optimized for human cell expression, with GSAG (SEQ ID NO: 9) residues to replace the original furin cleavage site and 2 proline mutation to fix the spike native in its prefusion state, and at its C-terminus added a foldon trimerization sequence and a His-tag, and expressed with human HEK293S cells (FIG. 1). The intermediate high-mannose type spike recombinant native ($S_{HM}$) where all the N-glycans, indicated by branch sign (FIG. 1a), are of the Man5 N-glycans was first obtained and purified. Endoglycosylase EndoH was then used to removed excess glycans and to generate the end product monoglycosylated Spike native (FIG. 1b). The purified $S_{MG}$ is a trimer with an apparent molecular weight of ~520 kDa in solution and high purity (FIGS. 1c and 1d). The reduction in size due to removal of N-glycans was analyzed by SDS-PAGE, compared with the ordinary $S_{FG}$ and intermediate $S_{HM}$ (FIG. 1d). A mass spectrometry analysis on the $S_{MG}$ indicated that most of the N-glycosylation sites are with near 100% single sugar, N-acetylglucosamine (GlcNAc), with the exception of N603 and N1194 that the GlcNAc is >90% (FIG. 1f). In contrast, the original fully glycosylated Spike native has heterogeneous N-glycans on all its N-glycosylation sites containing complex type, hybrid type and others.

Figure 2:
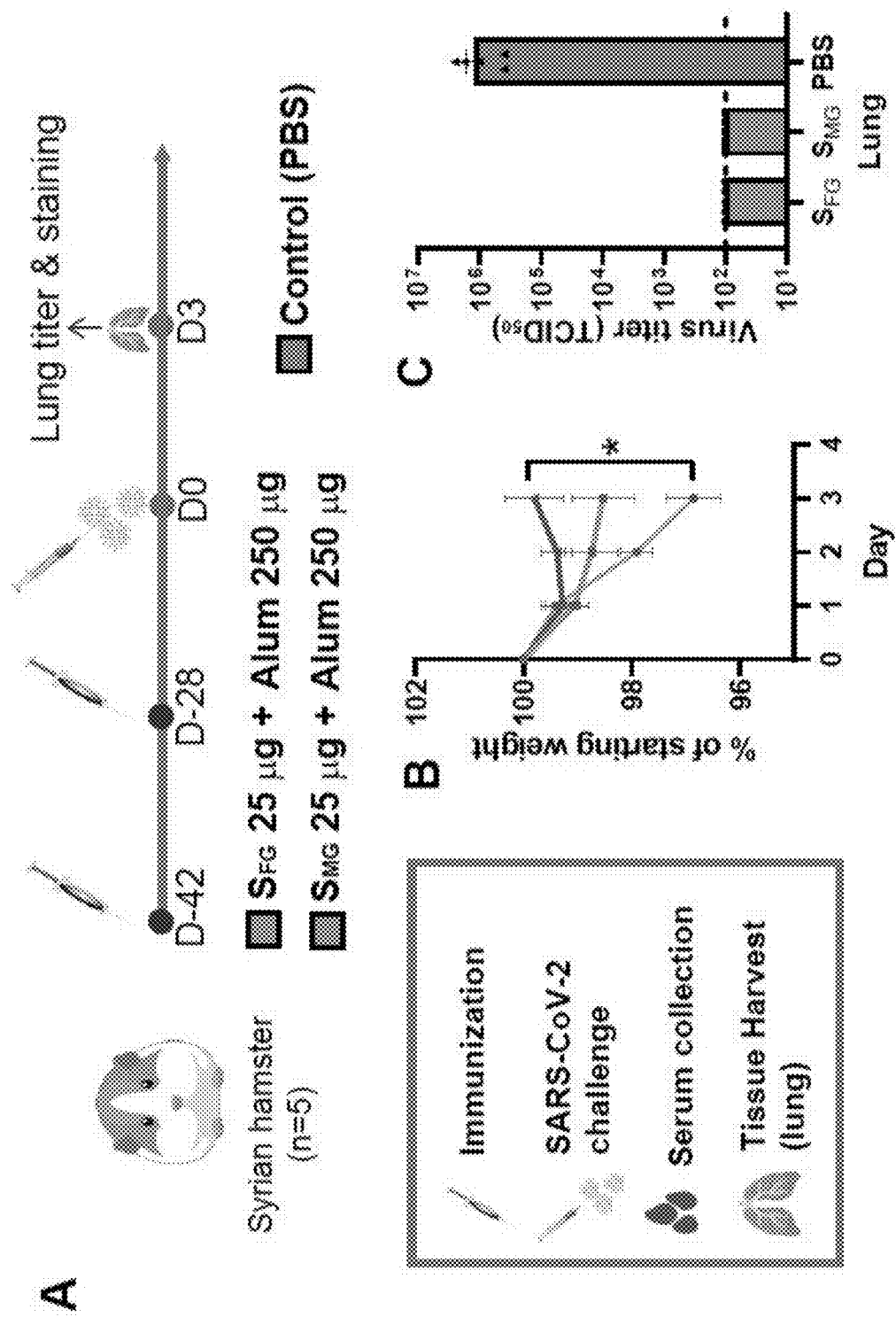
FIGS. 2 (A) to (S). $S_{MG}$ vaccination provides enhanced protection against SARS-CoV-2 infection in vivo. (A) The immunization schedule for Syrian hamsters is shown. $S_{FG}$ (blue), $S_{MG}$ (red), and control (gray). (B) Weight change was measured in Syrian hamsters after WT SARS-CoV-2 challenge. (C) Lung virus titers of challenged hamsters are shown. The dashed line indicates the lower limit of detection. (D) Representative images shown histopathology, immunohistochemistry, and immunofluorescence of the lungs from an infected hamster (3 dpi). First row: Hematoxylin and eosin (H&E) staining; scale bar, 50 μm. Second row: Immunohistochemistry (IHC) staining; scale bar, 50 μm. Third row: Immunofluorescence (IF) staining; scale bar, 100 μm. SARS-CoV-2 N-specific polyclonal antibodies were used for virus detection as brown dots in IHC and green dots in IF staining. Blue: 4,6-diamidino-2-phenylindole (DAPI). (E) The immunization schedule for CAG-hACE2 or K18-hACE2 transgenic mice is shown. (F to I) Anti-S IgG titers (F), SARS-CoV-2 WT microneutralization titers (G), and subtype IgG analysis, including IgG1, IgG2c (H), and IgG2c:IgG1 ratio (I), are shown for serum samples collected from immunized CAG-hACE2 transgenic mice (n=7). (J) Representative histopathology, immunohistochemistry, and immunofluorescence of the infected mouse lungs (7 dpi) are shown. Scale bars are the same as in (D). (K) Lung virus titers of the infected CAG-hACE2 mice (n=3). The dashed line indicates the lower limit of detection. (L and M) Weight change (L) and survival analysis (M) are shown for WT-SARS-CoV-2-challenged CAG-hACE2 transgenic mice (n=4). (N and O) Weight change (N) and survival analysis (O) are shown for SARS-CoV-2 alpha variant-challenged CAG-hACE2 transgenic mice (n=5). (P and Q) Weight change (P) and survival analysis (Q) are shown for SARS-CoV-2 gamma variant-challenged CAG-hACE2 transgenic mice (n=5). (R and S) Weight change (R) and survival analysis (S) are shown for SARS-CoV-2 delta variant-challenged K18-hACE2 transgenic mice (n=4). Data are shown as means±SEM and analyzed by two-sided Mann-Whitney U tests to compare two experimental groups. ns, not significant; *P<0.05.
Figure 2:
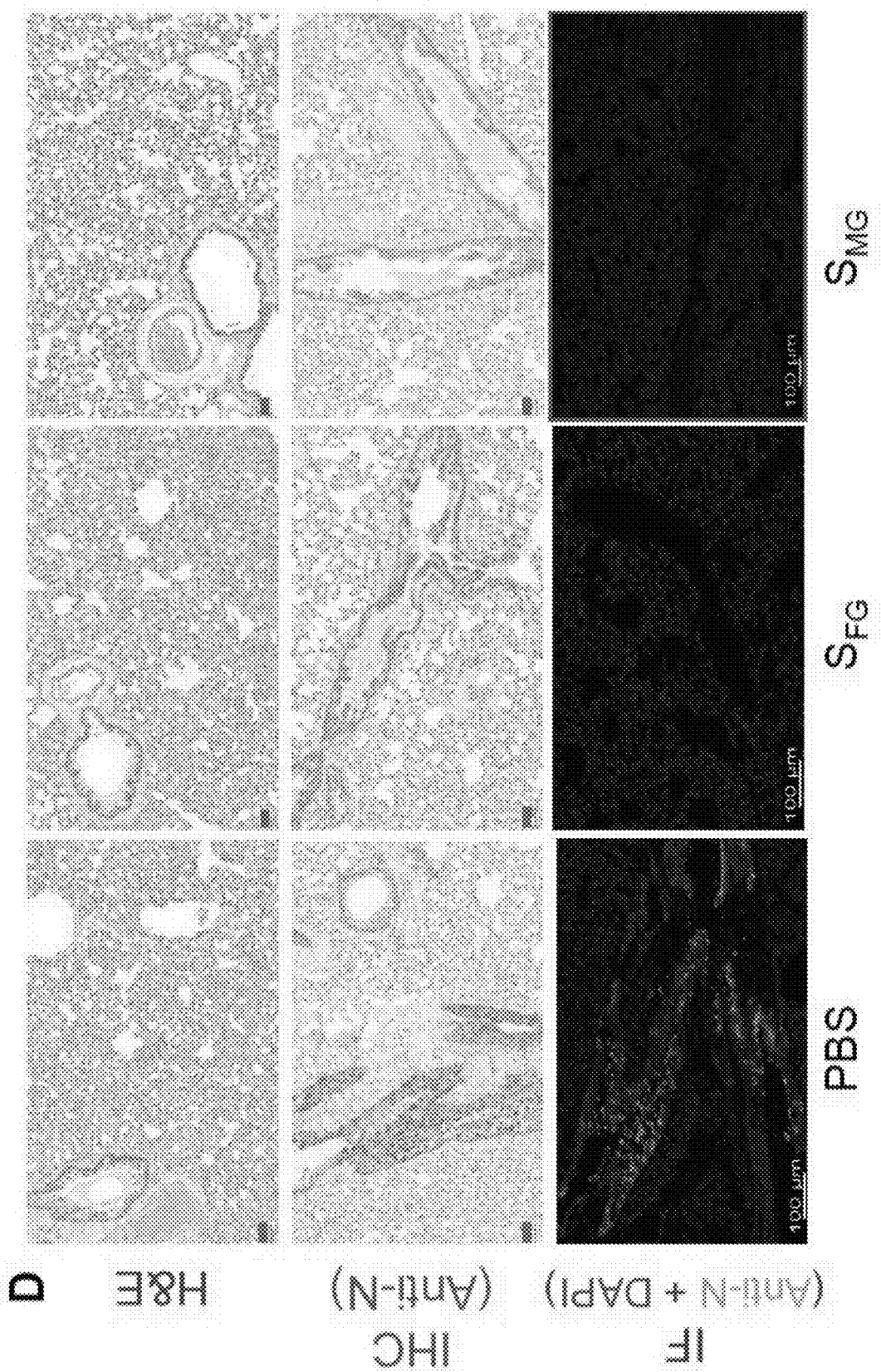
Figure 2:
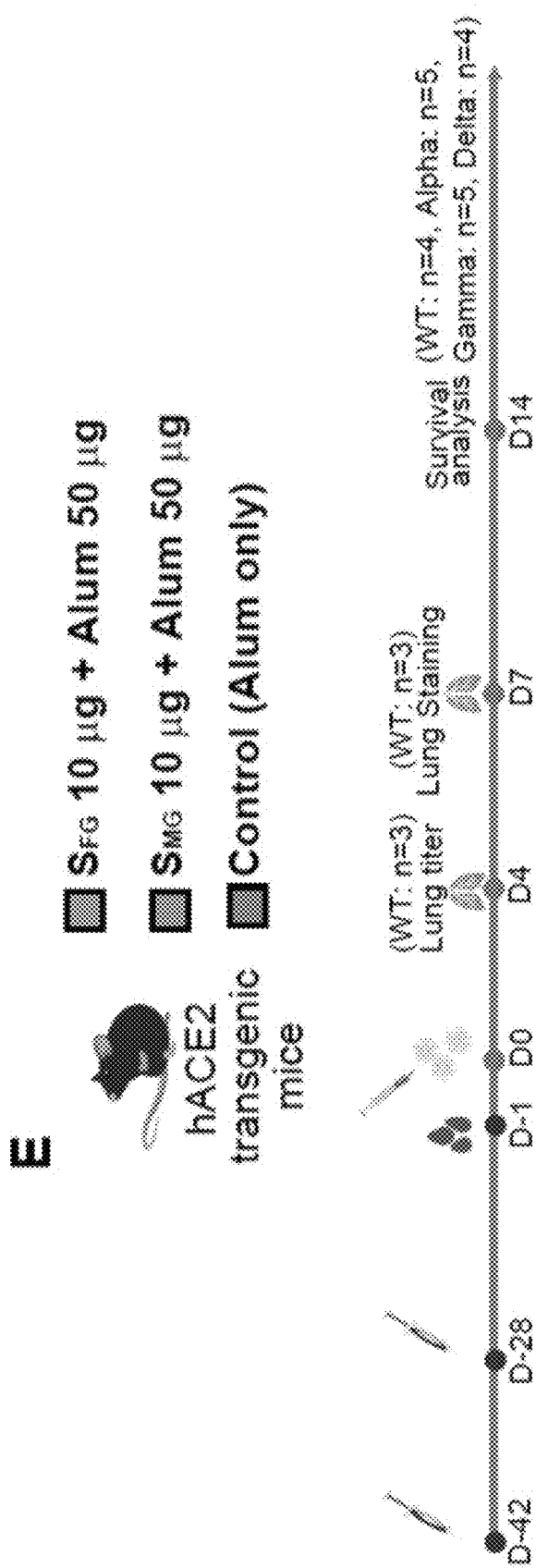
Figure 2:
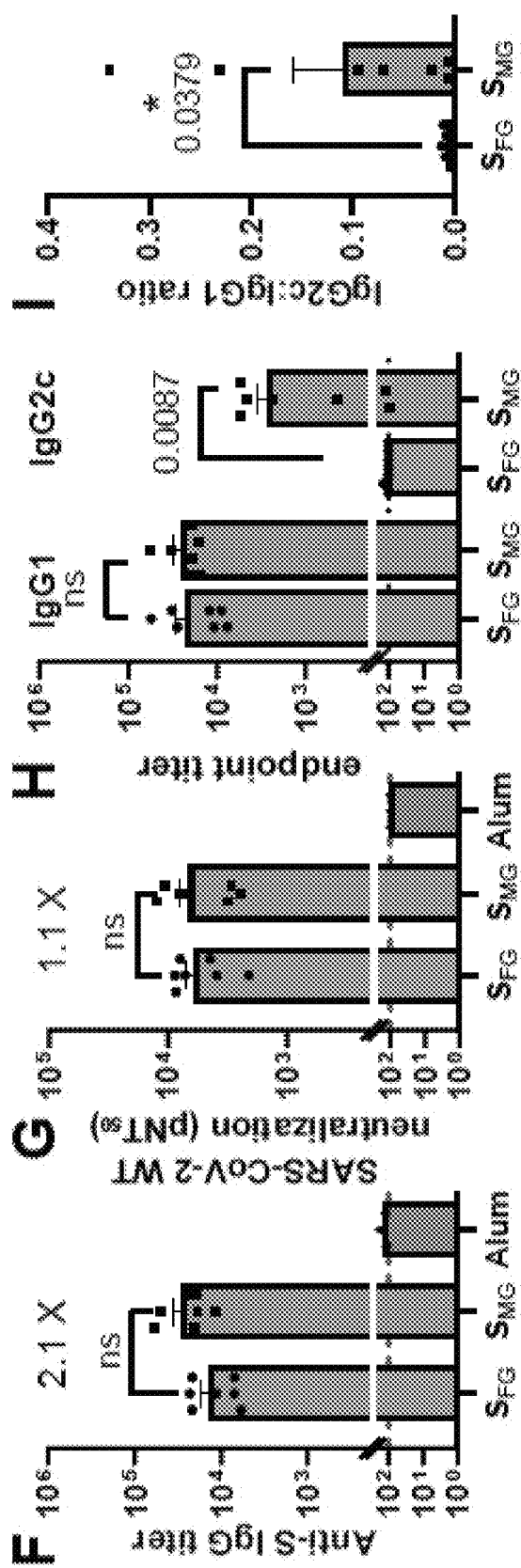
Figure 2:
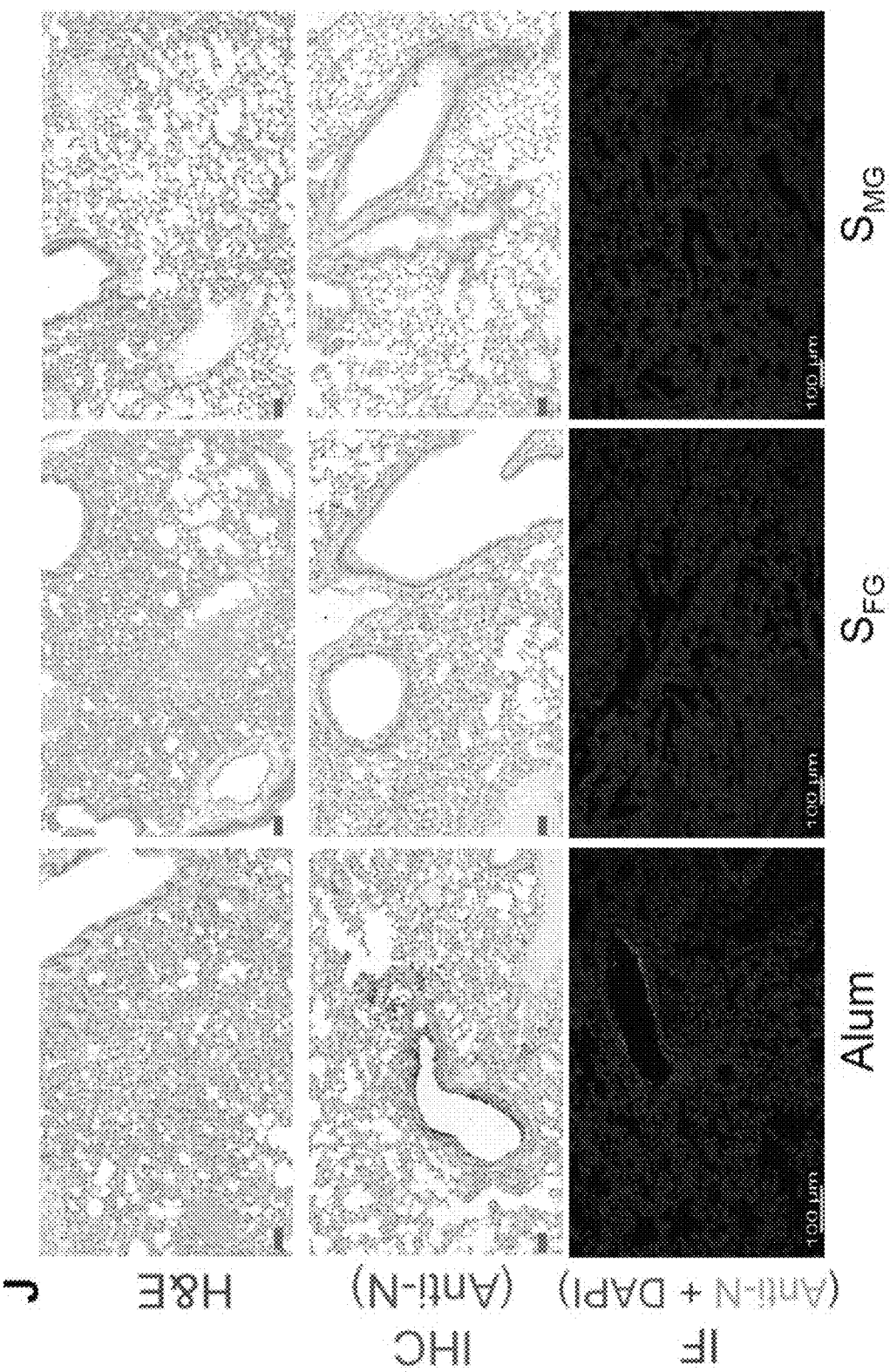
Figure 2:
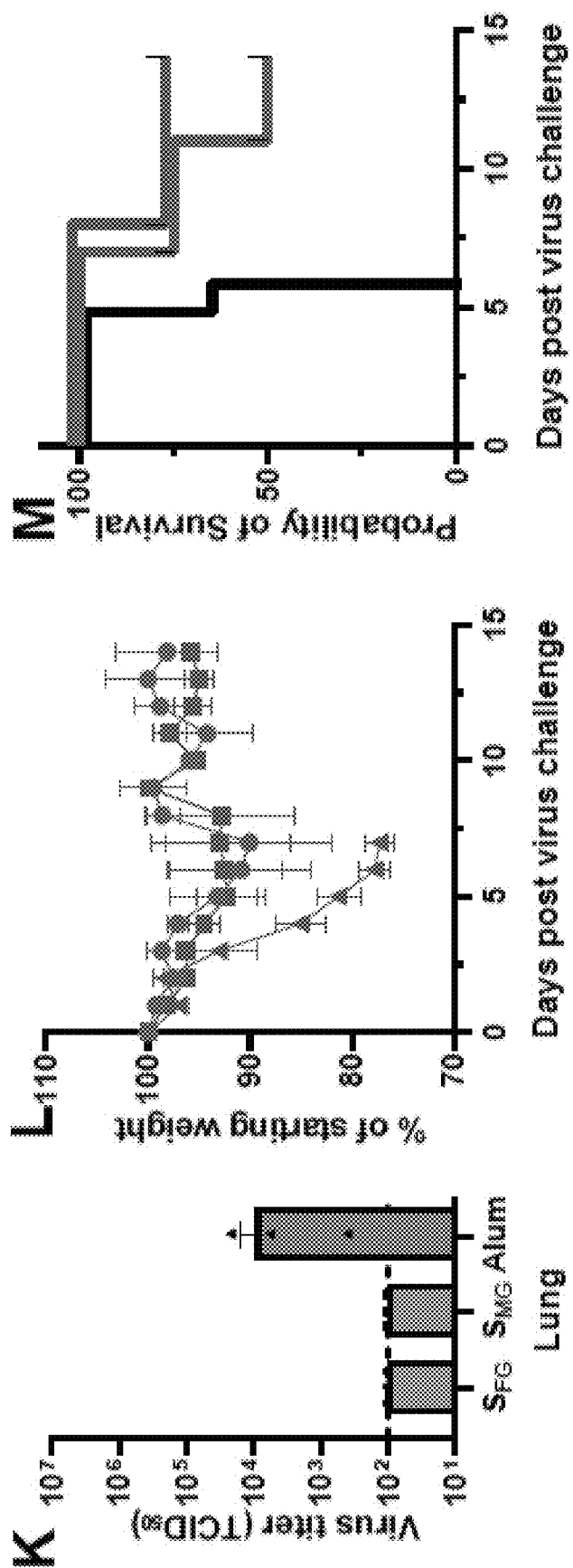
Figure 2:
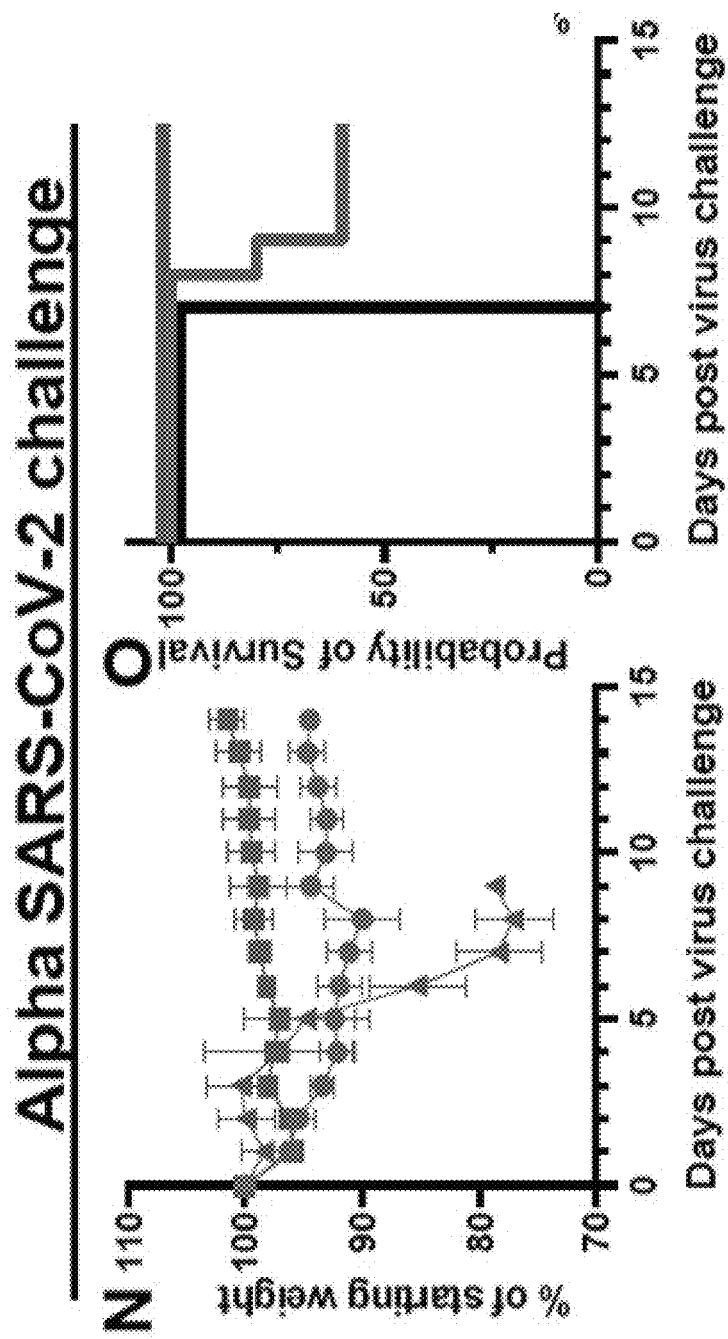
Figure 2:
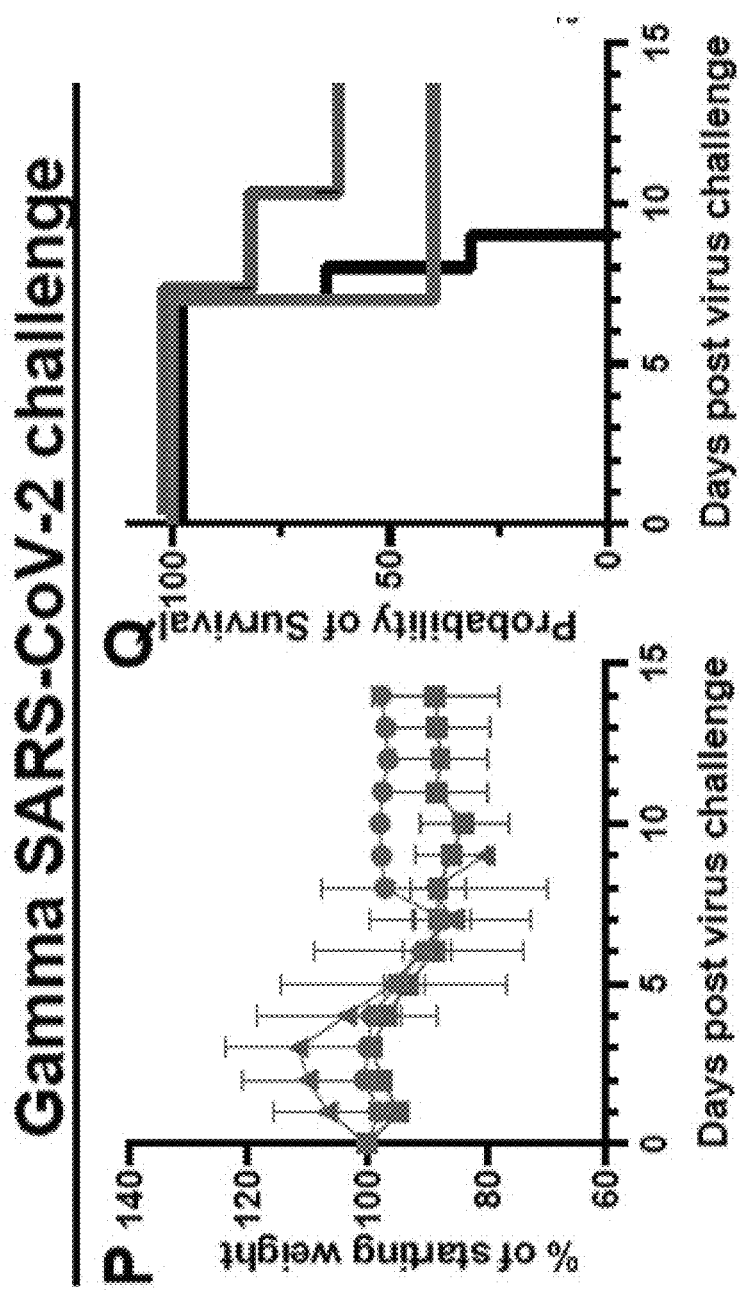
Figure 2:
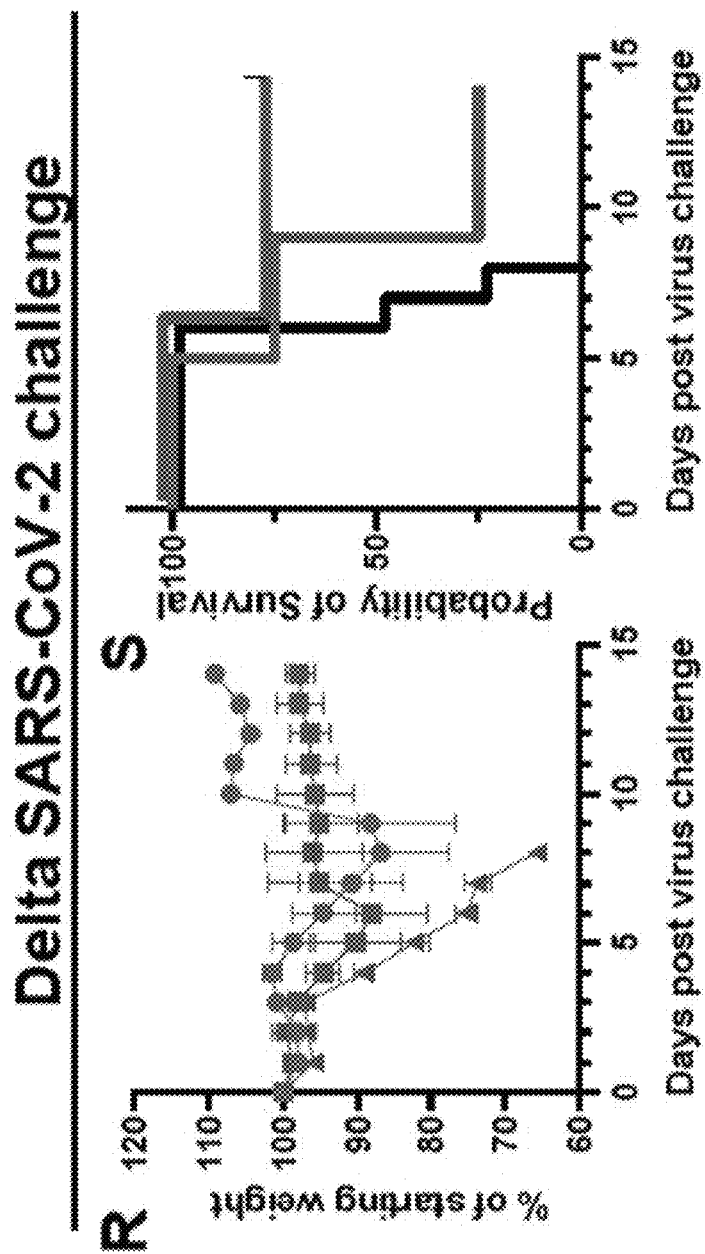
Figure 6:
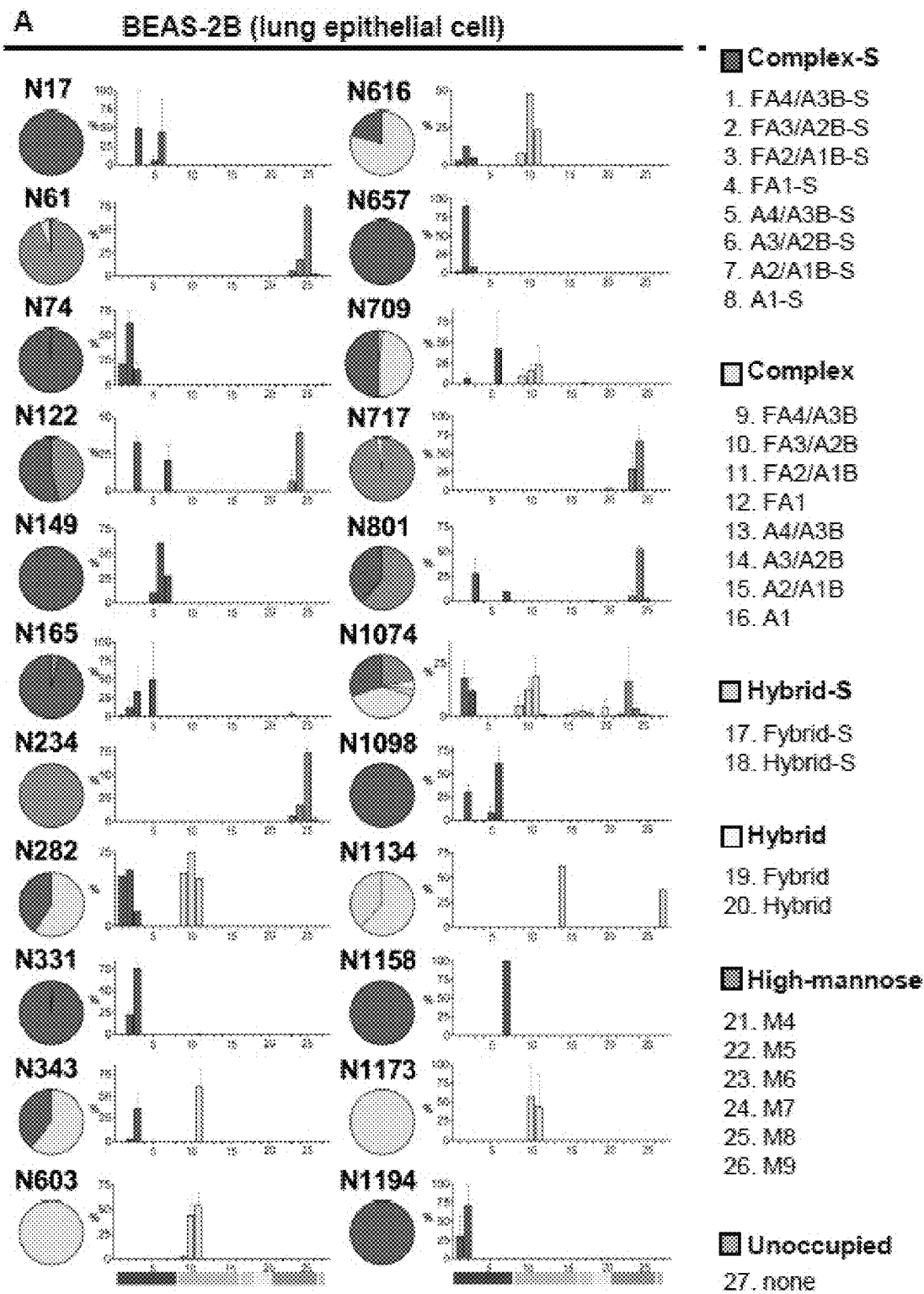
FIGS. 6 (A) to (E). S protein glycan profiles demonstrate differences in two cell lines and correlate with sequence conservation. (A and B) A comparison of the N-glycosylation profile of recombinant S protein expressed from BEAS-2B lung epithelial cells (A) and HEK293T kidney epithelial cells (B) is shown. Glycans are grouped and colored accordingly: complex-S (sialylated complex type; dark blue), complex (non-sialylated complex type; light blue), hybrid-S (sialylated hybrid type; dark yellow), and hybrid (nonsialylated hybrid type; light yellow), high mannose (green), and unoccupied (gray). The percentage of each group is shown for each glycosite in a pie chart, and the proportion of each glycoform (nos. 1 to 27) in a bar chart. The bar graphs represent the means±SD of three biological replicates. Fhybrid indicates fucosylated hybrid-type glycans. (C) Glycan profiles from (A) and (B) were mapped on the 3D structure of S ectodomain (modeled from 6VSB). Glycans are colored by the highest-abundance group for BEAS-2B (left) or HEK293T (right) data as labeled (complex type, blue; hybrid type, yellow; and high mannose, green). Non-complex-type N-glycosites are labeled with residue number. (D) Mapping of relative surface accessibility (RSA) on modeled S structure protein is shown, with buried residues colored in dark yellow, glycan shielded in yellow, and exposed in light yellow. (E) Mapping of sequence variation on modeled S protein structure is shown, colored in a heatmap, with darker red indicating higher mutation rates. Several highly conserved glycan-shielded regions are highlighted. More details for (D) and (E) can be found in FIG. S9 and data file S1.
Figure 6:
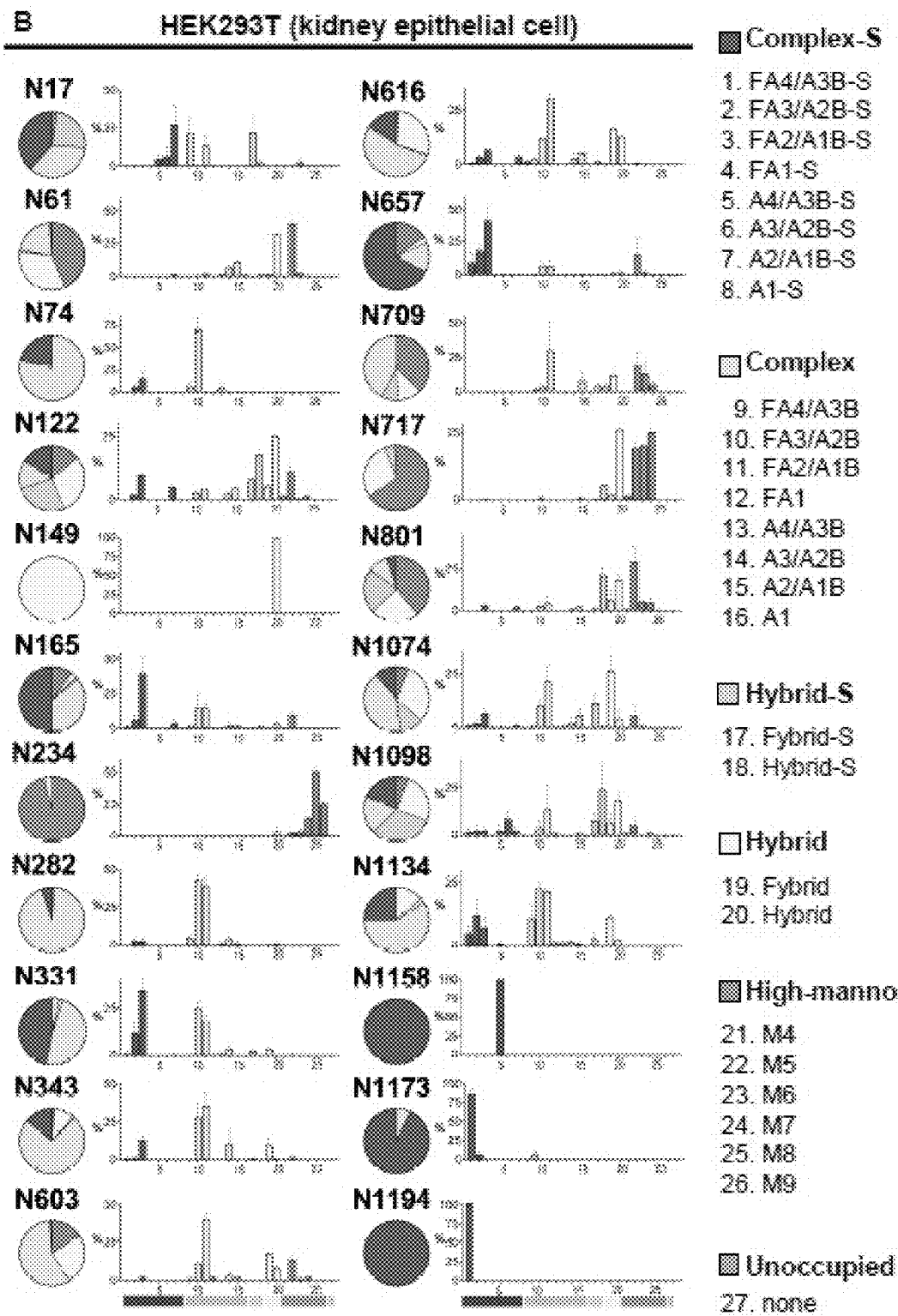
Figure 6:
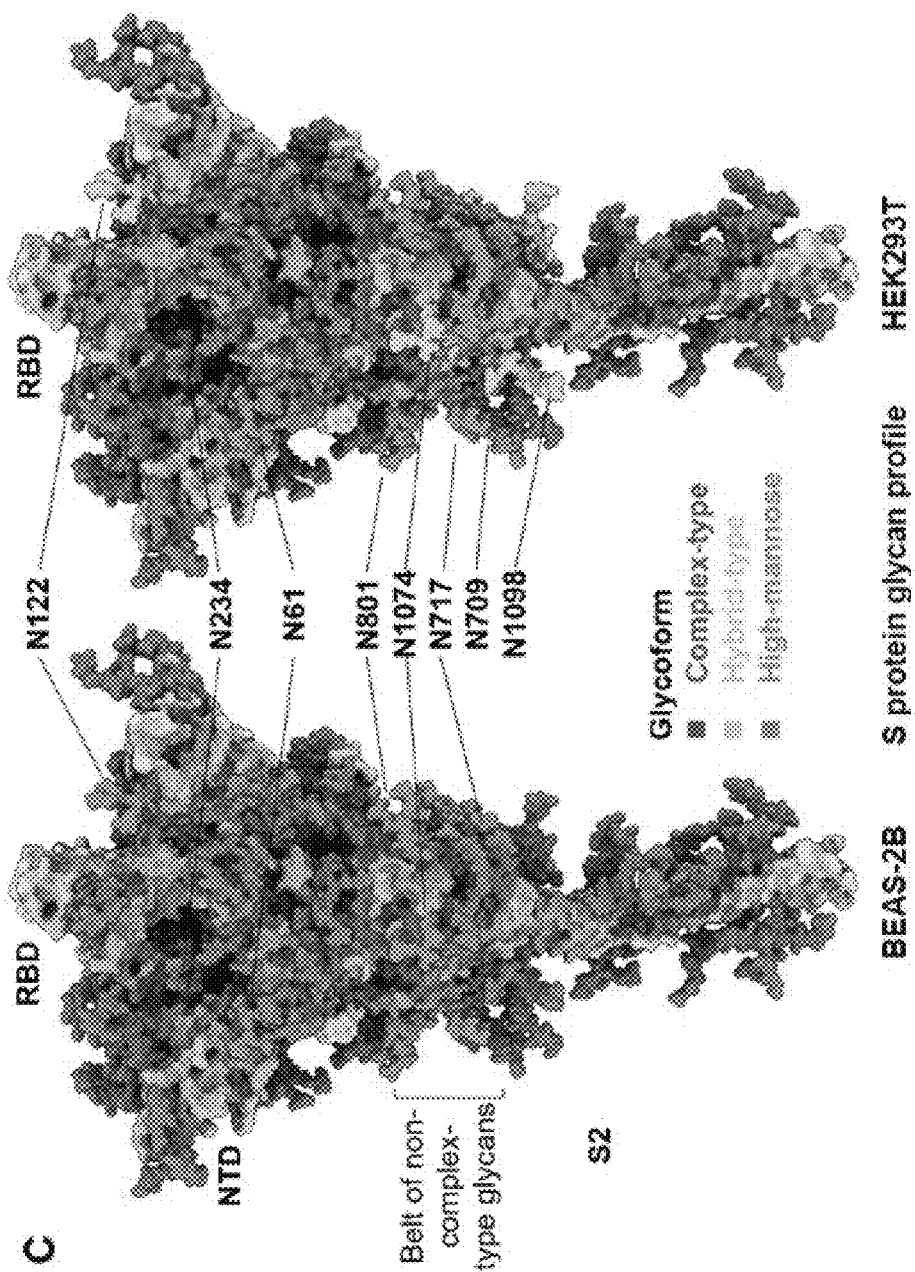
Figure 6:
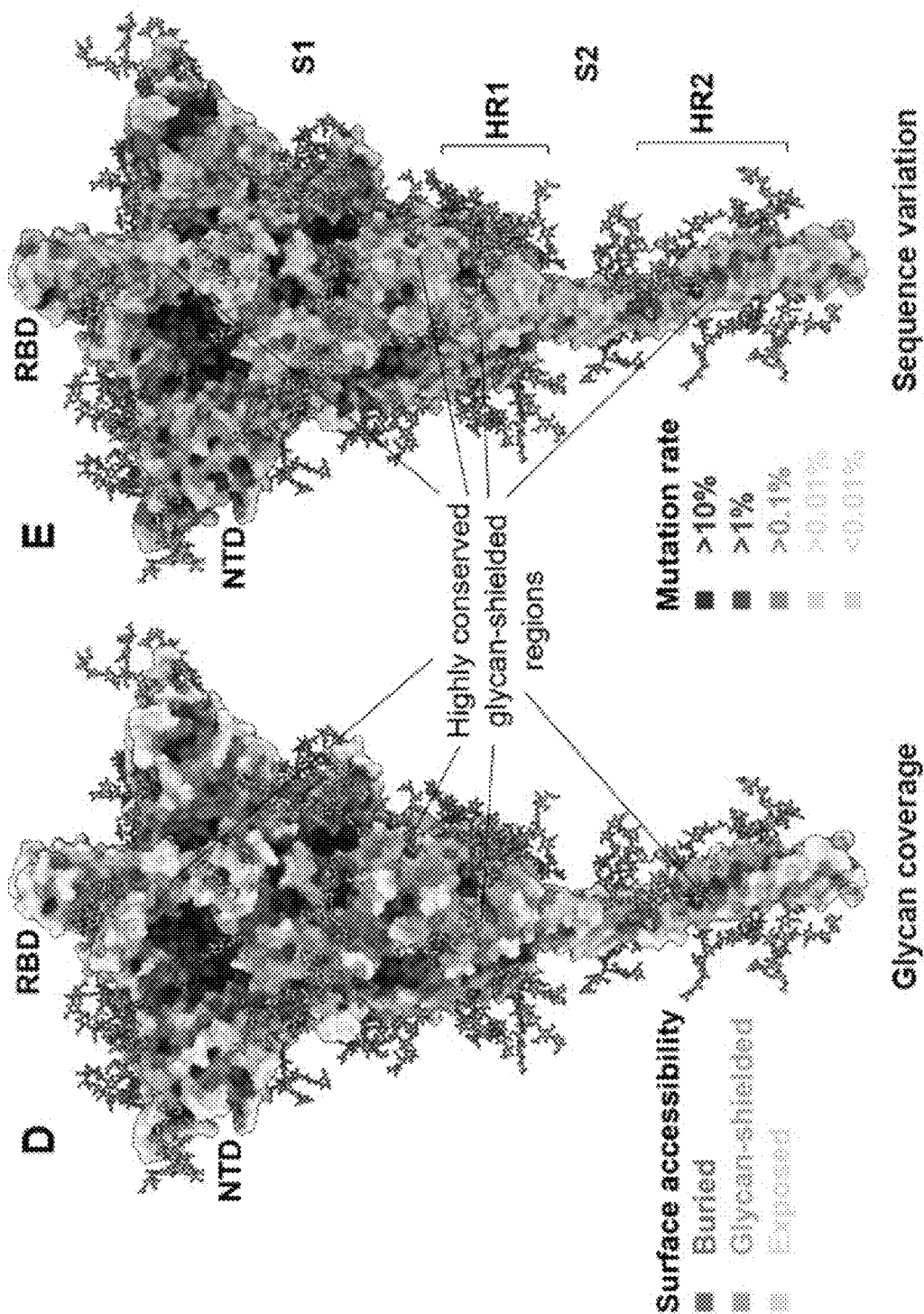

Example 15: $S_{MG}$ Vaccine Provided Superior Protection Against SARS-CoV-2 and Variants In Vivo To evaluate the in vivo protective efficacy of $S_{MG}$ vaccine against SARS-CoV-2, we first carried out WT SARS-CoV-2 challenge in Syrian hamsters vaccinated with $S_{MG}$ or $S_{FG}$ (FIG. 2A). $S_{MG}$-vaccinated hamsters (n=5) showed less reduction in body weight as compared with the $S_{FG}$ and phosphate-buffered saline (PBS) groups (FIG. 2B), whereas similar virus titer reductions were observed in the lungs of both $S_{FG}$- and $S_{MG}$-vaccinated hamsters (FIG. 2C). In addition, according to histopathological staining and anti-nucleocapsid (N) protein immunostaining data, fewer lesions were observed in the lungs of immunized hamsters (FIG. 2D). Because hamsters only showed mild to moderate sickness upon SARS-CoV-2 infection, we then used severe disease models, the highly susceptible CAG-hACE2 (C.-Y. Tsai, C.-Y. Chen, J.-T Jan, Y.-C. Chou, M.-L. Chang, L. A. Lu, P.-Y. Huang, M F. C. Chu, T.-T Hsu, Y.-P. Hsueh, *Sex-biased response to and brain cell infection by SARS-CoV-2 in a highly susceptible human ACE2 transgenic model*. bioRxiv, 2021) or K18-hACE2 (E. S. Winkler, A. L. Bailey, N. M Kafai, S. Nair, B. T McCune, J. Yu, J. M Fox, R. E. Chen, J. T Earnest, S. P. Keeler, J. H. Ritter, L.-I. Kang, S Dort, A. Robichaud, R. Head, M J. Holtzman, M S. Diamond, *SARS-CoV-2 infection of human ACE2-transgenic mice causes severe lung inflammation and impaired function*. Nat. Immunol. 21, 1327-1335 (2020) transgenic mice (FIG. 2E). The analysis of anti-S IgG binding titer, neutralizing titers, anti-S subtype IgG, and IgG2c:IgG1 ratio (FIG. 2, F to I) in CAG-hACE2 mice all showed similar results to the BALB/c mice (FIG. 6, C to G). Following challenge with WT SARS-CoV-2 intranasally, virus was not detectable in the lungs of both $S_{FG}$- and $S_{MG}$-vaccinated CAG-hACE2 mice (n=3) by anti-N staining at 7 days postinfection (dpi) (FIG. 2J) or median tissue culture infectious dose ($TCID_{50}$) assay at 4 dpi (FIG. 2K), whereas a viral titer of over 1,000 $TCID_{50}$ was observed in the control group (FIG. 2K). The $S_{MG}$ group (n=4) exhibited better (75%) survival rate than the $S_{FG}$ (50%) at 14 dpi (FIG. 2, L and M). We then evaluated the degree of protection conferred by $S_{MG}$ vaccination against challenge with the alpha variant in CAG-hACE2 mice (n=5). We found that $S_{MG}$ vaccination provided 100% survival rate until 14 dpi (FIG. 2, N and O). $S_{MG}$-vaccinated mice also showed a 60% survival rate in the gamma variant challenge in CAG-hACE2 mice (n=5) (FIG. 22 P and Q) and a 75% survival rate in the delta variant challenge in K18-hACE2 mice (n=4) (FIG. 4, R and S), whereas less than 50% $S_{FG}$-vaccinated mice survived until 14 dpi in the gamma and delta variant challenge (FIG. 2, Q to S). The improved in vivo protection conferred by $S_{MG}$ vaccination provides further evidence that removal of glycan shields from an immunogen is an advantageous strategy to elicit superior immune response.

Figure 3:
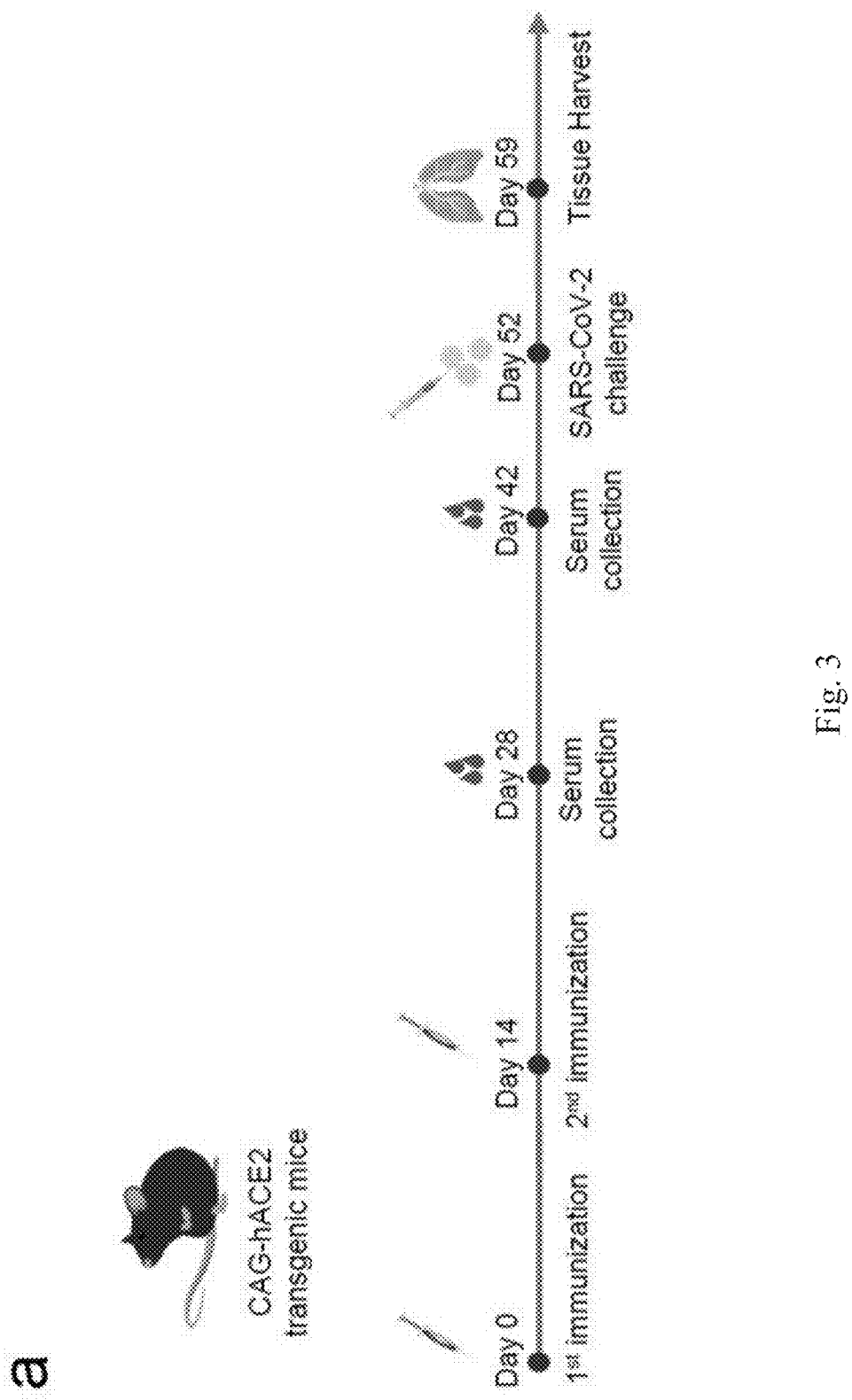
FIGS. 3 (a) to (e). $S_{MG}$ vaccination provides better protection against a lethal dose SARS-CoV-2 infection in transgenic hACE2 mice. (a) Transgenic mice immunization and challenge schedule. (b) Sera collected at 28 days and 42 days post initial vaccination were examined for anti-Spike specific IgG. (c) Sera collected at 42 days post initial vaccination were examined for neutralizing antibody titer by CPE assay (d) Transgenic mice weight change after challenge. (n=3) (e) Transgenic mice survival rate after challenge. (n=3). Data are means±SEM (standard error of the mean). Comparisons were performed by Student's t-test (unpaired, two tailed). The binding and neutralization fold increases of the antibody elicited by $S_{MG}$ over $S_{FG}$ vaccines are indicated by numbers above the bars. Blue squares, transgenic mice immunized with $S_{FG}$; Red triangles, transgenic mice immunized with $S_{MG}$; Gray dots, Control group animals (Alum only group).
Figure 3:
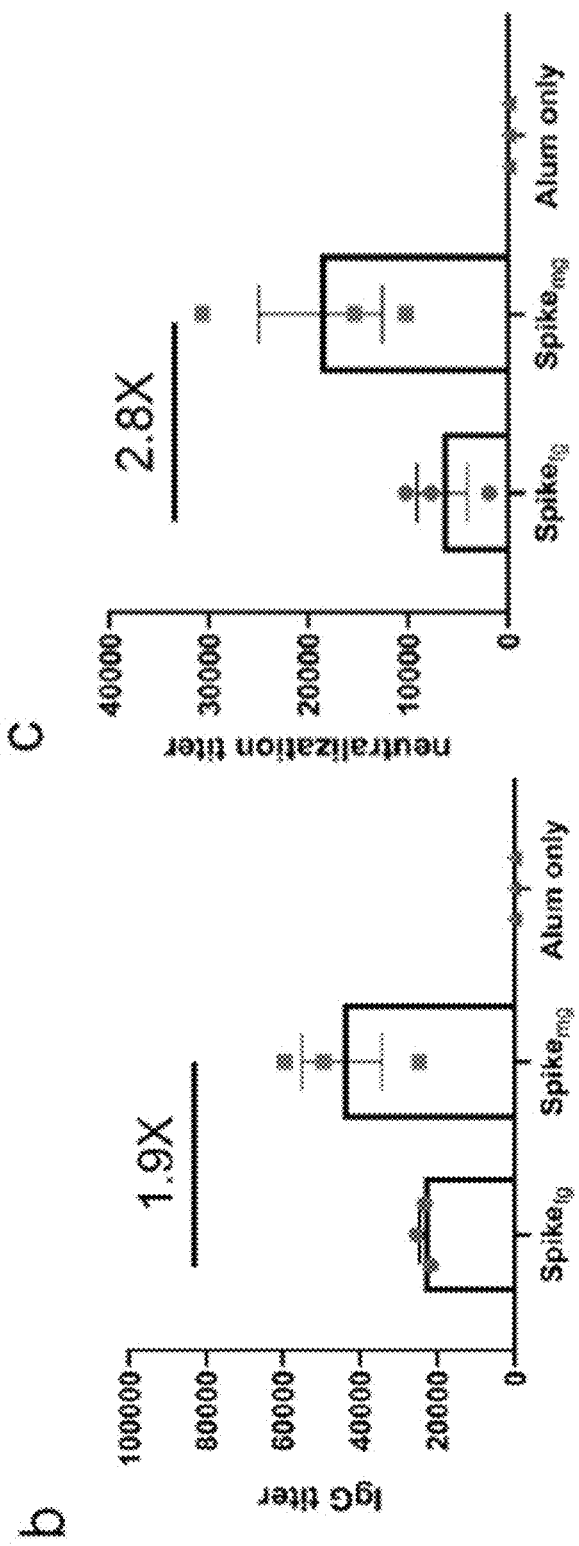
Figure 3:
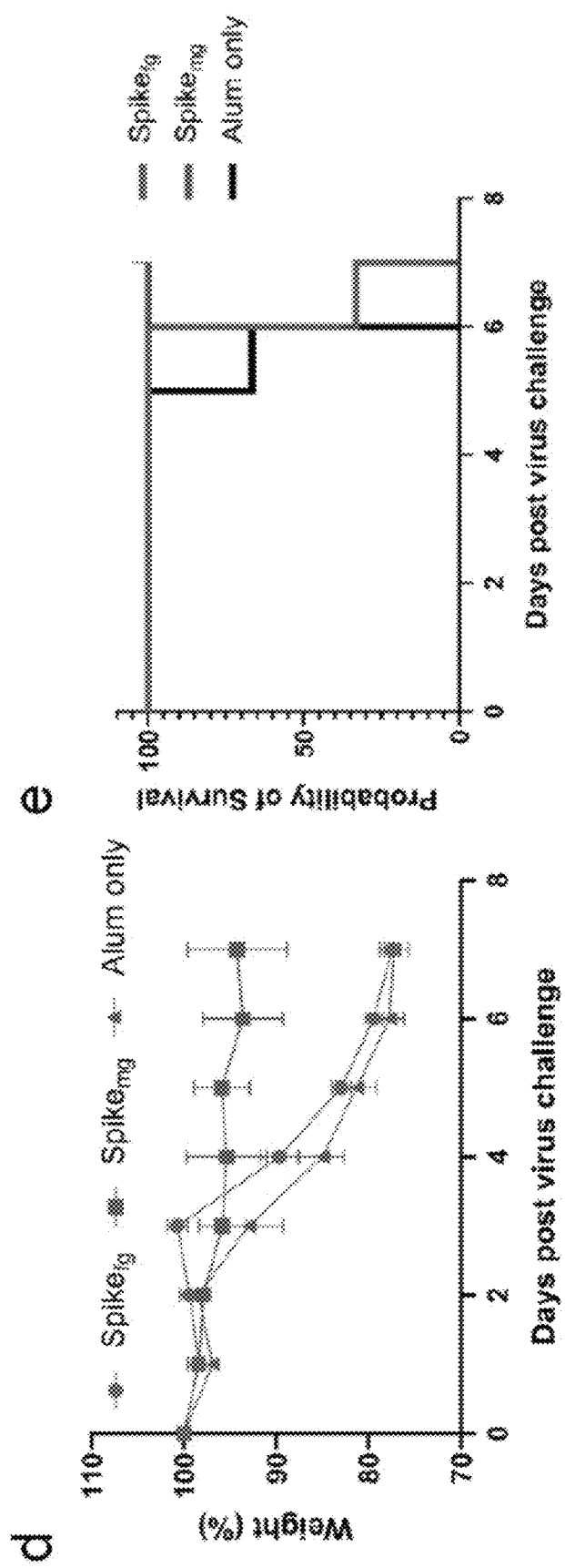

Example 16: $S_{MG}$ Vaccination Provides Better Protection Against a Lethal Dose SARS-CoV-2 Infection in Transgenic hACE2 Mice The CAG-hACE2 transgenic mice can develop severe diseases and die when infected with SARS-CoV-2 virus. Two doses of vaccines of $S_{FG}$, $S_{MG}$ or adjuvant only were given intramuscularly at day 0 and 14, sera were collected at day 28 and 42, $1 \times 10^3$ TCID50 SARS-CoV-2 were used to infect each mice intranasally (FIG. 3a). The spike specific antibody IgG titers of $S_{MG}$ immunized mice are 1.9-fold higher than $S_{FG}$ group (40,000 vs 20.000), and the neutralization titers of $S_{MG}$ are 2.8-fold higher than $S_{FG}$ group (FIGS. 3b and 3c). Surprisingly, in this severe-disease model, $S_{FG}$ vaccination failed to protect the CAG-hACE2 transgenic mice from severe disease, as observed from rapid decease of body weights and all of them died before day 7 post virus infection. The disease progression of the $S_{FG}$ vaccinated group was only slightly better than the adjuvant only group (FIGS. 3d and 3e). In contract, the $S_{MG}$ vaccinated group exhibited slight weight loss, and all of them survive the SARS-CoV-2 infection. This result demonstrates the superiority of $S_{MG}$ vaccination in the SARS-CoV-2 severe-disease transgenic mouse model.

Figure 4:
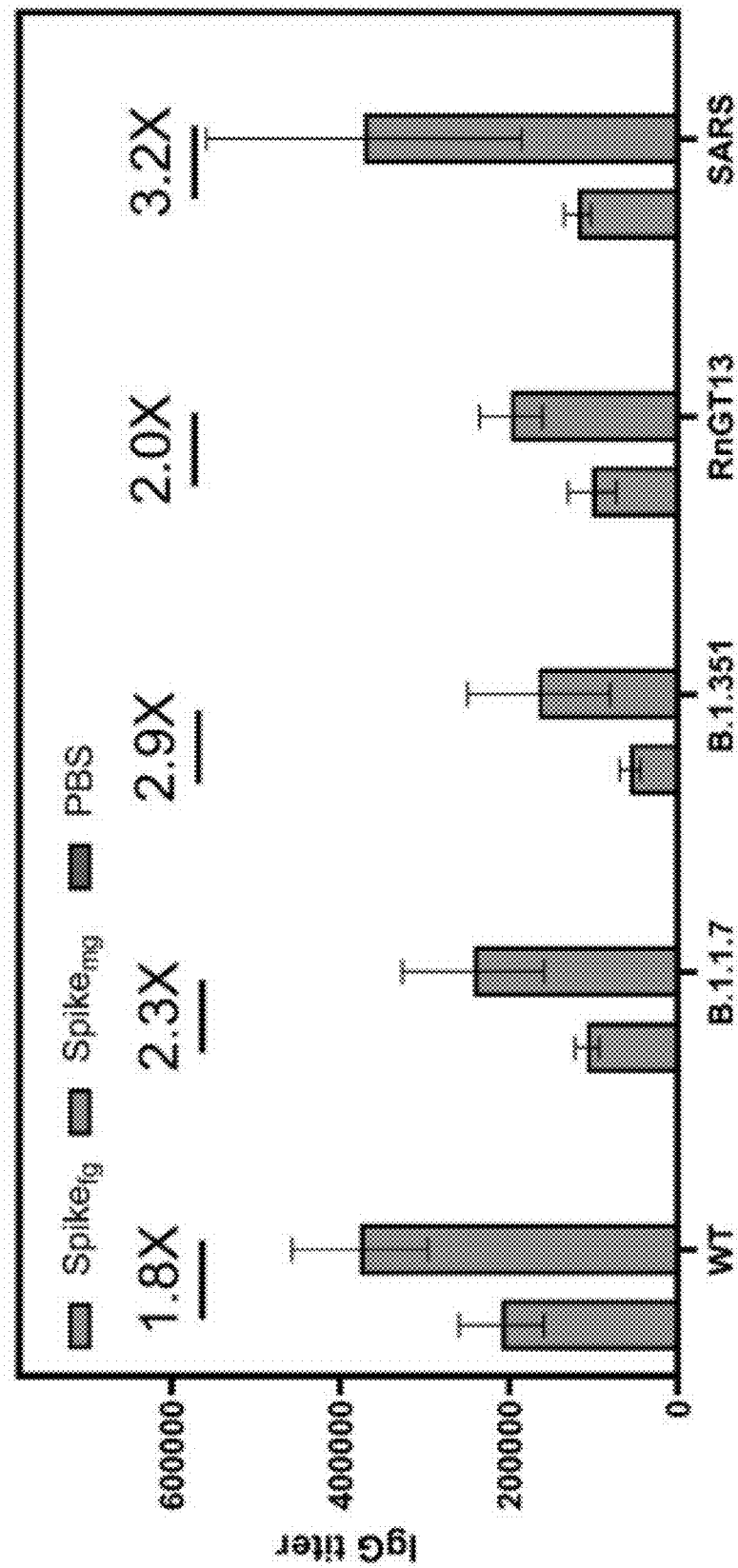
FIG. 4 (a) to (f). Antibodies induced by $S_{MG}$ vaccine in mice for enhanced binding and neutralization breadth and potency against SARS-CoV-2 variants. (a) Schematic representations of SARS-CoV-2 spike protein structure and the mutation landscape of variants used in this study are illustrated. RBD, receptor binding domain. In the mutation map, a dot (.) indicates the same amino acid in that position as wild type and a dash (-) indicates a deletion. (b) The SARS-CoV-2-specific IgG antibody titer was determined by ELISA. The binding fold increase of the antibody elicited by $S_{MG}$ over $S_{FG}$ vaccines are indicated by numbers above the bars. (c) SARS-CoV-2 variants pseudovirus neutralization curves are shown. (d) Titers that achieve 50% pseudovirus neutralization (pNT50) of SARS-CoV-2 variants are plotted. The neutralization fold increase of the antibody elicited by $S_{MG}$ over $S_{FG}$ vaccines are indicated by numbers above the bars. (e) Infectious SARS-CoV-2 variants neutralization curves determined by plaque reduction neutralization test (PRNT) are shown. (f) Titers that achieve 50% neutralization (PRNT50) of SARS-CoV-2 variants are plotted. Data are means±SEM (standard error of the mean). The curves were fit by nonlinear regression using GraphPrism 9.0 and the comparisons were performed by multiple t-test (paired, two tailed). The titers comparisons were performed by Student's t-test (unpaired, two tailed). The neutralization fold increase of the antibody elicited by $S_{MG}$ over $S_{FG}$ vaccines are indicated by numbers above the bars. Blue squares, transgenic mice immunized with $S_{FG}$; Red triangles, transgenic mice immunized with $S_{MG}$; Gray dots, Control group animals (PBS group).
Figure 4:
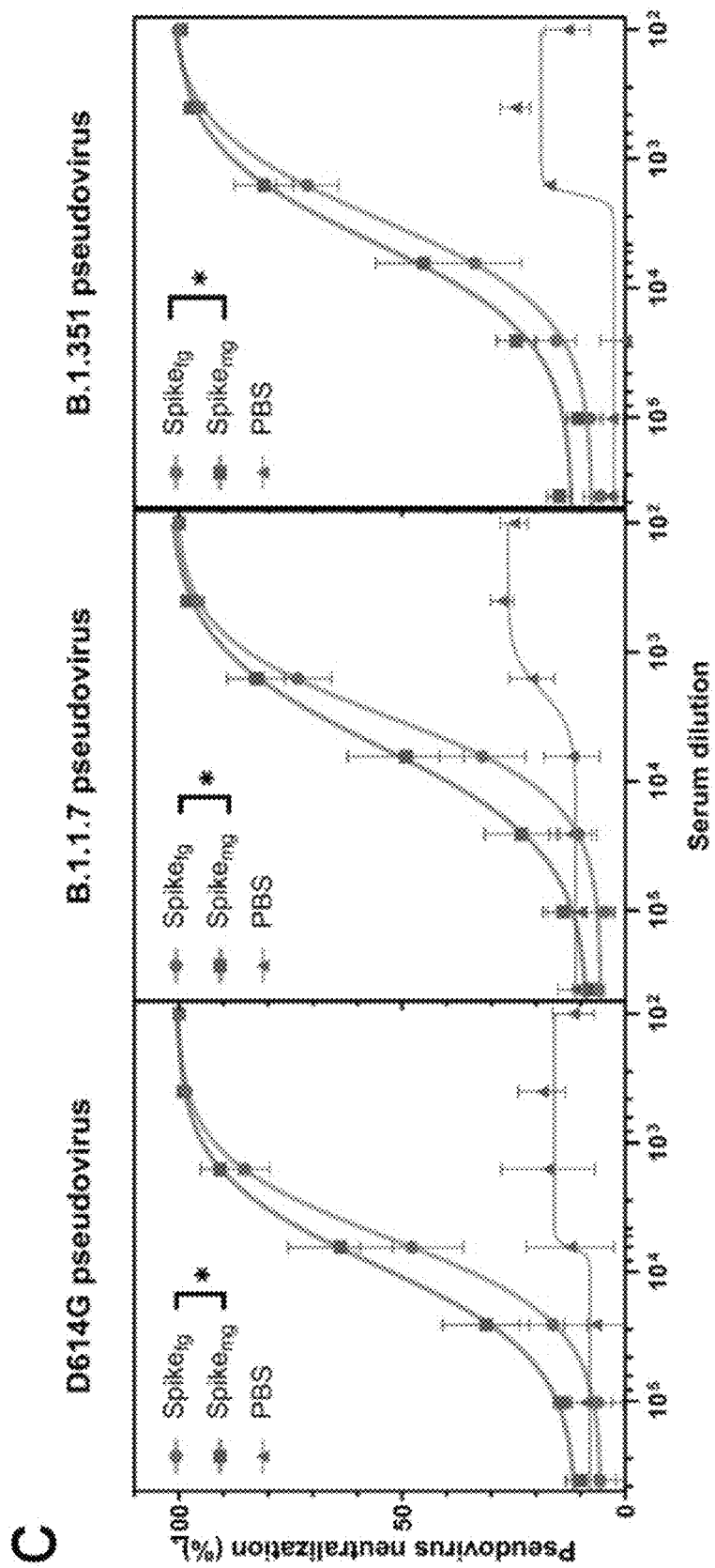
Figure 4:
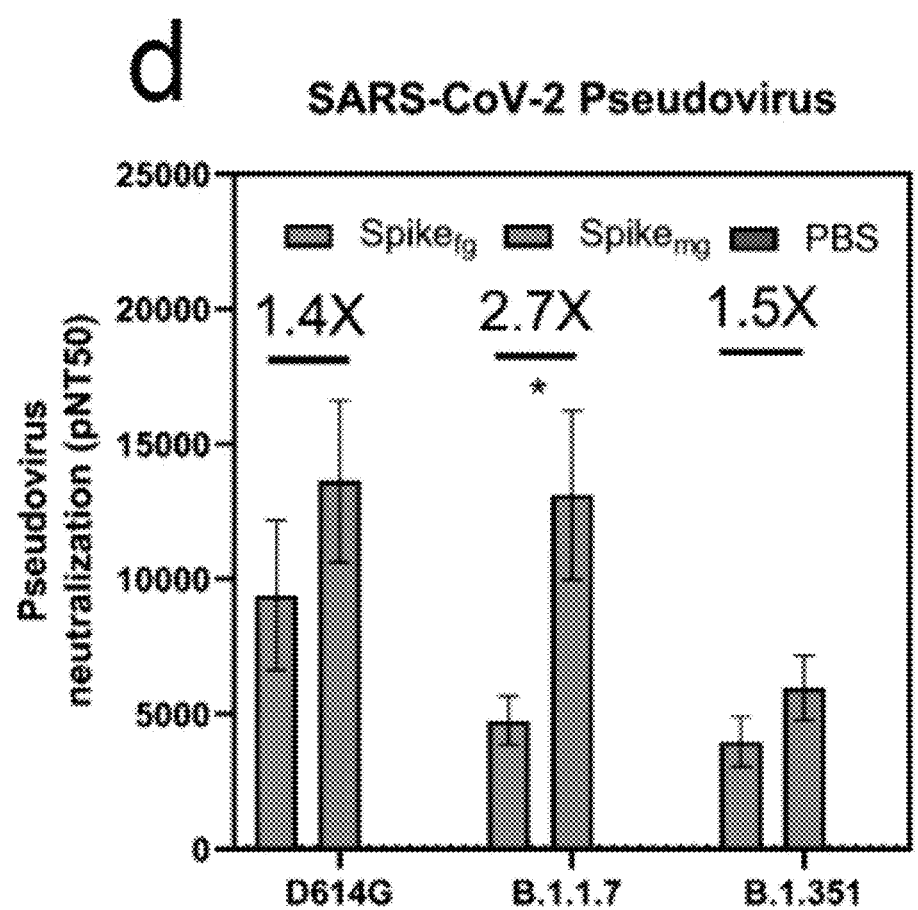
Figure 4:
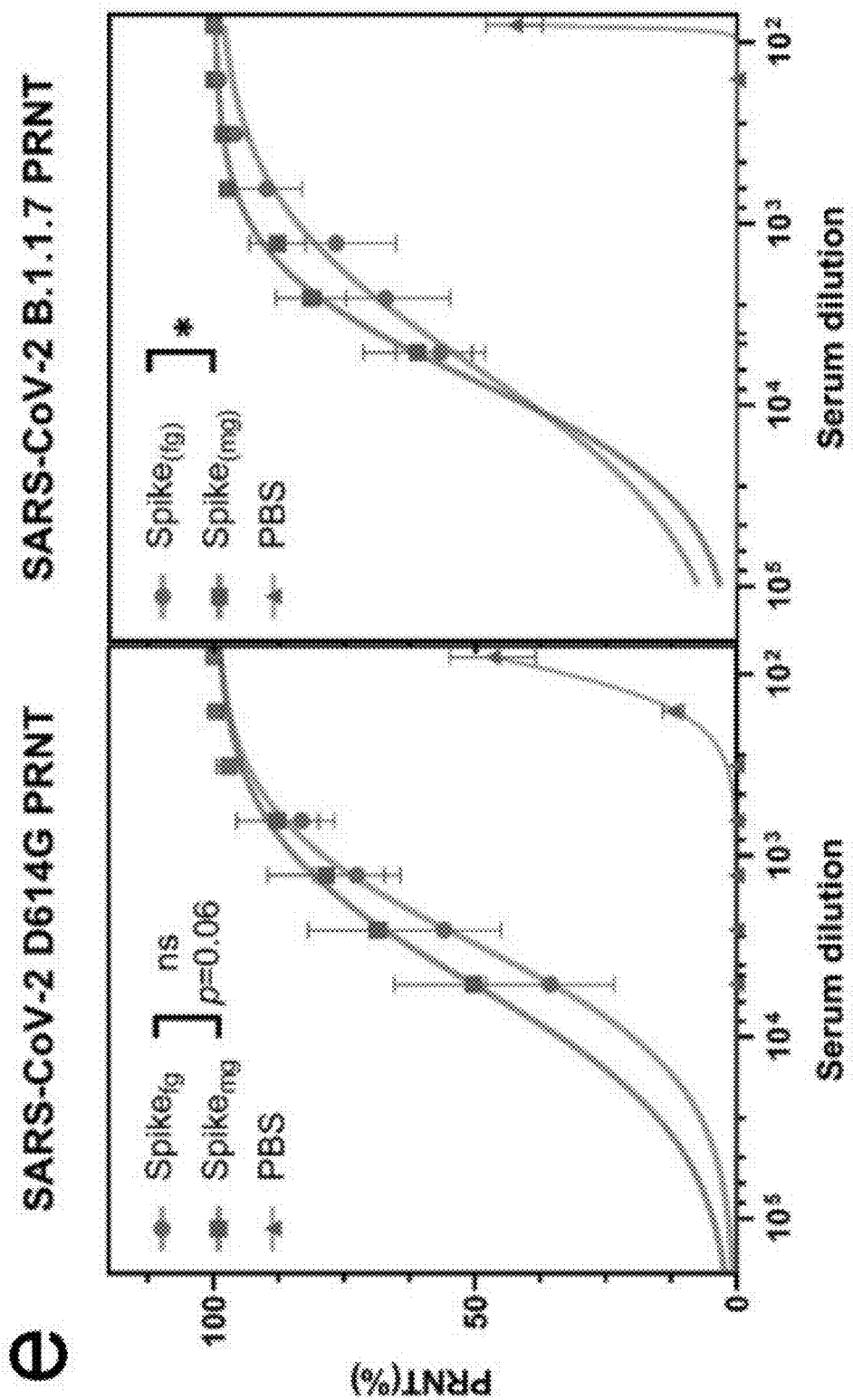
Figure 4:
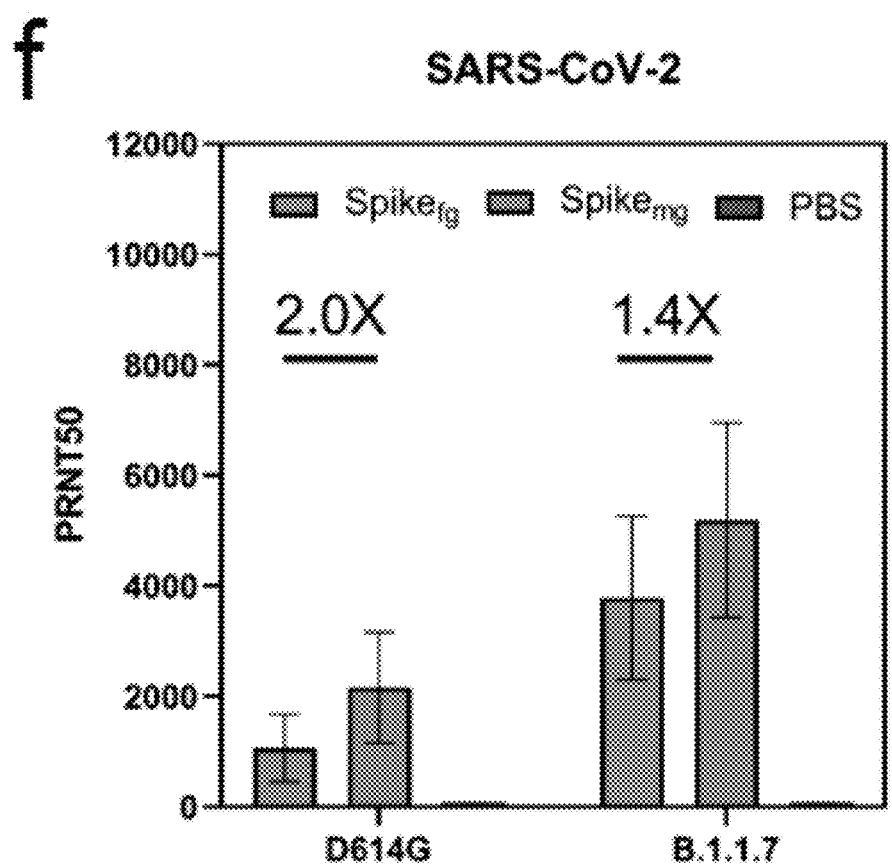

Example 17: Antibodies Induced by $S_{MG}$ Vaccine in Mice for Enhanced Binding and Neutralization Breadth and Potency Against SARS-CoV-2 Variants We then analyzed whether there are differences in the antibody responses elicited from either vaccination of $S_{FG}$ or $S_{MG}$, which has the spike native sequence from Wuhan strain, with regard to their ability to neutralize the newly emerged SARS-CoV-2 variants of concern (FIG. 4). Compared with $S_{FG}$, $S_{MG}$ immunization elicited better spike specific antibody IgG binding to not only spike native from WT (Wuhan strain), but also variants D614G, B.1.1.7, B.1.351, bat CoV RnGT13 and SARS-CoV-1 (FIG. 4b). Pseudotyped viruses of SARS-CoV-2 variants were used to gauge the ability to neutralize infections from the vaccine immunized sera. Again, the sera from $S_{MG}$ immunization possess superior neutralization ability towards D614G, B.1.1.7 and B.1.351 pseudoviruses, and they are 1.4, 2.7 and 1.5 folds better than $S_{FG}$ induced sera, respectively (FIGS. 4c and 4d). Finally, SARS-CoV-2 real virus D614G and B.1.1.7 were used in a plague reduction neutralization assay (FIGS. 4e and 4f). $S_{MG}$ vaccination elicits better neutralizing antibody response to D614G and B.1.1.7 variants compared with $S_{FG}$ vaccination, and they are 2.0 and 1.4 folds better, respectively.

Figure 5:
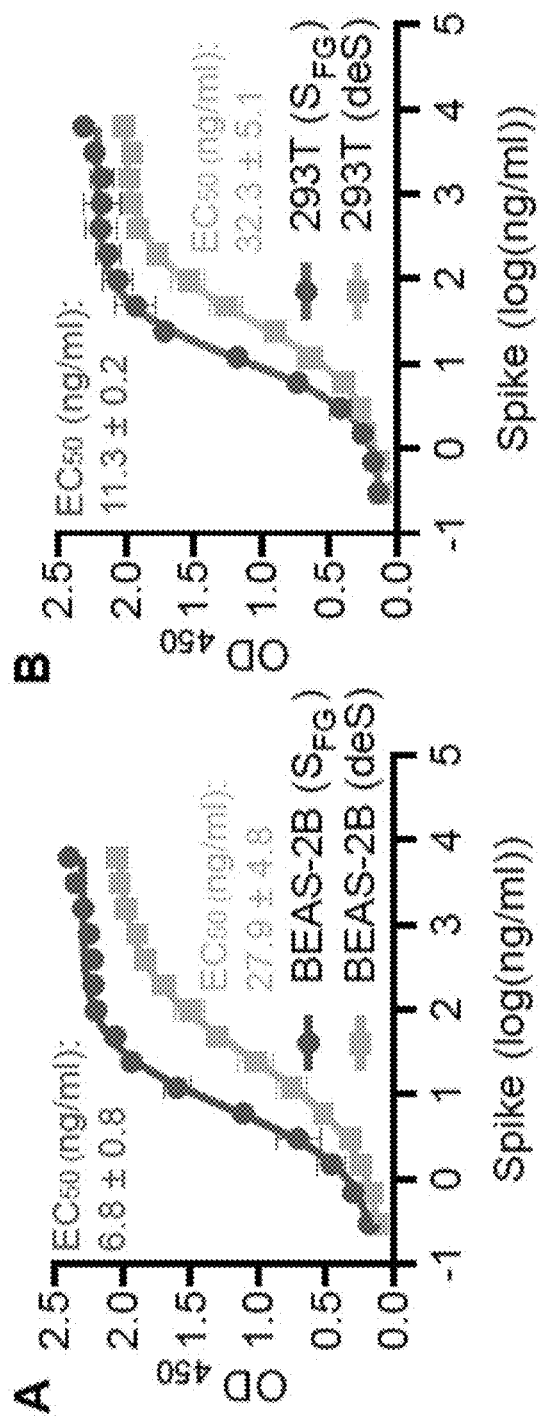
FIGS. 5 (A) to (G). S protein glycosylation impacts ACE2 receptor binding and SARS-CoV-2 infection. (A to C) Binding avidity of ACE2 was measured for differently glycosylated S protein ectodomains ($S_{FG}$; original fully glycosylated, blue; deS, nonsialylated, light blue; $S_{HM}$, high-mannose, yellow; and $S_{MG}$, mono-GlcNAc-decorated, red) from BEAS-2B (A), HEK293T (B), and HEK293S (GnTI⁻) cells without or with Endo H digestion (C). Data of three technical replicates are shown as means±SD, and curves fit by nonlinear regression for $EC_{50}$ values. (D) Viral infectivity was measured for pseudoviruses carrying differently glycosylated S protein with the same input amount (0.3 μg/ml of p24 equivalent) colored accordingly as in (C). RLU, relative luminescence unit. Data of six technical replicates shown as means±SD and analyzed with ordinary one-way ANOVA test followed by Tukey's multiple comparisons test. ns, not significant; ****P<0.0001. (E) A schematic view of SARS-CoV-2 S protein [wild type (WT)] is shown colored by domain, including N-terminal domain (NTD; 14-306; orange), receptor binding domain (RBD; 319-541; red), two subdomains (SD1/2; 542-685; yellow), fusion peptide proximal region (FPPR; 816-856; green), heptad repeat 1 (HR1; 912-984; teal), connecting domain (CD; 1063-1162; blue), heptad repeat 2 (HR2; 1163-1211; purple), and transmembrane domain (TM; 1214-1234; white). N-glycan (drawn as branches) and O-glycan (circles) sites are marked with residue number. S1 and S2 domains are shown above. (F) Viral titers are shown for pseudoviruses carrying WT S protein or mutants with glycans removed at each shown glycosite, normalized by p24 quantification, and colored accordingly as in (E). (G) Infectivity of the same panel of pseudoviruses as in (F) tested in five hACE2-expressing cell lines. Values in (F) and (G) are normalized against WT values (defined as 100%, colored in dark gray) with means±SD of three independent experiments.
Figure 5:
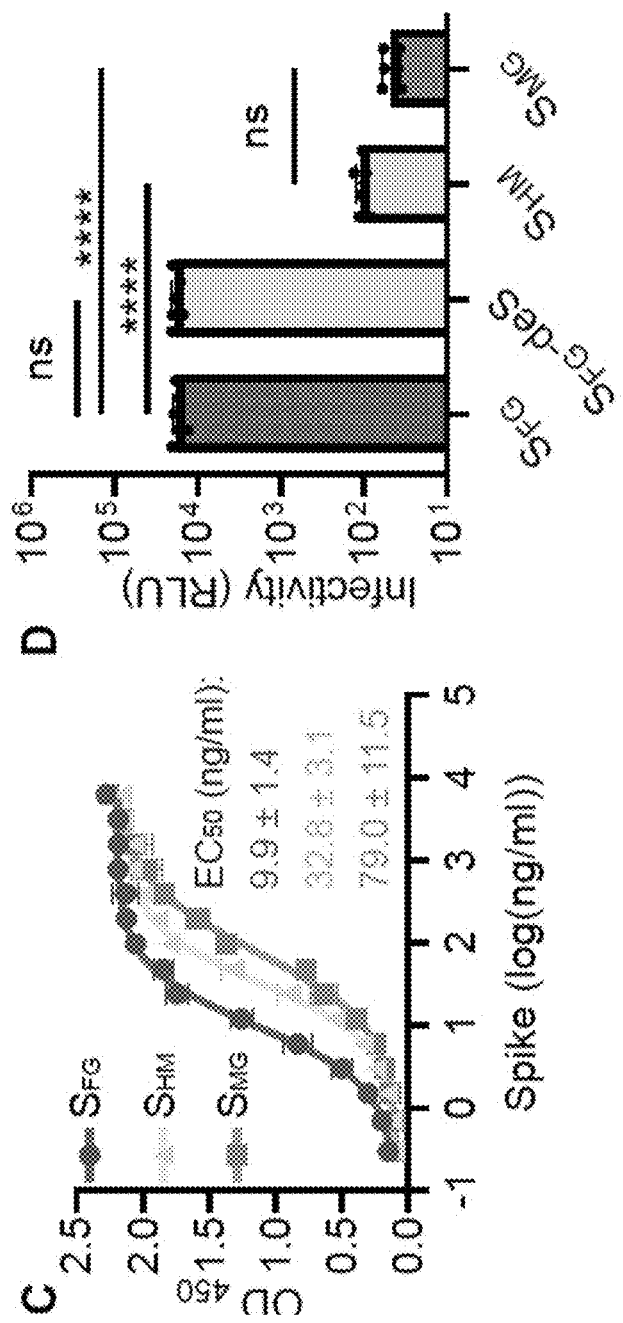
Figure 5:
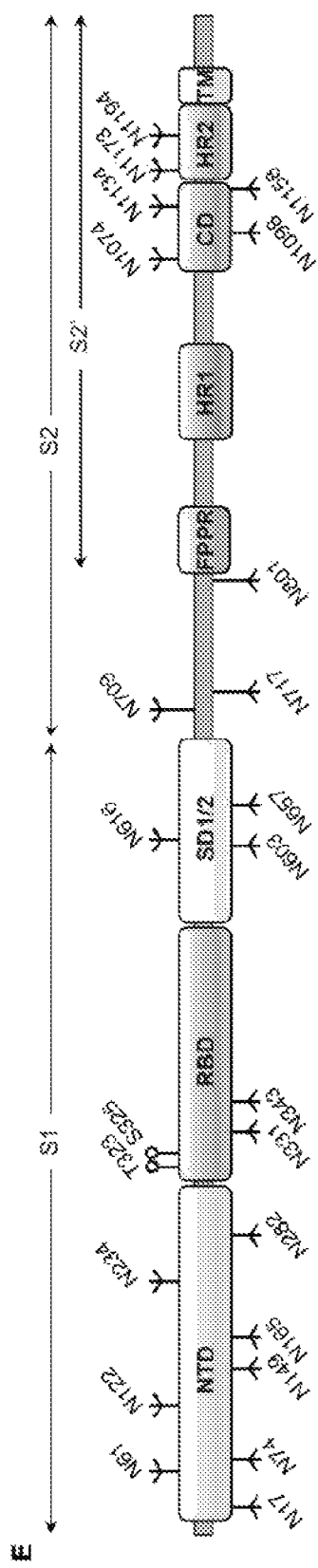
Figure 5:
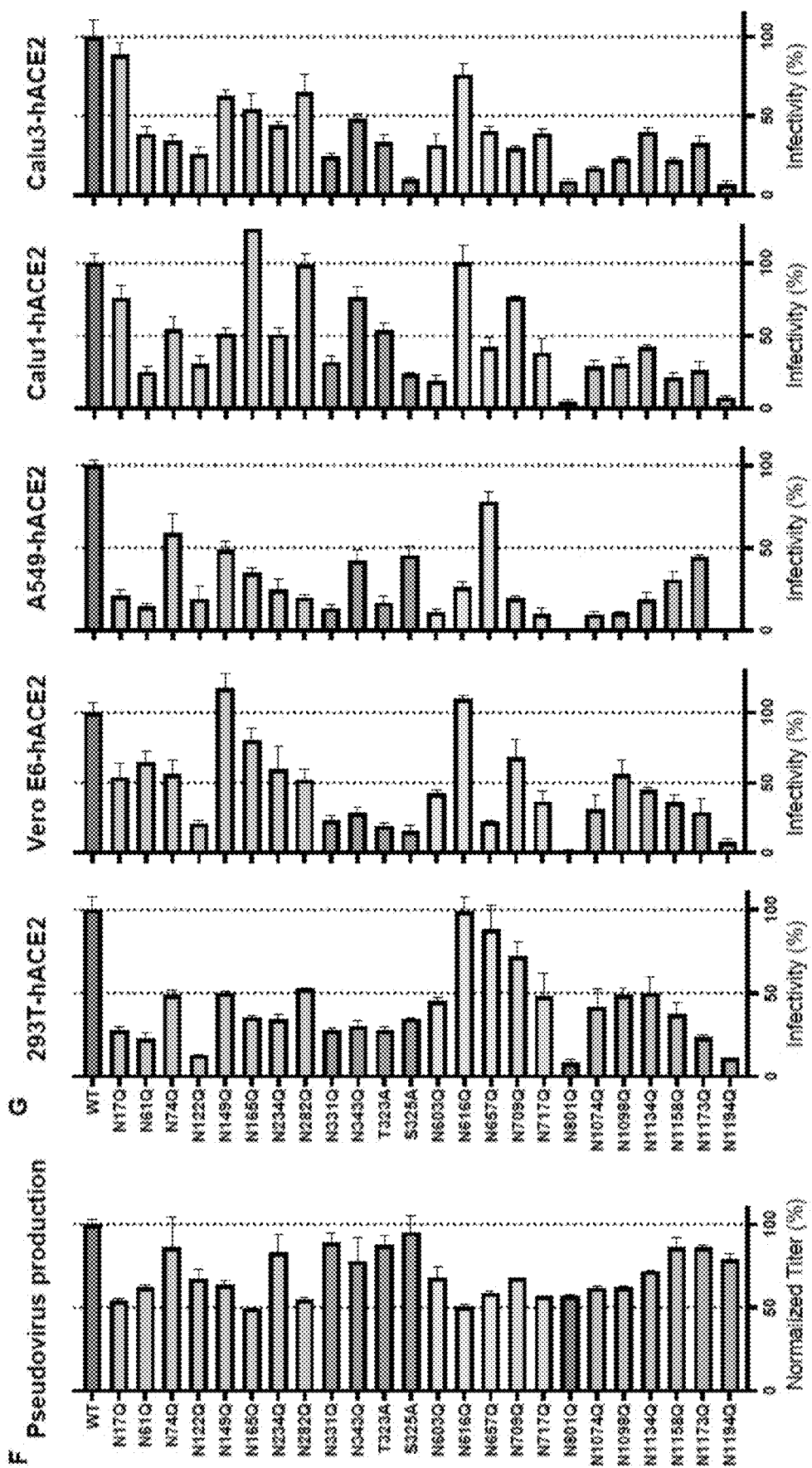

Example 18: Glycosylation Affects Pseudovirus S Protein Interacting with ACE2 on Several Cell Types To understand the importance of glycosylation, we expressed S protein from lung epithelial cells, the primary cells for infection, and found that sialylation of S protein is required for higher avidity to the receptor (FIG. 5A). A similar pattern was also observed for HEK293T cell-generated S protein (FIG. 5B), and the avidity was also reduced for the S protein with only high-mannose glycans or in the glycoform with all N-glycans trimmed to a single N-acetylglucosamine (GlcNAc) (FIG. 5C). The impact of its glycosylation was further tested by pseudovirus infection in human angiotensin-converting enzyme 2 (hACE2)-expressing HEK293T cells, revealing a consistent trend, when the same amount of virus was applied (FIG. 5D). This allowed us to conclude that complex-type glycans and sialylation are functionally important for S protein-mediated infectivity. A full panel of 24 lentivirus-based pseudovirus variants (comprising the 22 N- and 2 O-glycosites) were also generated for evaluating the viral entry efficiency in five hACE2-expressing cell lines, including HEK293T, Vero-E6, and three human lung cell lines, A549, Calu-1, and Calu-3 cells (FIG. 5, E to G). These pseudoviruses were based on the S construct with C-terminal 19 amino acid deletion, which produced the highest viral titer. Pseudovirus production was quantified by a p24 immunoassay, and results were normalized against the titer of each mutant strain (FIG. 5F). Every N-glycosite asparagine (Asn) was substituted to glutamine (Gln) to minimize the structural influence because of their chemical similarity, and each O-glycosite threonine (Thr) or serine (Srn) was substituted to alanine (Ala). Because the mutagenesis did change the amino acids, the resulting change in infectivity would come from collective factors, including the glycosylation-related conformational shifts that affect receptor engagement and the surface abundance of S protein affected by protein expression, folding, and trafficking. Results showed that disruption of S protein glycosylation reduced infectivity. A substantial reduction was observed for two mutations in the receptor binding domain (RBD), N331Q and N343Q, as well as for mutations of the two O-glycosites (T323A and S325A), despite the low occupancy of the latter (FIG. 5G). In addition, deletion of N122 glycosylation in the N-terminal domain (NTD) resulted in reduced infectivity and low protein expression (FIG. 5G). Two NTD mutations, N149Q and N165Q, increased infectivity in Vero-E6 and Calu-1 cells, respectively, although decreased infections were observed in other cells (FIG. 5G). Note that the glycans attached to this N165 residue are structurally proximal to the neighboring RBD in the trimeric S protein, and its mutation reduced ACE2 binding probably because of the conformational shift of RBD toward the "down" state. We identified two mutants, N801Q and N1194Q (FIG. 5F), that universally abolished virus infectivity in all five cells. The glycosite N801 is located near the fusion peptide proximal region (FPPR), and N1194 is near the center of heptad repeat 2 (HR2) helix and is the last N-glycosite preceding the transmembrane domain (FIG. 5E). These mutations both caused low-yield expression. The N801Q mutant was more prone to degradation, and the N1194Q mutant disrupted S protein trimerization, which could be part of the explanation for the reduction of infectivity by pseudoviruses carrying these mutants.

Example 19: S Protein from Lung Epithelial Cells Contains More Sialylated Complex-Type Glycans and Highly Conserved Epitopes in S Protein are Largely Shielded by Glycans The glycan profile analysis of S protein revealed a higher abundance of complex-type glycans (78%), and fewer hybrid-type glycans (less than 1%) for S protein were produced in the human lung epithelial cell line BEAS-2B (FIG. 6A) as compared with S protein produced in the human kidney epithelial cell line, HEK293T (61 and 23%, respectively) (FIG. 6B). Among the high mannose-type glycans, the N-linked mannose-5 glycan (man5) was the predominant type found across the HEK293T-expressed S protein, although it is only seen at site N61 from BEAS-2B cells. In addition, the complex-type glycans at sites N74, N149, N282, and N1194 from BEAS-2B cells were more diversely processed (multiple antennae, galactosylation, fucosylation, or sialylation) than those from HEK293T cells. In contrast, the glycans at sites N122, N331, N1098, and N1134 were less diverse. Furthermore, N149 and N17 harbored no core fucose in BEAS-2B. We observed an overall higher degree of sialylation on all 22 N-glycosites from BEAS-2B (53%) than that from HEK293T (35%), HEK293E (26%), or the previously reported HEK293F cells (15%) (Y. Watanabe, J. D. Allen, D. Wrapp, J. S. McLellan, M. Crispin, Site-specific glycan analysis of the SARS-CoV-2 spike. *Science* 369, 330-333 (2020)). Particularly, the two N-glycosites (N331 and N343) of RBD are more sialylated in BEAS-2B (99 and 39%) than in HEK293T (49 and 15%). Despite the differences, the S protein from all cell types contains a non-complex-type glycan belt located around the middle section of the S2 domain (FIG. 6C), where the N-glycosite N801 is critical for infection (FIG. 5G), N1074 contains diverse glycans, and N717 is essential for S protein expression.

From the modeled SARS-CoV-2 S protein structure and the glycan profile from BEAS-2B cells, we conducted structural analysis of glycan coverage over protein surface areas and overlaid with multiple alignment results using 1,117,474 S protein sequences (S. Elbe, G. Buckland-Merrett, Data, disease and diplomacy: GISAID's innovative contribution to global health. *Global Chall.* 1, 33-46 (2017)). It revealed several regions that were highly conserved, yet shielded by glycans, including the lower flank of RBD, the S2 stem region with the non-complex-type glycan belt, and the C-terminal part of S2 involving the connecting domain (CD) and HR2 (FIG. 6, D and E). On the primary sequence level, these regions were shown as conserved epitopes. Sequence conservation analysis also showed that most of the glycosite regions were highly conserved, and the most conserved ones (mutation rate lower than 0.02%) included those in the NTD (N61, N122, N165, and N234), the RBD (S325, N331, and N343), the subdomain 1/2 (SD1/2) (N603 and N657), the stem region of subunit 2 (S2) (N709, N1098, N1134, N1158, N1173, and N1194), and N801 near the FPPR. Most of these regions contain around 20 to 40% of conserved surface residues, and among them, a certain percentage of residues were shielded by glycans, 36% in the RBD and about 50% in other regions. Although harboring no N-glycosites, the HR1 region had 69% of its conserved surface residues being covered by glycans stemmed from adjacent domains. These results highlighted the importance of S protein glycosylation, both structurally and evolutionarily, leading to the thought that exposing glycan-shielded conserved regions may elicit immune responses against conserved epitopes. (It is more important to describe the 12 conserved epitopes as targets for vaccine resign. 10 of the 12 epitopes are shielded by glycans; and removal of the shielded glycans exposes the conserved epitopes to elicit broadly protective responses)

Example 20: $S_{MG}$ was Developed as a Vaccine and $S_{MG}$ Vaccine Elicited Better Immune Response Using Different Antibody Subclasses Our initial attempt to mutate multiple glycosites led to a markedly reduced expression of S protein. Yet, when we expressed it from GnTI HEK293S cells, we were able to produce a high-mannose glycoform S protein ($S_{HM}$) with good yield and purity. We then trimmed the glycans using endoglycosidase H (Endo H) to a single GlcNAc at each N-glycosite, generating a soluble trimmer mono-GlcNAc-decorated S protein, which we called $S_{MG}$ (FIG. 7A). $S_{MG}$ was confirmed by mass spectrometry that all N-glycosites mostly occupied with single GlcNAc, and the occupancies of untreated O-glycans were too low to be detected. This modified $S_{MG}$, and $S_{HM}$, as well as the original fully glycosylated S protein ($S_{FG}$) were mixed with aluminum hydroxide (alum) as an adjuvant and were then used to immunize BALB/c mice (n=5) by intramuscular injection (FIG. 7B). The $S_{FG}$ used for comparison in this study was expressed by HEK293E cells and contained diverse glycans; this is similar to the immunogens used in many current COVID-19 vaccines that are either approved or in clinical trials, including the insect cell-expressed S protein vaccines from Sanofi and Novavax (P. J. Klasse, D. F. Nixon, J. P. Moore, Immunogenicity of clinically relevant SARS-CoV-2 vaccines in nonhuman primates and humans. *Sci. Adv.* 7, eabe8065 (2021)), the Chinese hamster ovary (CHO) cell-expressed recombinant S vaccine from Medigen (T.-Y. Kuo, M.-Y. Lin, R. L. Coffman, J. D. Campbell. P. Traquina, Y.-J. Lin, L. T.-C. Liu, J. Cheng. Y.-C. Wu, C.-C. Wu, W.-H. Tang, C.-G. Huang. K.-C. Tsao, C. Chen, Development of CpG-adjuvanted stable prefusion SARS-CoV-2 spike antigen as a subunit vaccine against COVID-19. *Sci. Rep.* 10, 20085 (20'20)), the adenovirus-based vaccines from AstraZeneca and Johnson & Johnson, and the mRNA vaccines from Pfizer-BioNTech and Moderna (P. J. Klasse, D. F Nixon, J, P. Moore, Immunogenicity of clinically relevant SARS-CoV-2 vaccines in nonhuman primates and humans. *Sci. Adv.* 7, eabe8065 (2021)). Both $S_{FG}$ and $S_{MG}$ proteins demonstrate essentially the same trimeric structure in solution by negative staining analysis.

Figure 7:
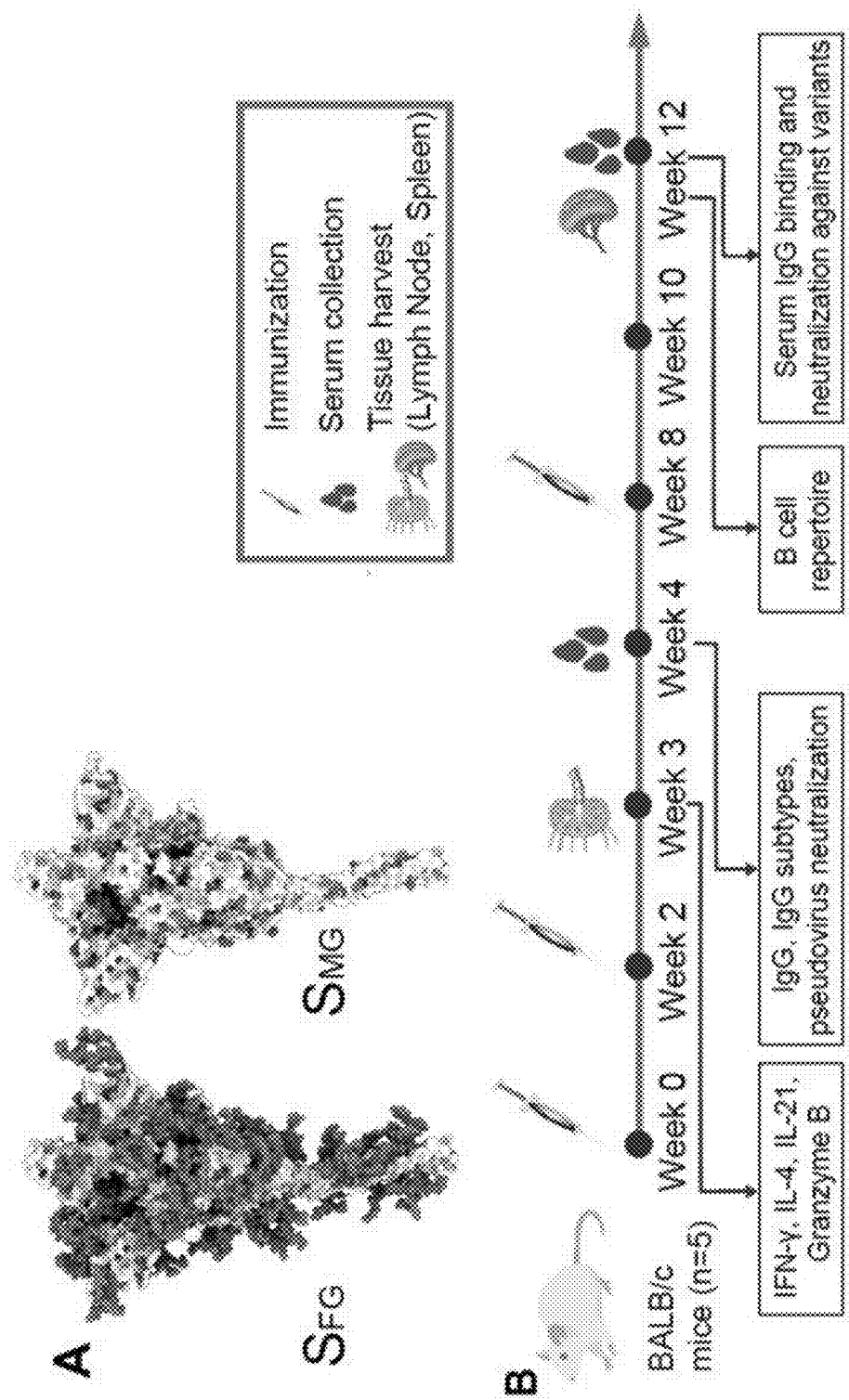
FIGS. 7 (A) to (S). $S_{MG}$ vaccination elicits stronger humoral and cellular immune responses than $S_{FG}$ in BALB/c mice. (A) Structural models of $S_{FG}$ and $S_{MG}$ protein vaccine are shown (according to FIG. 2C). Blue: glycans; gray: protein. $S_{FG}$ was expressed by HEK293E without further modification. $S_{MG}$ was obtained by enzymatic digestion to truncate all N-glycans of $S_{HM}$ expressed by HEK293S GnTI$^-$ to single GlcNAc, whereas O-glycans were unmodified. (B) Immunization schedule using proteins as in (A) as immunogens in BALB/c mice (n=5 in each experiment). $S_{FG}$ (blue), $S_{HM}$ (yellow), $S_{MG}$ (red), and control (gray). Alum, aluminum hydroxide. (C) Anti-S protein IgG titers of serum samples were analyzed by ELISA. (D) Neutralization titers of serum samples were measured using pseudovirus with WT S protein. (E to G) IgG subtype analysis of sera, including IgG1 (E), IgG2a (F), and the IgG2a:IgG1 ratio (G). (H to K) The percentage of Tfh in activated nonregulatory CD4 T cells (H) and the percentages of IFN-γ (I)-, IL-4 (J)-, and IL-21 (K)-expressing Tfh cells (CD4$^+$CD19$^-$CD44$^{hi}$Foxp3$^-$PD-1$^+$CXCR5$^+$) in the lymph nodes (LNs) of BALB/c mice by flow cytometry. (L) The percentage of granzyme B-producing CD8$^+$ T cells (CD3$^+$B220$^-$CD8$^+$CD49b$^-$) in the LN of BALB/c mice analyzed by flow cytometry. (M) The ratio of S protein-specific B cells (CD3$^-$CD19$^+$S protein$^+$) (percentage) normalized to fluorescence minus one (FMO) control staining (stained without S protein) (percentage) in the spleen is shown. (N) Kappa and lambda light chain usage is shown. (O and P) Heavy (O) and kappa (P) chain distribution of B cell repertoire analysis. Less than 5% usage is shown in white. (Q to S) Anti-S protein IgG titers (Q), pseudovirus neutralization titers (R), and authentic virus neutralization titers (S) are shown for serum isolated from BALB/c mice after three doses of indicated vaccines against SARS-CoV-2 WT (or D614G) and variants (number above each bar indicate fold of increase of $S_{MG}$ compared to $S_{FG}$ group). pNT$_{50}$ represents the reciprocal dilution achieving 50% neutralization. The dotted line in bar charts represents the lower limit of detection. Data are shown as means±SEM and analyzed by two-sided Mann-Whitney U test to compare two experimental groups, except in (N), where five samples were pooled together and a chi-squared test was used. P values shown above each bar. *P<0.05; **P<0.01.
Figure 7:
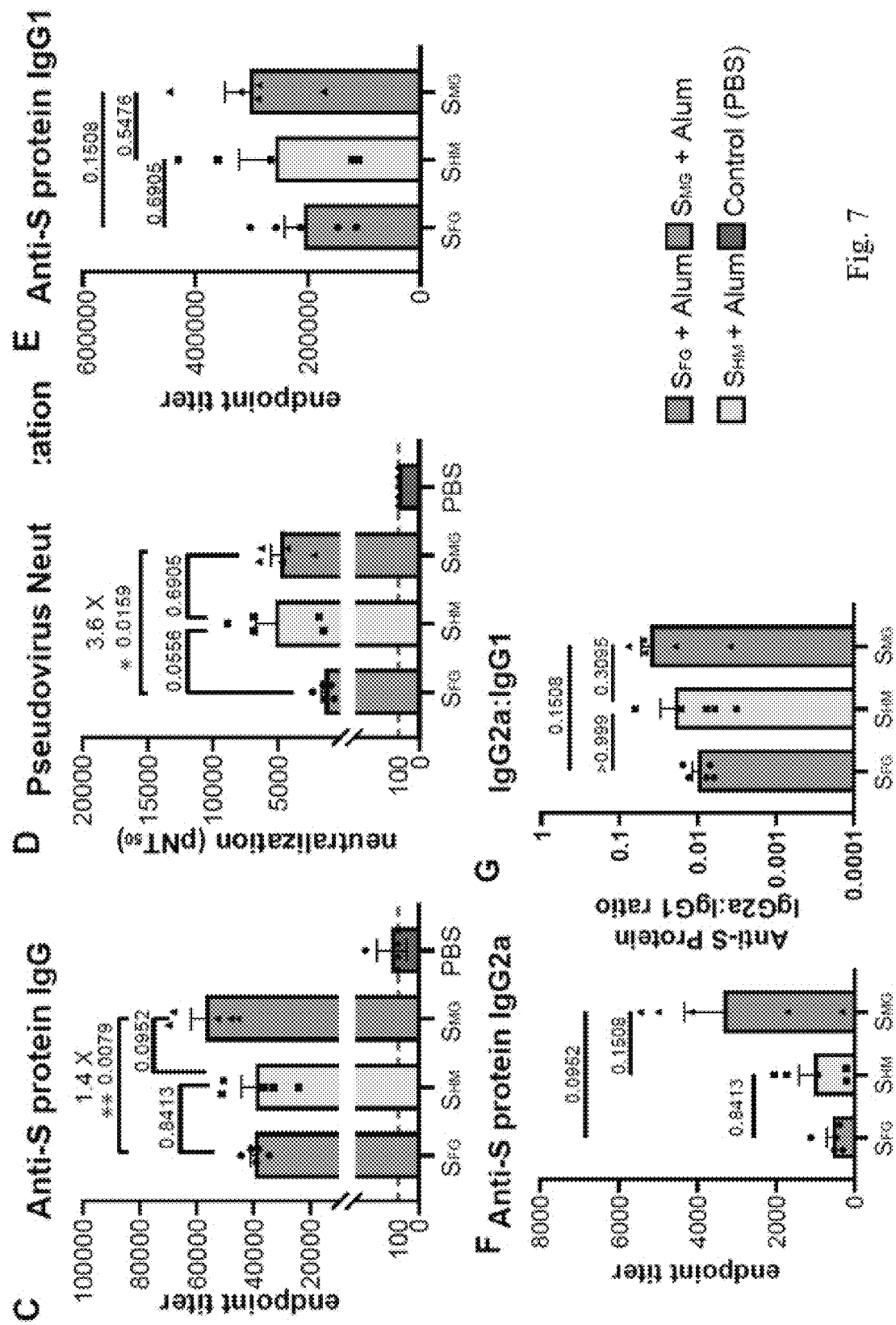
Figure 7:
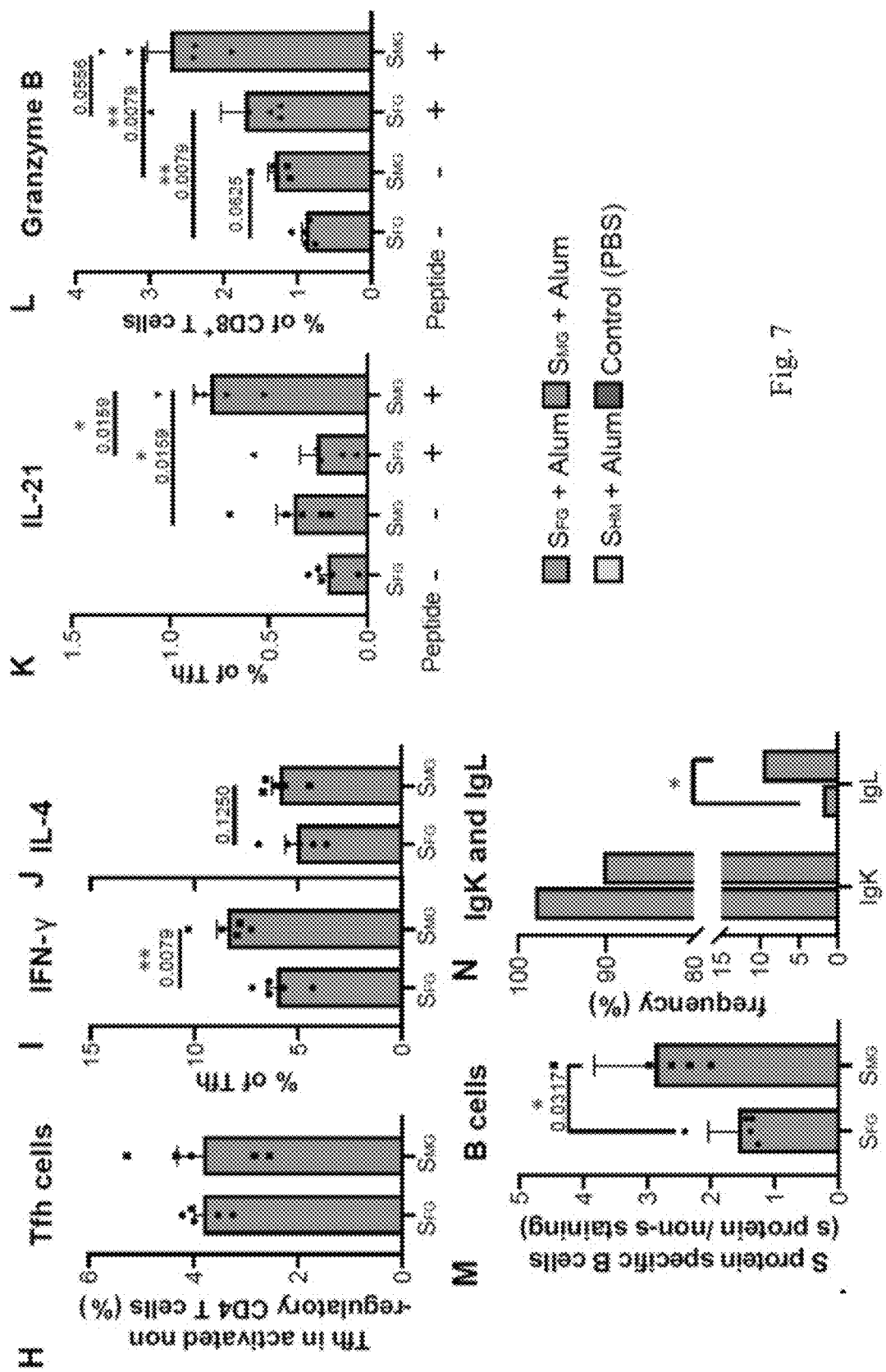
Figure 7:
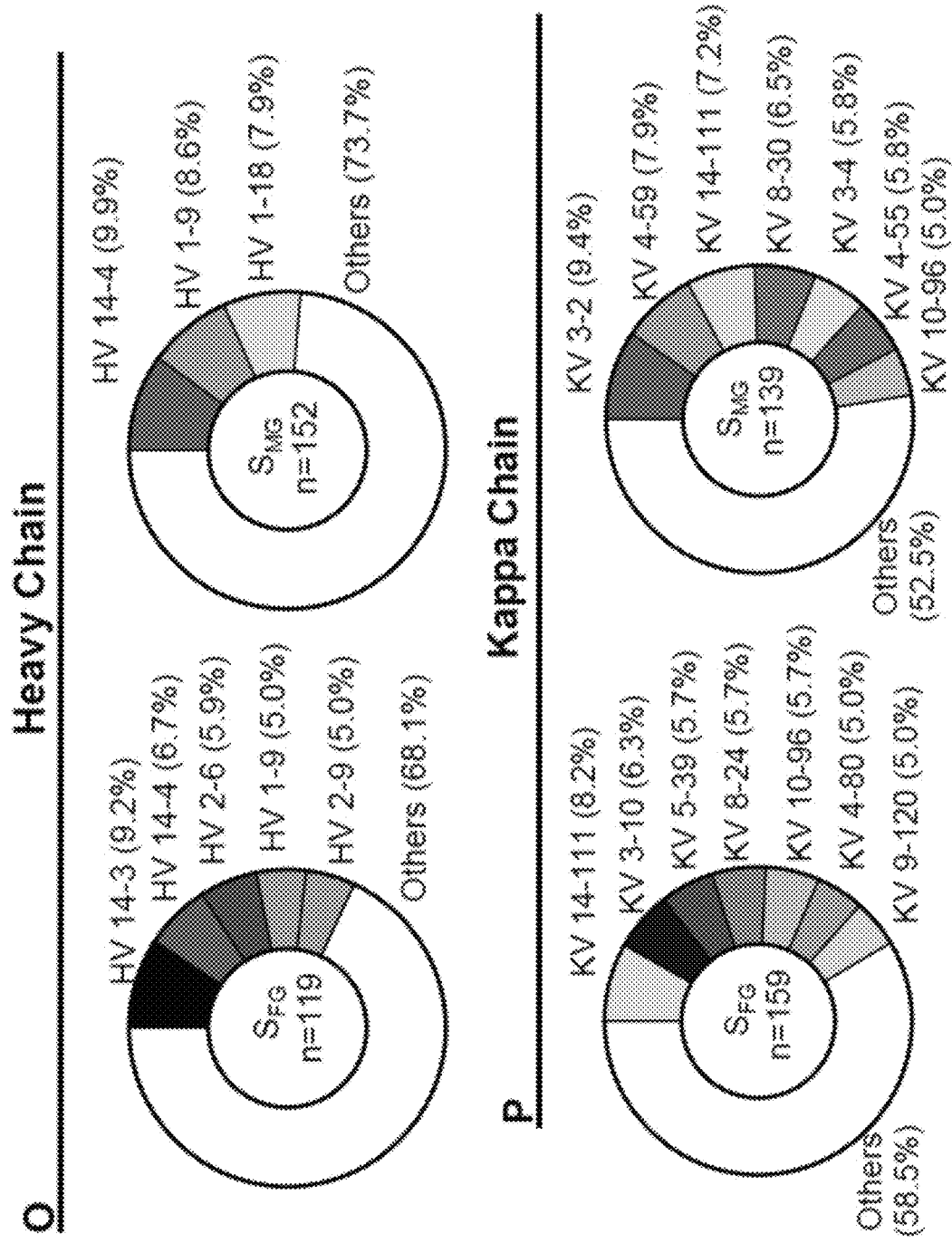
Figure 7:
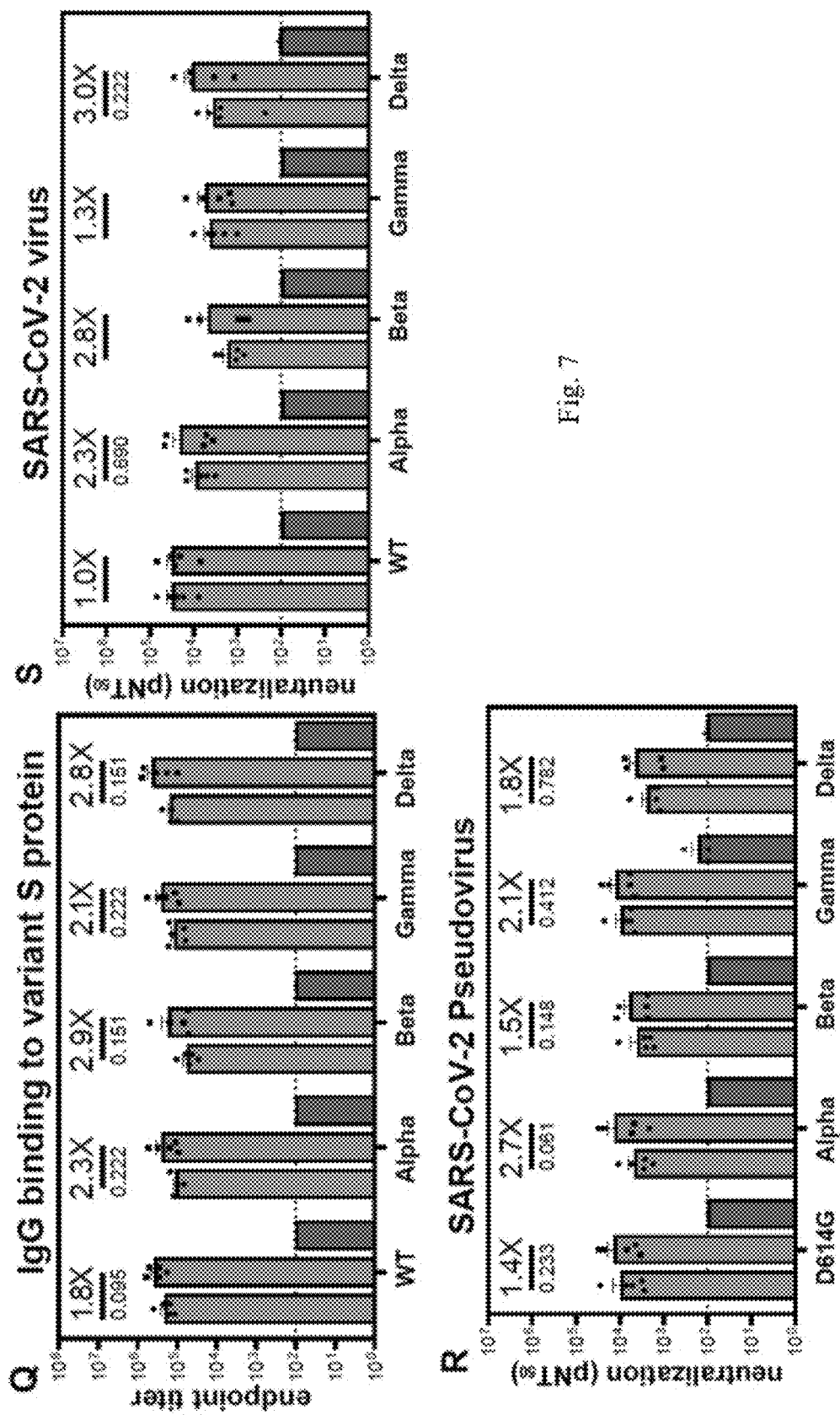

Mice immunized with $S_{MG}$ induced superior humoral immune response after second immunization as compared with $S_{FG}$, with a 1.44-fold significantly higher immunoglobulin G (IgG) titer against S protein (end point titer: $S_{FG}$, 39,408±1,619; $S_{MG}$, 56,957±5,091; P=0.0079) (FIG. 7C) and 3.6-fold stronger antibody neutralization potency based on the inhibition of SARS-CoV-2 pseudovirus infection (reciprocal half maximal neutralization titer $pNT_{50}$: $S_{FG}$, 1346±285; $S_{MG}$, 4791±767; P=0.0159) (FIG. 6D), whereas $S_{HM}$-immunized group shows similar anti-S IgG titers (39, 086±11,654) and no difference in $pNT_{50}$ titer compared with the $S_{FG}$ group. The analysis of IgG subtype titer and interferon-γ (IFN-γ) or interleukin-4 (IL-4) production by T follicular helper (Tfh) cells revealed that $S_{MG}$ vaccine induced more IgG2a, which is the marker for T helper 1 cell ($T_H1$) lymphocytes in BALB/c mice, a more balanced $T_H1/T_H2$ response, and more IFN-γ-expressing Tfh cells compared with the $S_{FG}$- and $S_{HM}$-vaccinated groups (FIG. 7, E to J). Furthermore, the $S_{MG}$ vaccine induced higher frequency of IL-21$^+$ Tfh cells (FIG. 7K) and an elevated frequency of granzyme B-producing CD8$^+$ T cells (FIG. 7L). These data indicated that a more potent humoral and cellular adaptive immune response was elicited by $S_{MG}$, as compared with that induced by $S_{FG}$. We then examined the frequency of S protein-specific B cells (CD3$^-$CD19$^+$S$^+$) from the spleen of mice immunized after the third dose of $S_{FG}$ or $S_{MG}$ (FIG. 6A) and found that mice immunized with $S_{MG}$ generated more S protein-specific B cells (FIG. 6M). The B cell repertoire analysis from $S_{FG}$- and $S_{MG}$-immunized mice (n=5) indicated that more lambda light chain genes were used in the $S_{MG}$ group compared with that in the S$_{FG}$ group (S$_{FG}$, 1.92%; S$_{MG}$, 9.68%) (FIG. 7N). In addition, antibodies derived from several specific loci of the Ig heavy chain variable region (IGHV) (FIG. 7O) and the Ig kappa chain variable region (IGKV) genes (FIG. 7P) were over-represented in the S$_{MG}$ group than in the S$_{FG}$ group, especially the IGHV1-18 gene (FIG. 7O). This finding suggested that B cell epitopes may be processed differently in these two groups, and it remains to be further explored whether and why this difference is immunologically beneficial. In addition, the three-dose S$_{MG}$ vaccination elicited higher end point titer IgG than the two-dose vaccination against wild-type (WT) S protein (end point titer: S$_{FG}$, 208.911±50,092; S$_{MG}$, 376,410±80,873). We observed differences between the S$_{MG}$ and S$_{FG}$ groups in serum IgG-binding curves measured by enzyme-linked immunosorbent assay (EISA) against the S protein from SARS-CoV-2 VOCs (P. R. Krause, T. R. Fleming, I. M. Longini, R. Peto, S. Briand, D. L. Heymann, V. Beral, M. D. Snape, H. Rees, A.-M. Ropero, R. D. Balicer, J. P. Cramer, C. Muñoz-Fontela, M. Gruber, R. Gaspar, J. A. Singh, K. Subbarao M. D. Vani Kerkhove, S. Swaminathan, M. J. Ryan. A.-M. Henao-Restrepo, SARS-CoV-2 variants and vaccines. *N. Engl. J. Med* 385, 179-186 (2021)), including alpha (B.1.1.7; P=0.0488), beta (B.1.351; P=0.0010), gamma (P.1; P=0.0068), and delta (B.1.617.2; P=0.0068), but no statistical differences in end point titers analysis (FIG. 7Q). Differences in neutralizing antibody responses against VOCs by pseudovirus neutralization curve, including alpha (P=0.0156), beta (P=0.0156), and delta (P=0.0078), were also observed, but no differences were observed in the pNT$_{50}$ titer values for pseudovirus or authentic virus neutralization (FIG. 7, R and S), as compared with S$_{FG}$.

Figure 8:
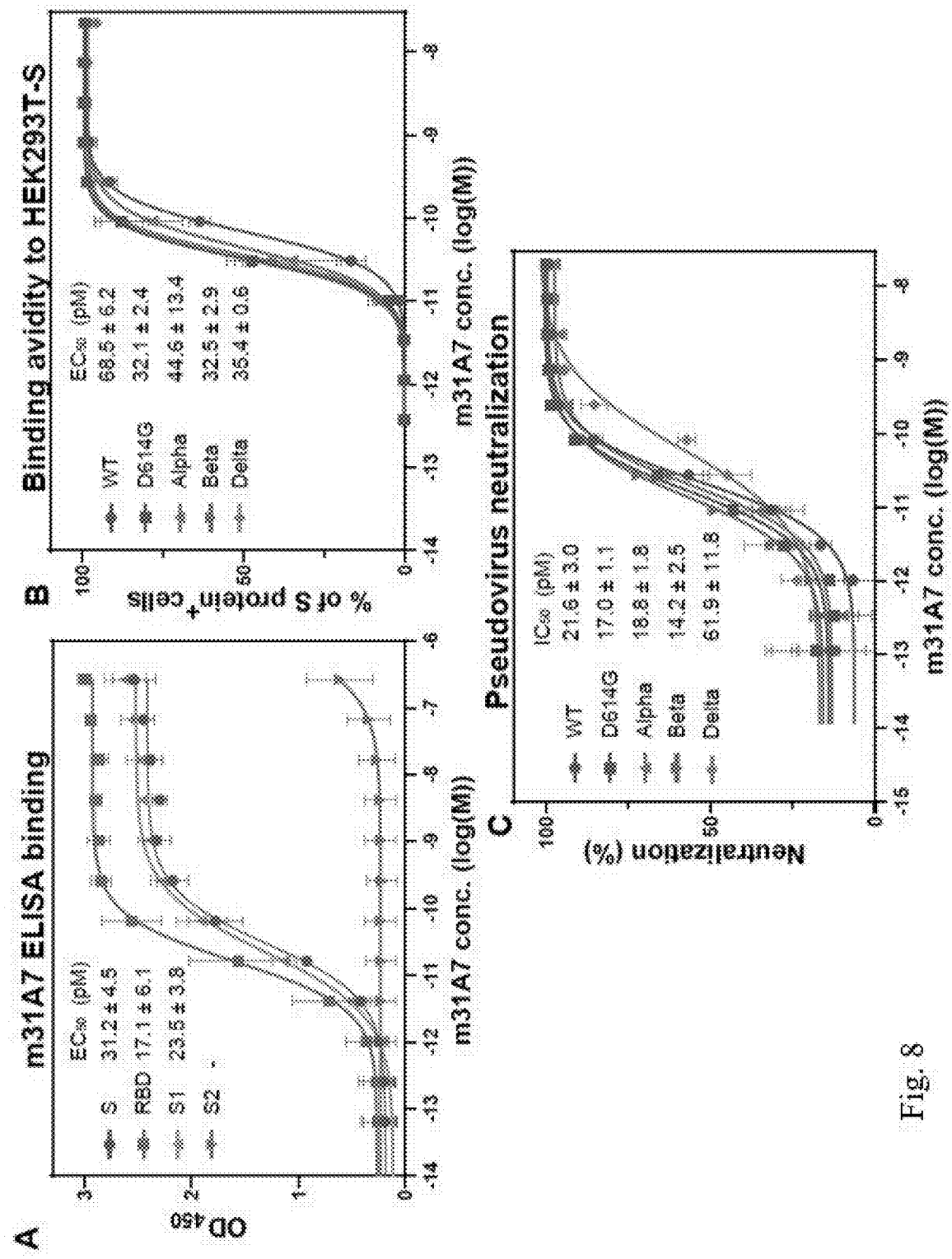
FIGS. 8 (A) to (L). Functional, prophylactic, and structural characterization of antibody m31A7 elicited by $S_{MG}$ vaccination indicates cross-neutralizing capacity. (A) ELISA binding of m31A7 to S1, S2, RBD, or the entire S ectodomain. (B) Flow cytometry analysis of m31A7 binding to HEK293T cells expressing S protein of SARS-CoV-2 WT and variants. (C) Neutralization activity of m31A7 against pseudoviruses carrying WT or variant S proteins. Data of three technical replicates for (A), (B), and (C) are shown as means±SD and curves fit by nonlinear regression for EC$_{50}$ values. (D) Antibody injection and challenge schedule for K18-hACE2 transgenic mice (n=3) is shown. (E and F) Weight change (E) and body temperature change (F) are shown for mice treated with m31A7 or PBS. Data are presented as means±SEM. (G) Binding kinetics of m31A7 IgG and Fab to S protein are presented, with dissociation constants (K$_d$) shown above. (H) Epitope mapping by HDX-MS of m31A7 is shown in a time course revealing two peptide candidates, 419-433 and 471-482, with greater than 10% ΔHDX at 15 s. Data are shown as means±SD and analyzed by multiple t tests at each time point. *P<0.05; P<0.01; *P<0.001; ****P<0.0001. (I) The cryo-EM map fitted with m31A7-Fab/S protein complex structure is shown. Heavy chain, dark green; light chain, light green; RBD, red; NTD, orange; the rest of S1, light gray; S2, dark gray; and N-glycans, blue. (J) An enlarged view of RBD-m31A7 interface is shown. The star marks the vicinity between m31A7 light chain and N165-glycan. (K) Superimposition of previously reported mAbs S2E12 (magenta), COV253 (pink), and B1-182.1 (light blue) (PDB 7BEN, 7K4N, and 7MLZ) onto the m31A7-bound RBD (gray). The receptor binding motif and RBD tip are highlighted. (L) A footprint comparison of COV253 (pink) and m31A7 (green) on RBD (gray) shows similarity, with residues of VOCs labeled and drawn as red spheres.
Figure 8:
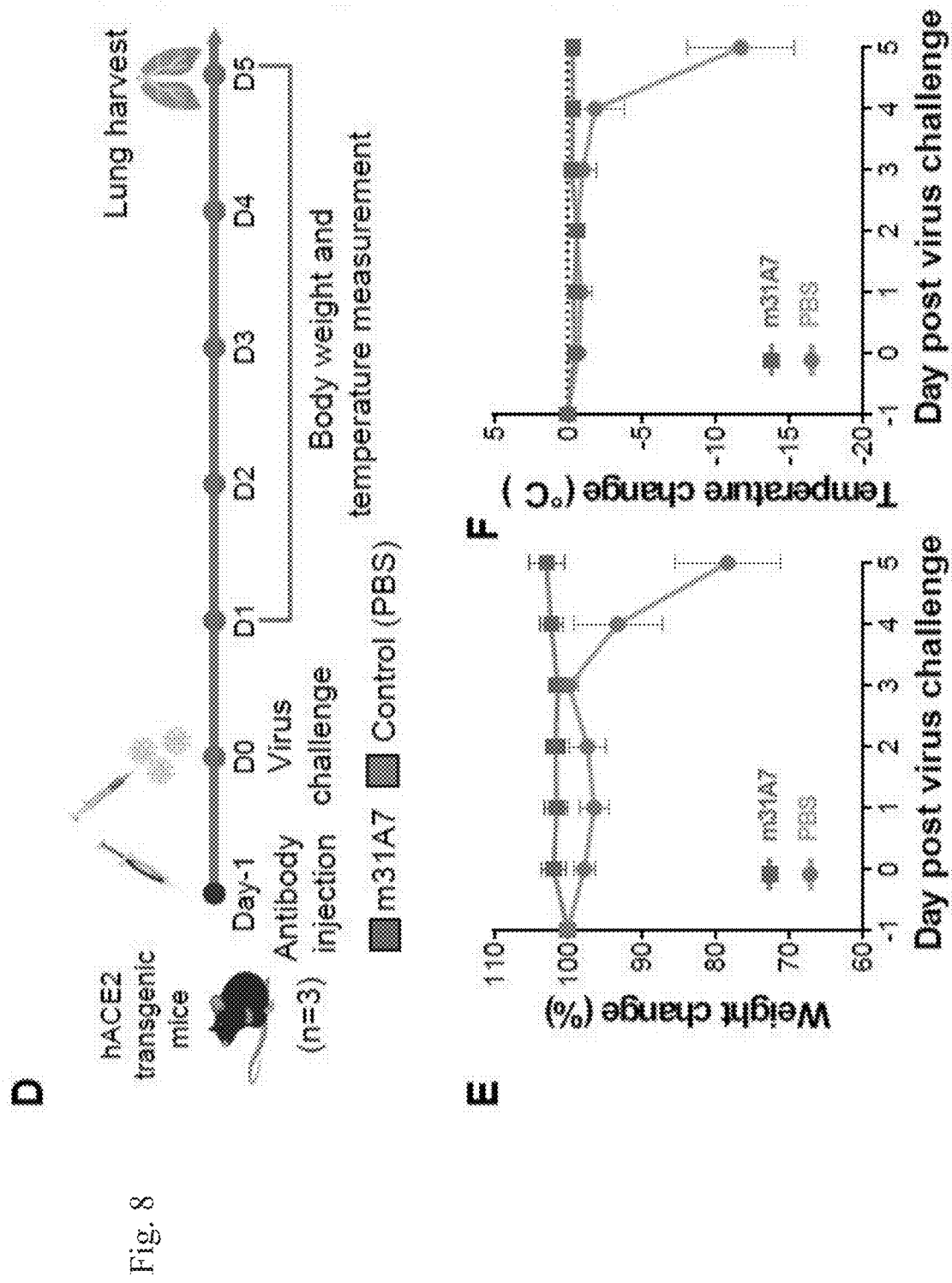
Figure 8:
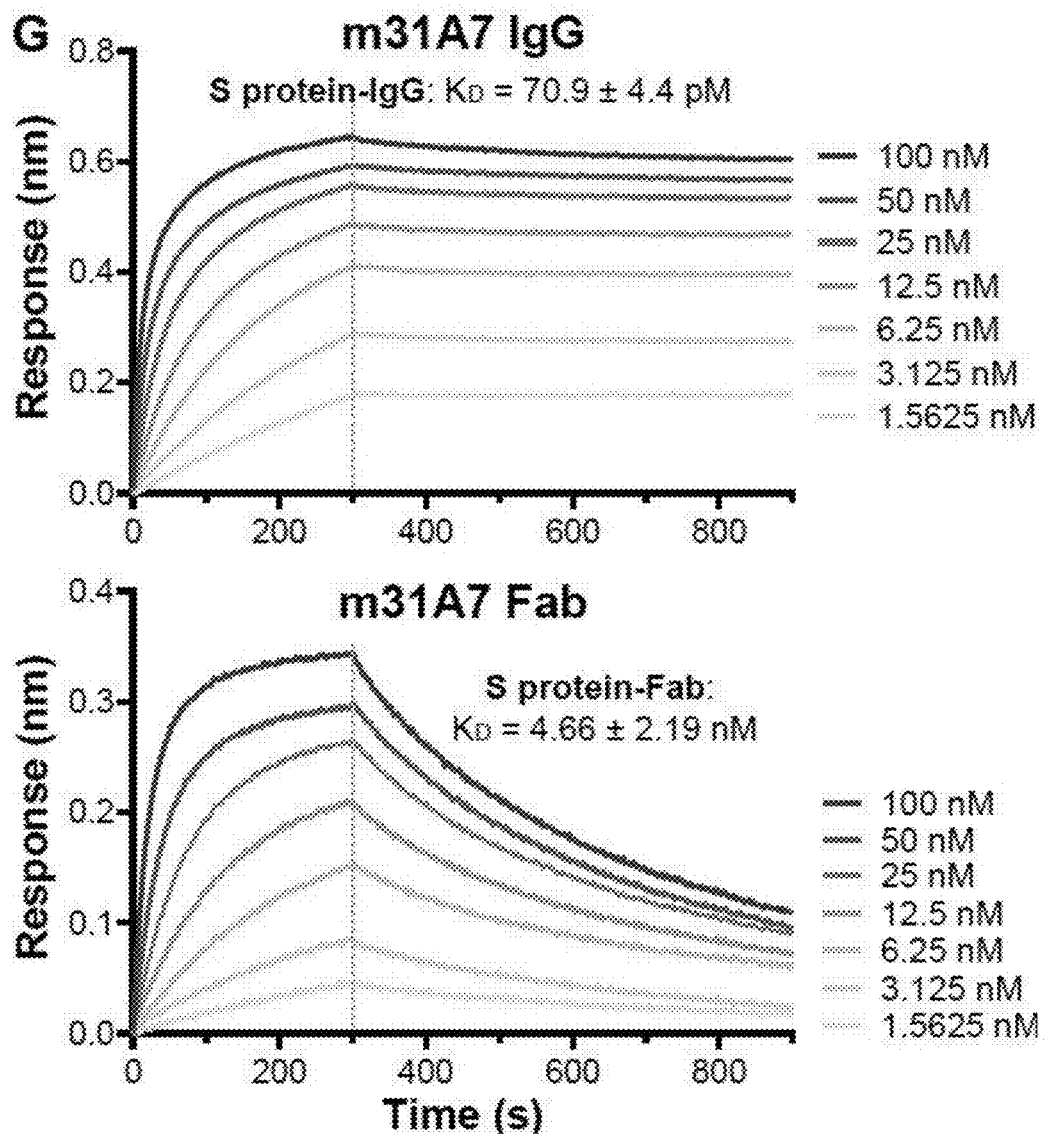
Figure 8:
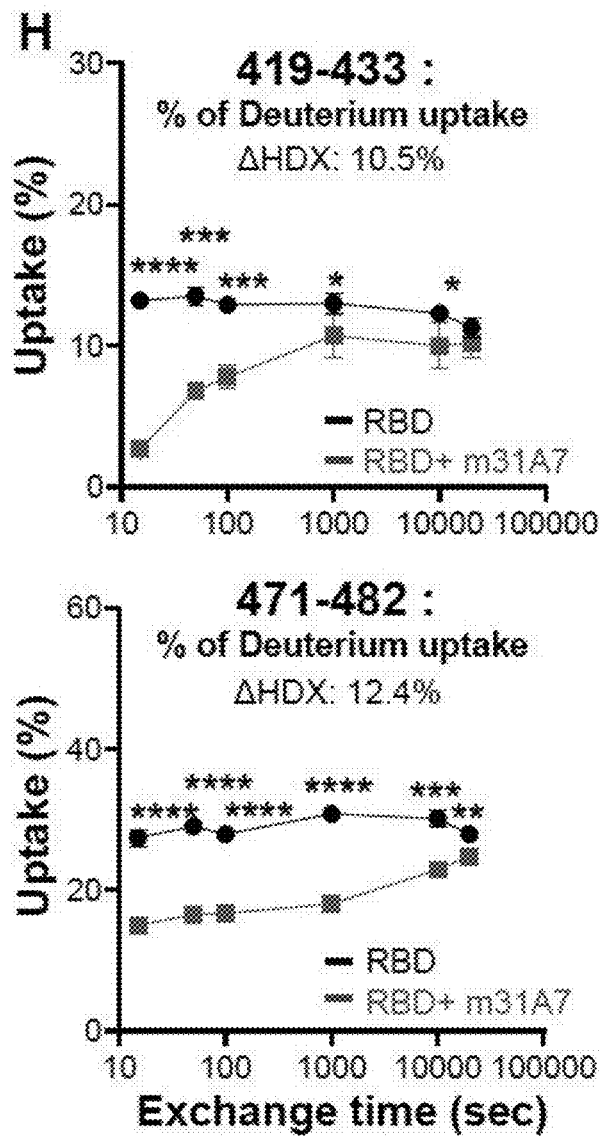
Figure 8:
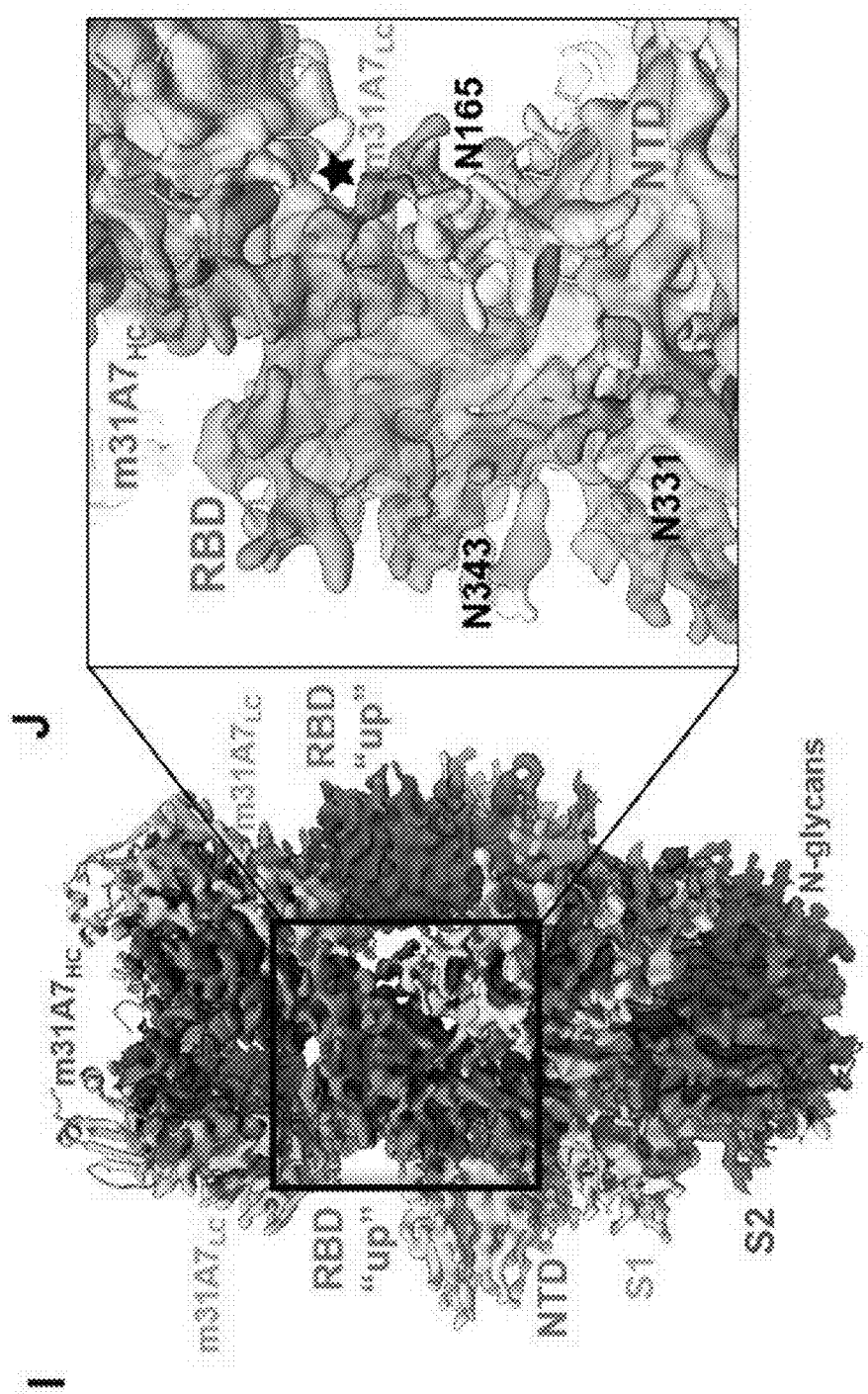
Figure 8:
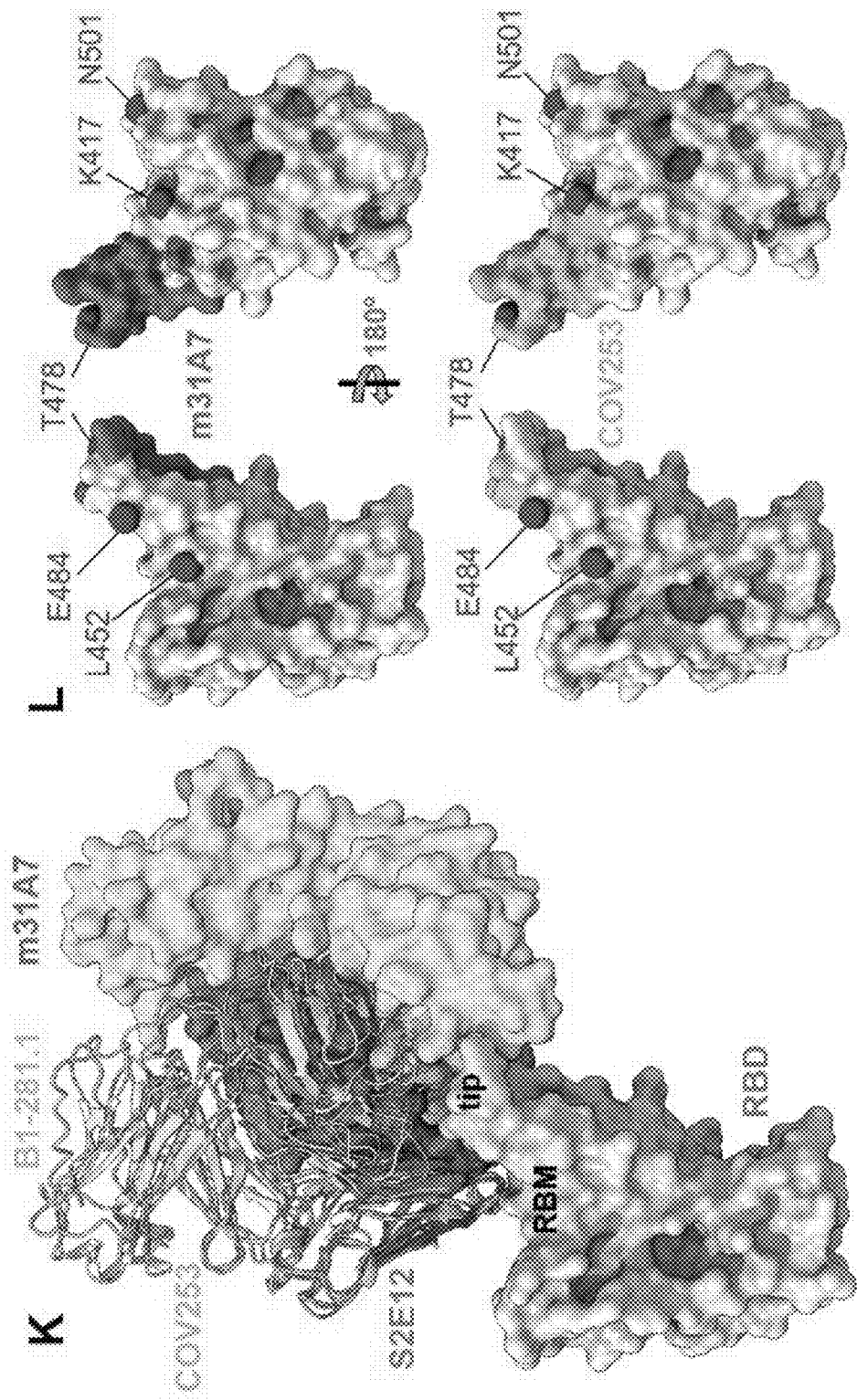

Example 21: A Broadly Neutralizing Antibody was Isolated from B Cells of Mice Immunized with S$_{MG}$ The sorting of S protein-specific B cells from S$_{MG}$-immunized mice led to the identification of a monoclonal antibody (mAb) m31A7 from the IGHV1-18 amplified clones, a subset that is uniquely abundant in S$_{MG}$-immunized B cell repertoire (FIG. 8O). This mAb interacts with the full-length S protein, S1, and RBD, but not S2 (FIG. 8A), and binds to HEK293T cells that express the S protein from different SARS-CoV-2 variants (FIG. 8B). In addition, m31A7 was shown to neutralize various pseudovirus variants (WT, D614G, alpha, beta, and delta) at subpicomolar half-maximal inhibitory concentration (IC$_{50}$) up to 1000-fold higher than the reported human mAb EY6A (FIG. 8C). A prophylactic study also demonstrated good in vivo efficacy of m31A7 in K18-hACE2 mice (n=3) challenged with WT SARS-CoV-2 (FIG. 8D). Prophylactically treated mice maintained both body weight and temperature (FIG. 8, E and F). Biolayer interferometry (BLI) analysis was used to measure the dissociation constants of m31A7 and its Fab binding to S protein at 70.9 pM and 4.66 nM, respectively (FIG. 8G). Epitope mapping by hydrogen-deuterium exchange mass spectrometry (HDX-MS) revealed its potential binding regions on RBD (FIG. 8H), which overlapped with the observed epitope in the crystal structure of RBD in complex with m31A7-Fab. The cryo-electron microscopy (EM) structure further clarified the binding of m31A7 only to RBD in the "up" state (FIG. 8I), with the N165-glycan from neighboring NTD in the vicinity of the RBD-m31A7 interface (FIG. 8J). The footprint of m31A7 on the RBD is similar to that of human VH1-58 class mAbs (FIG. 8K), but it approaches the RBD from a different angle, with shifted local contact areas on the tip loop, bypassing most of key mutated residues of VOCs such as E484 and K417, but not T478 (FIG. 8L). The detailed RBD-m31A7 interface and the inhibitory mechanism of this S$_{MG}$-elicited mAb are under further investigation.

Example 22: Delta S$_{MG}$ Vaccination Elicited More Neutralizing Antibodies Against SARS-CoV-2 Variant Pseudovirus S$_{MG}$ protein expression construct of SARS-CoV-2 Delta variant

SEQ ID NO: 3

MFVFLVLLPLVSSQCVNLRTRTQLPPAYTNSFTRGVYYPDKVFRSSVLHSTQDLFLPFFSNVTW

FHAIHVSGTNGTKRFDNPVLPFNDGVYFASTEKSNIIRGWIFGTTLDSKTQSLLIVNNATNVVIKVCEFQ

FCNDPFLDVYYHKNNKSWMESGVYSSANNCTFEYVSQPFLMDLEGKQGNFKNLREFVFKNIDGYFKIYSK

HTPINLVRDLPQGFSALEPLVDLPIGINITRFQTLLALHRSYLTPGDSSSGWTAGAAAYYVGYLQPRTFL

LKYNENGTITDAVDCALDPLSETKCTLKSFTVEKGIYQTSNFRVQPTESIVRFPNITNLCPFGEVENATR

FASVYAWNRKRISNCVADYSVLYNSASFSTFKCYGVSPTKLNDLCFTNVYADSFVIRGDEVRQIAPGQTG

KIADYNYKLPDDFTGCVIAWNSNNLDSKVGGNYNYRYRLFRKSNLKPFERDISTEIYQAGSKPCNGVEGF

NCYFPLQSYGFQPTNGVGYQPYRVVVLSFELLHAPATVCGPKKSTNLVKNKCVNFNFNGLTGTGVLTESN

KKFLPFQQFGRDIADTTDAVRDPQTLEILDITPCSFGGVSVITPGTNTSNQVAVLYQGVNCTEVPVAIHA

DQLTPTWRVYSTGSNVFQTRAGCLIGAEHVNNSYECDIPIGAGICASYQTQTNSRGSAGSVASQSIIAYT

MSLGAENSVAYSNNSIAIPTNFTISVTTEILPVSMTKTSVDCTMYICGDSTECSNLLLQYGSFCTQLNRA

LTGIAVEQDKNTQEVFAQVKQIYKTPPIKDFGGFNFSQILPDPSKPSKRSFIEDLLFNKVTLADAGFIKQ

YGDCLGDIAARDLICAQKFNGLTVLPPLLTDEMIAQYTSALLAGTITSGWTFGAGAALQIPFAMQMAYRF

NGIGVTQNVLYENQKLIANQFNSAIGKIQDSLSSTASALGKLQNVVNQNAQALNTLVKQLSSNFGAISSV

LNDILSRLDPPEAEVQIDRLITGRLQSLQTYVTQQLIRAAEIRASANLAATKMSECVLGQSKRVDFCGKG

-continued

```
YHLMSFPQSAPHGVVFLHVTYVPAQEKNFTTAPAICHDGKAHFPREGVFVSNGTHWFVTQRNFYEPQIIT

TDNTFVSGNCDVVIGIVNNTVYDPLQPELDSFKEELDKYFKNHTSPDVDLGDISGINASVVNIQKEIDRL

NEVAKNLNESLIDLQELGKYEQDIRSLVPRGSPGSGYIPEAPRDGQAYVRKDGEWVLLSTFLGGSGSLEV

LFQGPHHHHHH
```

Signal peptide from A/Brisbane/59/2007(H1N1)):

(SEQ ID NO: 4)

MKVKLLVLLCTFTATYAGT

Thrombin cleavage site:

(SEQ ID NO: 5)

LVPRGS (SEQ ID NO: 6)

T4 foldon: PGSGYIPEAPRDGQAYVRKDGEWVLLSTFLG

HRV3C cleavage site:

(SEQ ID NO: 7)

GSGSLEVLFQGP (SEQ ID NO: 8)

His tag: HHHHHH

Figure 9:
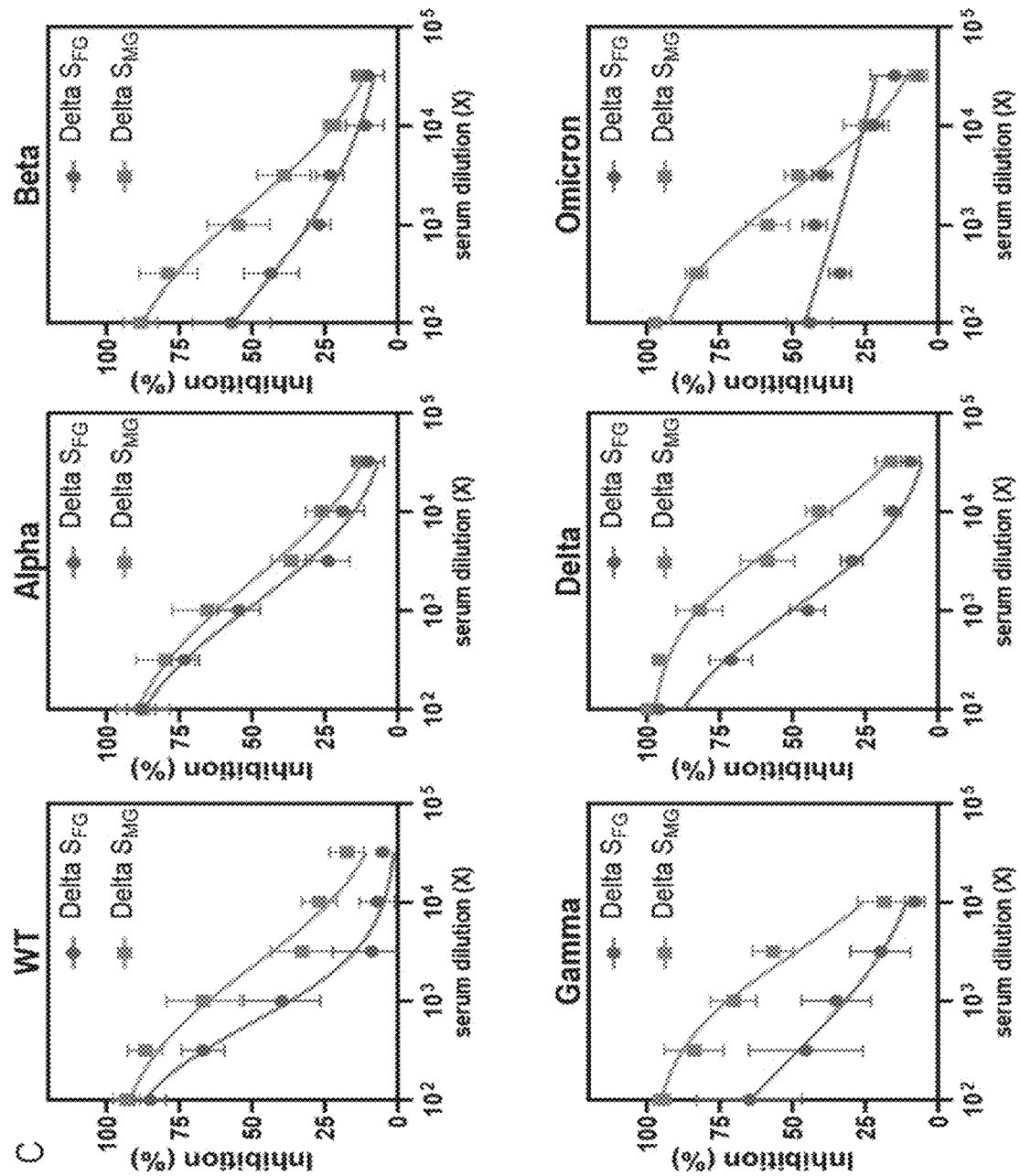
FIGS. 9 (A) to (C). Delta $S_{MG}$ vaccination elicited more neutralizing antibodies against SARS-CoV-2 variant pseudovirus. (A) Scheme of the vaccination. BALB/c mice (n=5) were immunized twice at week 0 and week 2 with Delta $S_{FG}$ or $S_{MG}$ vaccine. Sera were collected at week 6 and subsequently tested the neutralization ability using pseudovirus assay. (B) The 50 percent reciprocal neutralization titer (pNT50) of the sera against SARS-CoV-2 variant pseudovirus including wildtype (WH01) and variants of concern (VOCs) including Alpha, Beta, Gamma, Delta, and Omicron. The data were shown as mean (indicated above each bar)±SEM and analyzed by two-sided Mann-Whitney U-test to compare two experimental groups. *P<0.05. (C) The inhibition (%) of the SARS-CoV-2 variant pseudovirus cell infection provided by differently diluted serum. The data were shown as mean±SEM and the curves were fitted by nonlinear regression using Graph Prism 9.0.

BALB/c mice (n=5) were immunized twice at week 0 and week 2 with Delta $S_{FG}$ or $S_{MG}$ vaccine. Sera were collected at week 6 and subsequently tested the neutralization ability using pseudovirus assay (FIG. 9A). Pseudotyped viruses of SARS-CoV-2 Delta variants were used to gauge the ability to neutralize infections from the vaccine immunized sera. Again, the sera from $S_{MG}$ immunization possess superior neutralization ability towards WT, Alpha, Beta, Gamma, Delta and Omicron pseudoviruses. Their respective titers of Delta $S_{FG}$ vs. $S_{MG}$ (pNT50, higher is better) are 1018 vs. 3336 (against WT pseudovirus), 1396 vs. 2680 (against Alpha pseudovirus), 337 vs. 2282 (against Beta pseudovirus), 814 vs 4424 (against Gamma pseudovirus), 1138 vs. 6680 (against Delta pseudovirus) and 144 vs. 2628 (against Omicron pseudovirus), respectively.

Figure 10:
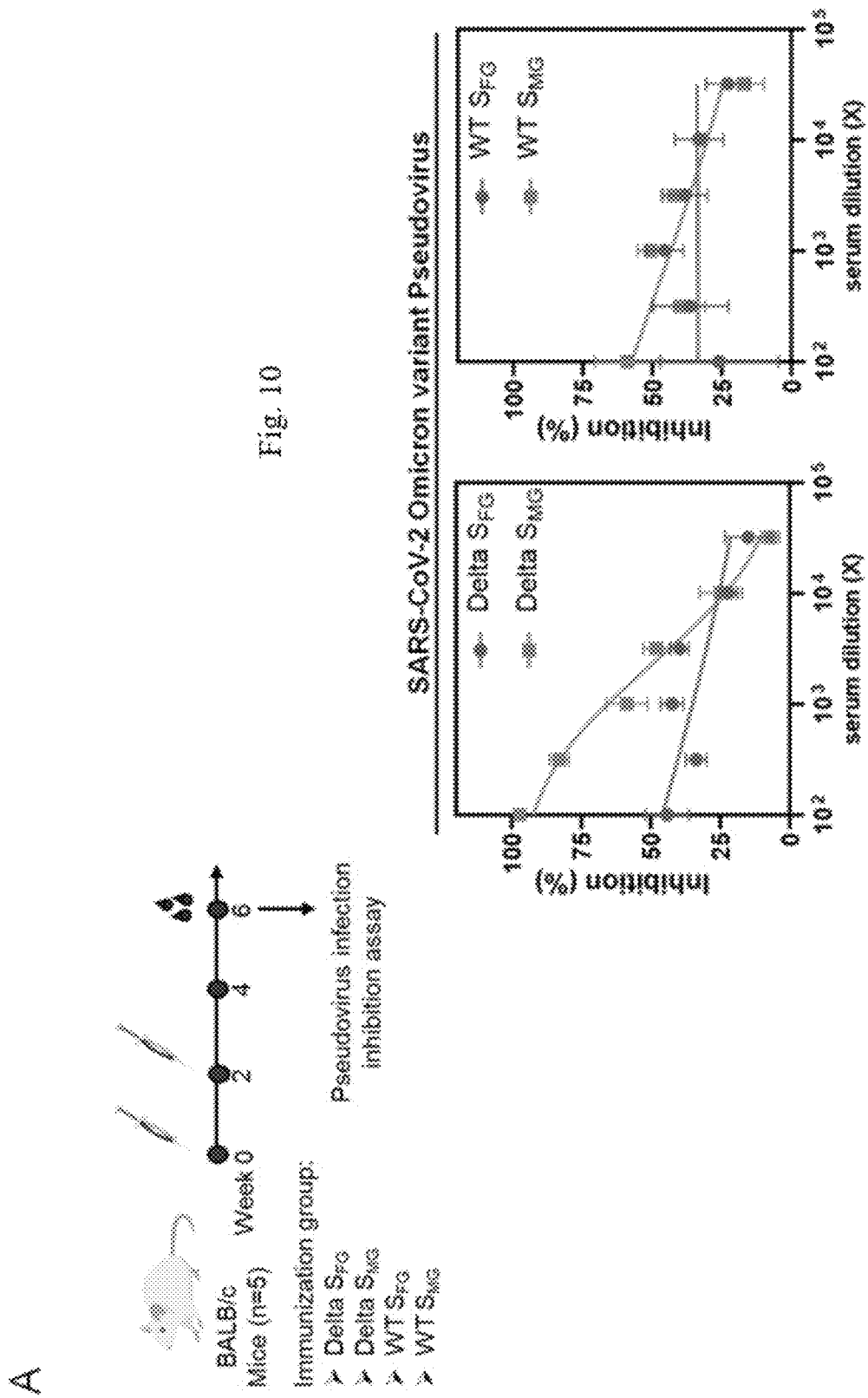
FIGS. 10 (A) and (B). Delta or WT $S_{MG}$ vaccination elicited more neutralizing antibodies against SARS-CoV-2 Omicron variant pseudovirus. (A) Scheme of the vaccination. BALB/c mice (n=5) were immunized twice at week 0 and week 2 with Delta/WT $S_{FG}$ or $S_{MG}$ vaccine. Sera were collected at week 6 and subsequently tested the neutralization ability using pseudovirus assay. (B) The inhibition (%) of the SARS-CoV-2 variant pseudovirus cell infection provided by differently diluted serum. The data were shown as mean±SEM and the curves were fitted by nonlinear regression using Graph Prism 9.0.

Example 23: Delta or WT $S_{MG}$ Vaccination Elicited More Neutralizing Antibodies Against SARS-CoV-2 Omicron Variant Pseudovirus BALB/c mice (n=5) were immunized twice at week 0 and week 2 with Delta/WT $S_{FG}$ or $S_{MG}$ vaccine. Sera were collected at week 6 and subsequently tested the neutralization ability using pseudovirus assay (FIG. 10A). Pseudotyped viruses of SARS-CoV-2 Omicron variant were used to gauge the ability to neutralize infections from the vaccine immunized sera from either WT $S_{FG}/S_{MG}$ or Delta $S_{FG}/S_{MG}$. WT $S_{FG}$ vaccination elicits no neutralization against Omicron pseudovirus, while WT $S_{MG}$ provides slight protection. Similarly, Delta $S_{FG}$ vaccination elicits little neutralization against Omicron pseudovirus infection, however, Delta $S_{MG}$ provides excellent neutralization.

Figure 11:
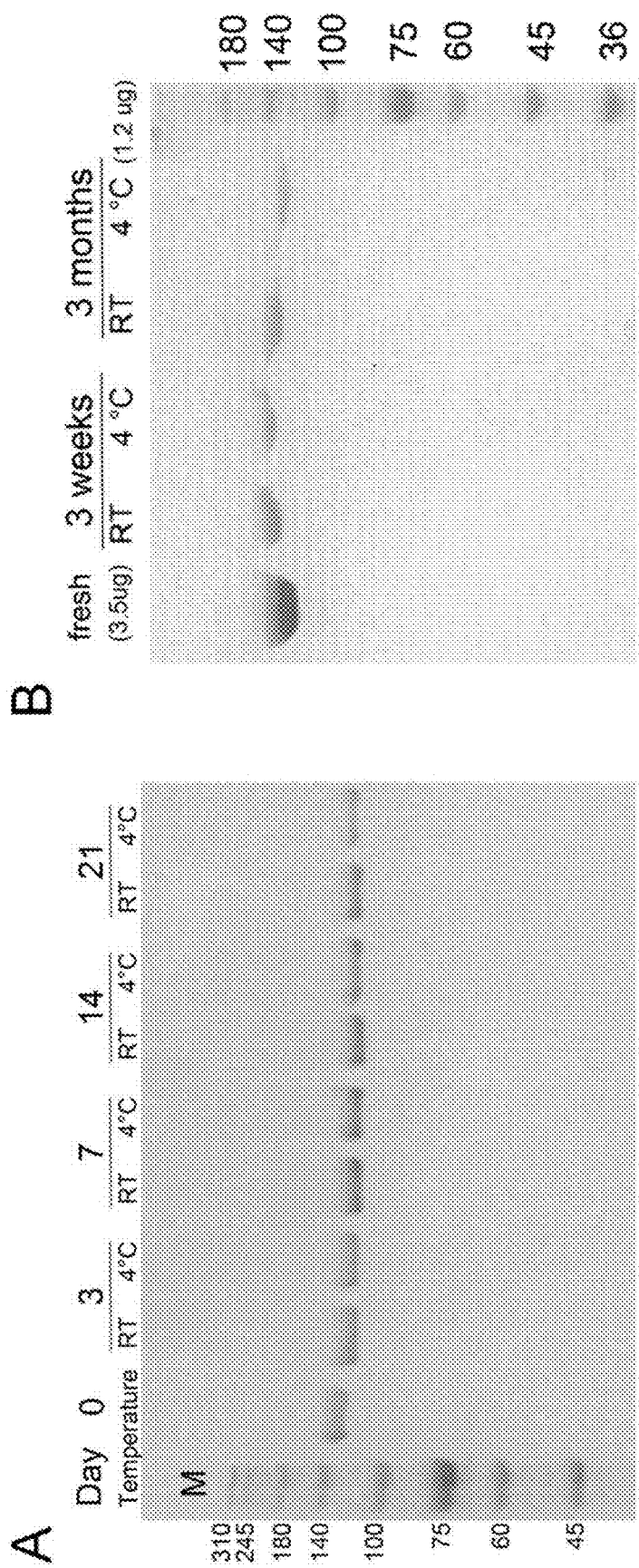
FIGS. 11 (A) to (C). Delta $S_{MG}$ protein can be stored at room temperature in solution or in powder. (A and B) Delta $S_{MG}$ protein in phosphate-buffered saline additive with two amino acids (pbs-aa), 50 mM L-Arginine and 50 mM L-Glutamate, was filtered with 0.22 μm filter and stored at room temperature (RT) or 4° C. The proteins were collected at different time points including 3, 7, 14, 21 days and 3 months. The collected samples were mixed with 5×SDS-PAGE Loading Dye, heated at 100° C. for 5 min and stored in the 4° C. until gel running. (C) Delta $S_{MG}$ protein storage test in different buffers and lyophilization conditions. The PBS with or without 50 mM L-Arginine and 50 mM L-Glutamate was tested for storing delta $S_{HM}$ or $S_{MG}$ (first 3 lanes) at 4° C. The delta $S_{MG}$ was tested lyophilization with or without excipient and store at RT for over 2 weeks (last 2 lanes).
Figure 11:
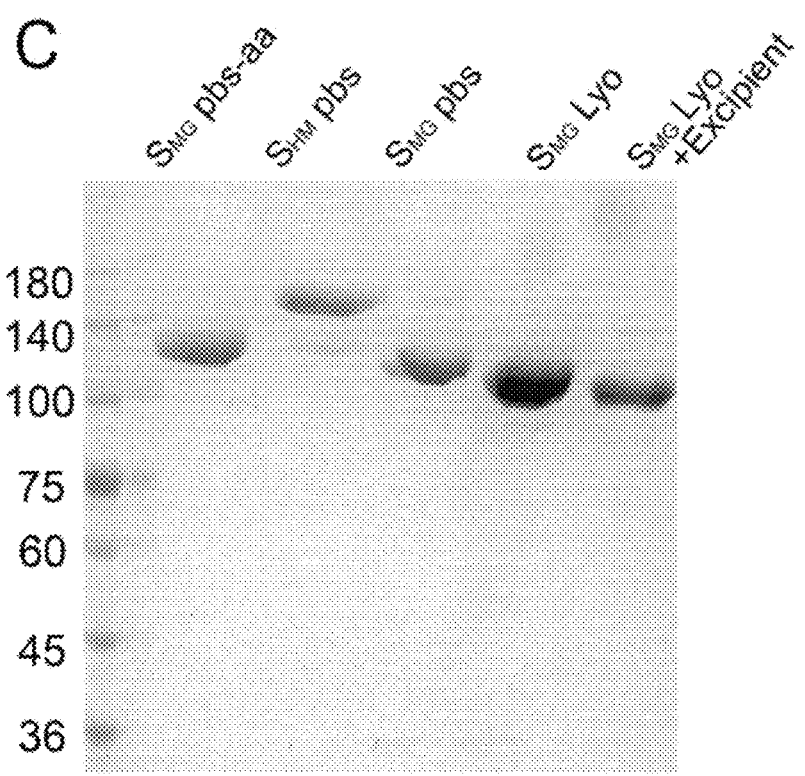
Figure 12:
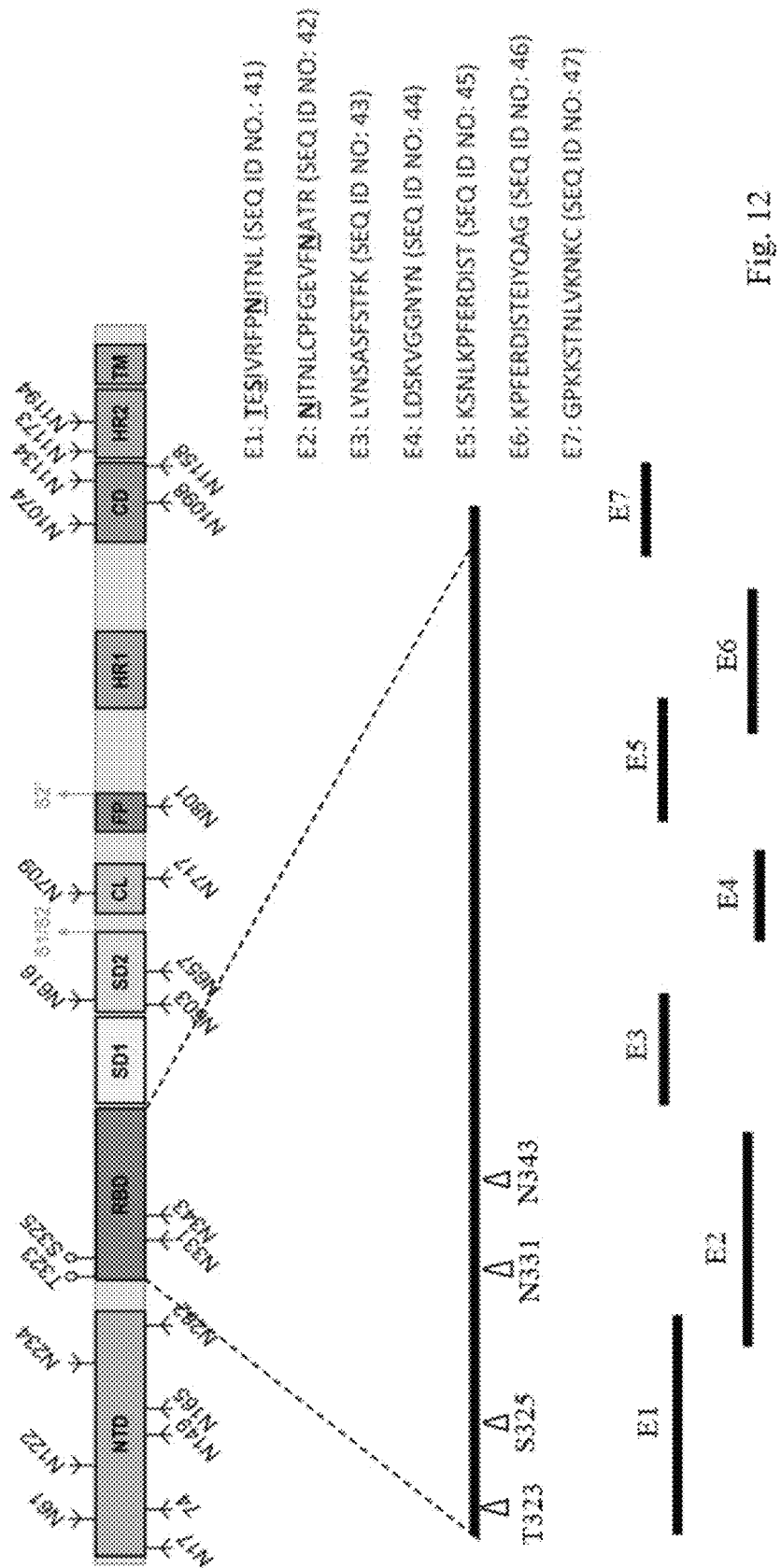
FIG. 12 shows a schematic representation of highly conserved epitopes (E1, E2, E3, E4, E5, E6 and E7) (SEQ ID NOs: 41-47) present in the receptor-binding domain (RBD) of a SARS-CoV-2 spike protein containing N-terminal domain (NTD), a receptor-binding domain (RBD), a fusion peptide (FP), heptapeptide repeat sequence 1 (HR1), heptapeptide repeat sequence 2 (HR2), transmembrane domain (TM), cytoplasm domain (CD), and S2 subunit.
Figure 13:
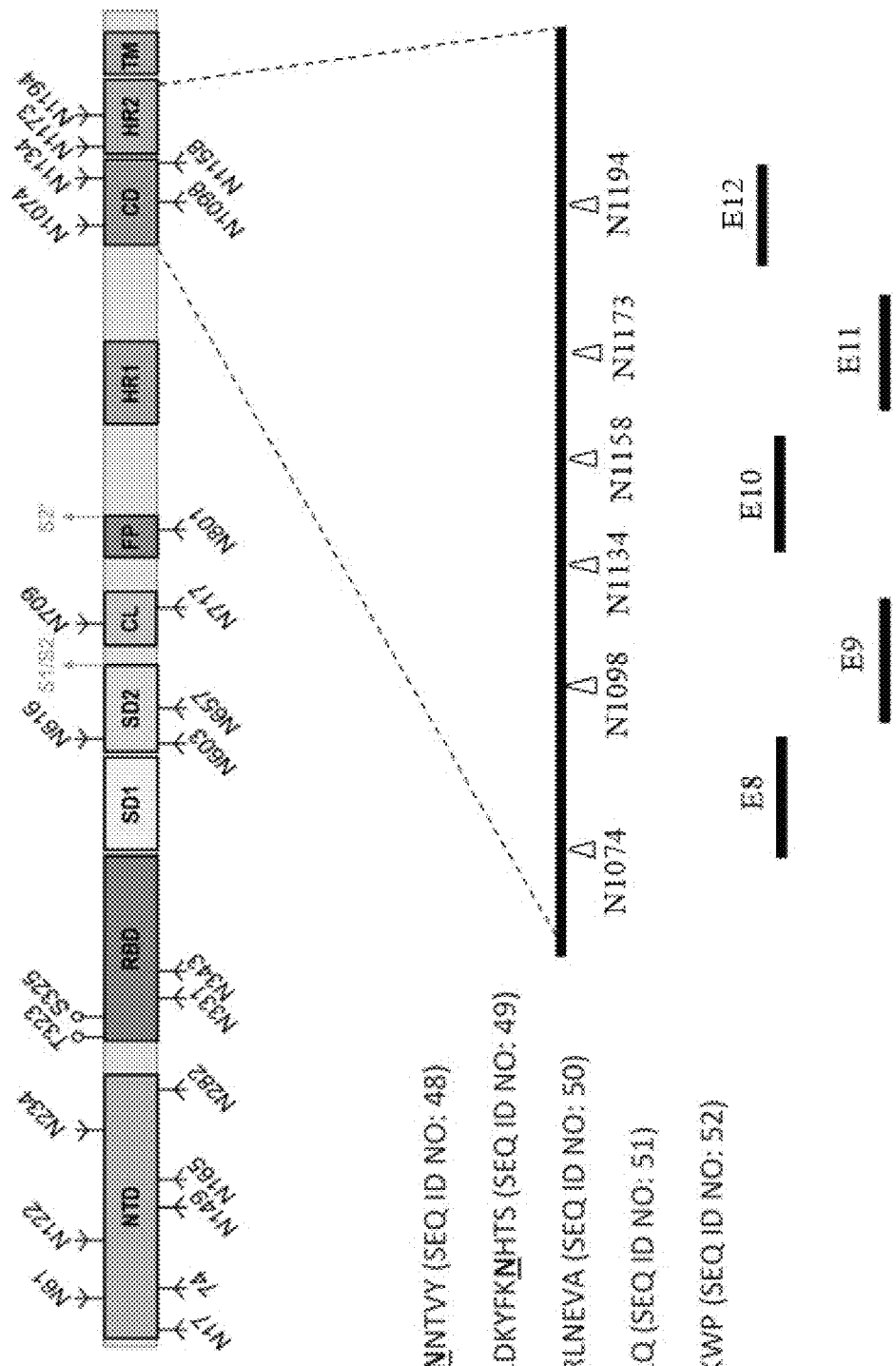
FIG. 13 shows a schematic representation of highly conserved epitopes (E8, E9, E10, E11, E12) (SEQ ID NOs: 48-52) present in the heptapeptide repeat sequence 2 (H1R2) of a SARS-CoV-2 spike protein.

Example 24: Delta $S_{MG}$ Protein can be Stored at Room Temperature in Solution or in Powder Delta $S_{MG}$ protein in phosphate-buffered saline additive with two amino acids (pbs-aa), 50 mM L-Arginine and 50 mM L-Glutamate, was filtered with 0.22 μm filter and stored at room temperature (RT) or 4° C. The proteins were collected at different time points including 3, 7, 14, 21 days and 3 months. The collected samples were mixed with 5×SDS-PAGE Loading Dye, heated at 100° C. for 5 min and stored in the 4° C. until gel running (FIG. 11 A and B). The PBS with or without 50 mM L-Arginine and 50 mM L-Glutamate was tested for storing delta $S_{HM}$ or $S_{MG}$ (first 3 lanes) at 4° C. The delta $S_{MG}$ was tested lyophilization with or without excipient and store at RT for over 2 weeks (last 2 lanes) (FIG. 11 C). The stability test indicates Delta $S_{MG}$ protein can be stored in solution and is stable at either room temperature or 4 degree C. for at least 21 days. Moreover, Delta $S_{MG}$ can be lyophilized and stored at RT and remain stable for at least 3 months.

Sequences

SEQ ID NO: 1

```
QCVNLTTRTQLPPAYTNSFTRGVYYPDKVFRSSVLHSTQDLFLPFFSNVTWFHAIHV

SGTNGTKRFDNPVLPFNDGVYFASTEKSNIIRGWIFGTTLDSKTQSLLIVNNATNVV

IKVCEFQFCNDPFLGVYYHKNNKSWMESEFRVYSSANNCTFEYVSQPFLMDLEGKQG

NFKNLREFVFKNIDGYFKIYSKHTPINLVRDLPQGFSALEPLVDLPIGINITRFQTL

LALHRSYLTPGDSSSGWTAGAAAYYVGYLQPRTELLKYNENGTITDAVDCALDPLSE

TKCTLKSFTVEKGIYQTSNERVQPTESIVRFPNITNLCPFGEVFNATRFASVYAWNR

KRISNCVADYSVLYNSASFSTFKCY

GQTGKIADYNYKLPDDFTGCVIAWNSNNLDSKVGGNYNYLYRLERKSNLKPFERDIS

TEIYQAGSTPCNGVEGENCYFPLQSYGFQPTNGVGYQPYRVVVLSFELLHAPATVCG

PKKSTNLVKNKCVNFNFNGLTGTGVLTESNKKELPFQQFGRDIADTTDAVRDPQTLE

ILDITPCSFGGVSVITPGTNTSNQVAVLYQDVNCTEVPVAIHADQLTPTWRVYSTGS

NVFQTRAGCLIGAEHVNNSYECDIPIGAGICASYQTQTNSPRRARSVASQSIIAYTM

SLGAENSVAYSNNSIAIPTNFTISVTTEILPVSMTKTSVDCTMYICGDSTECSNLLL

QYGSFCTQLNRALTGIAVEQDKNTQEVFAQVKQIYKTPPIKDFGGENFSQILPDPSK

PSKRSFIEDLLENKVTLADAGFIKQYGDCLGDIAARDLICAQKENGLTVLPPLLTDE

MIAQYTSALLAGTITSGWTFGAGAALQIPFAMQMAYRENGIGVTQNVLYENQKLIAN

QFNSAIGKIQDSLSSTASALGKLQDVVNQNAQALNTLVKQLSSNFGAISSVLNDILS

RLDKVEAEVQIDRLITGRLQSLQTYVTQQLIRAAEIRASANLAATKMSECVLGQSKR

VDFCGKGYHLMSFPQSAPHGVVFLHVTYVPAQEKNFTTAPAICHDGKAHFPREGVFV

SNGTHWFVTQRNFYEPQIITTDNTFVSGNCDVVIGIVNNTVYDPLQPELDSFKEELD

KYFKNHTSPDVDLGDISGINASVVNIQKEIDRLNEVAKNLNESLIDLQELGKYEQY

SEQ ID NO: 2

QCVNLRTRTQLPPAYTNSFTRGVYPDKVFRSSVLHSTQDLFLPFFSNVTWFHAIHV

SGTNGTKRFDNPVLPFNDGVYFASTEKSNIIRGWIFGTTLDSKTQSLLIVNNATNVVIKVCEFQ

FCNDPFLDVYYHKNNKSWMESGVYSSANNCTFEYVSQPFLMDLEGKQGNFKNLREFVFKNIDGY

FKIYSKHTPINLVRDLPQGFSALEPLVDLPIGINITRFQTLLALHRSYLTPGDSSSGWTAGAAA

YYVGYLQPRTFLLKYNENGTITDAVDCALDPLSETKCTLKSFTVEKGIYQTSNERVQPTESIVR

FPNITNLCPFGEVFNATRFASVYAWNRKRISNCVADYSVLYNSASFSTFKCYGVSPTKLNDLCF

TNVYADSFVIRGDEVRQIAPGQTGKIADYNYKLPDDFTGCVIAWNSNNLDSKVGGNYNYRYRLF

RKSNLKPFERDISTEIYQAGSKPCNGVEGENCYFPLQSYGFQPTNGVGYQPYRVVVLSFELLHA

PATVCGPKKSTNLVKNKCVNFNFNGLTGTGVLTESNKKFLPFQQFGRDIADTTDAVRDPQTLEI

LDITPCSFGGVSVITPGTNTSNQVAVLYQGVNCTEVPVAIHADQLTPTWRVYSTGSNVFQTRAG

CLIGAEHVNNSYECDIPIGAGICASYQTQTNSRGSAGSVASQSIIAYTMSLGAENSVAYSNNSI

AIPTNFTISVTTEILPVSMTKTSVDCTMYICGDSTECSNLLLQYGSFCTQLNRALTGIAVEQDK

NTQEVFAQVKQIYKTPPIKDFGGFNFSQILPDPSKPSKRSFIEDLLENKVTLADAGFIKQYGDC

LGDIAARDLICAQKENGLTVLPPLLTDEMIAQYTSALLAGTITSGWTFGAGAALQIPFAMQMAY

RFNGIGVTQNVLYENQKLIANQFNSAIGKIQDSLSSTASALGKLQNVVNQNAQALNTLVKQLSS

NFGAISSVLNDILSRLDPPEAEVQIDRLITGRLQSLQTYVTQQLIRAAEIRASANLAATKMSEC

VLGQSKRVDFCGKGYHLMSFPQSAPHGVVFLHVTYVPAQEKNFTTAPAICHDGKAHFPREGVEV

SNGTHWFVTQRNFYEPQIITTDNTFVSGNCDVVIGIVNNTVYDPLQPELDSFKEELDKYFKNHT

SPDVDLGDISGINASVVNIQKEIDRLNEVAKNLNESLIDLQELGKYEQ $S_{MG}$ Protein Expression Construct of SARS-CoV-2 Delta Variant

SEQ ID NO: 3

MKVKLLVLLCTFTATYAGTQCVNLRTRTQLPPAYTNSFTRGVYYPDKVFRSSVLHSTQ

DLFLPFFSNVTWFHAIHVSGTNGTKRFDNPVLPFNDGVYFASTEKSNIIRGWIFGTTLDSK

-continued

TQSLLIVNNATNVVIKVCEFQFCNDPFLDVYYHKNNKSWMESGVYSSANNCTFEYVSQ
PFLMDLEGKQGNFKNLREFVFKNIDGYFKIYSKHTPINLVRDLPQGFSALEPLVDLPIGIN
ITRFQTLLALHRSYLTPGDSSSGWTAGAAAYYVGYLQPRTFLLKYNENGTITDAVDCAL
DPLSETKCTLKSFTVEKGIYQTSNFRVQPTESIVRFPNITNLCPFGEVENATRFASVYAWN
RKRISNCVADYSVLYNSASFSTFKCYGVSPTKLNDLCFTNVYADSFVIRGDEVRQIAPGQ
TGKIADYNYKLPDDFTGCVIAWNSNNLDSKVGGNYNYRYRLFRKSNLKPFERDISTEIY
QAGSKPCNGVEGENCYFPLQSYGFQPTNGVGYQPYRVVVLSFELLHAPATVCGPKKST
NLVKNKCVNFNFNGLTGTGVLTESNKKFLPFQQFGRDIADTTDAVRDPQTLEILDITPCS
FGGVSVITPGTNTSNQVAVLYQGVNCTEVPVAIHADQLTPTWRVYSTGSNVFQTRAGC
LIGAEHVNNSYECDIPIGAGICASYQTQTNSRGSAGSVASQSIIAYTMSLGAENSVAYSN
NSIAIPTNFTISVTTEILPVSMTKTSVDCTMYICGDSTECSNLLLQYGSFCTQLNRALTGIA
VEQDKNTQEVFAQVKQIYKTPPIKDFGGFNFSQILPDPSKPSKRSFIEDLLFNKVTLADAG
FIKQYGDCLGDIAARDLICAQKFNGLTVLPPLLTDEMIAQYTSALLAGTITSGWTFGAGA
ALQIPFAMQMAYRENGIGVTQNVLYENQKLIANQFNSAIGKIQDSLSSTASALGKLQNV
VNQNAQALNTLVKQLSSNFGAISSVLNDILSRLDPPEAEVQIDRLITGRLQSLQTYVTQQ
LIRAAEIRASANLAATKMSECVLGQSKRVDFCGKGYHLMSFPQSAPHGVVFLHVTYVP
AQEKNFTTAPAICHDGKAHFPREGVFVSNGTHWFVTQRNFYEPQIITTDNTFVSGNCDV
VIGIVNNTVYDPLQPELDSFKEELDKYFKNHTSPDVDLGDISGINASVVNIQKEIDRLNEV
AKNLNESLIDLQELGKYEQDIRS<u>LVPRGS</u><u>PGSGYIPEAPRDGQAYVRKDGEWVLLSTFLG</u>
<u>GSGSLEVLFQGP</u>HHHHHH

Signal peptide modified from A/Brisbane/59/2007(H1N1)
(SEQ ID NO: 4)
MKVKLLVLLCTFTATYAGT Thrombin cleavage site
(SEQ ID NO: 5)
LVPRGS T4 foldon
(SEQ ID NO: 6)
PGSGYIPEAPRDGQAYVRKDGEWVLLSTFLG HRV3C cleavage site
(SEQ ID NO: 7)
GSGSLEVLFQGP His tag
(SEQ ID NO: 8)
HHHHHH Residues replacing the original furin cleavage site
(SEQ ID NO: 9)
GSAG Highly conserved epitopes
(SEQ ID NO.: 41)
TESIVRFPNITNL (SEQ ID NO: 42)
NITNLCPFGEVENATR (SEQ ID NO: 43)
LYNSASFSTFK (SEQ ID NO: 44)
LDSKVGGNYN (SEQ ID NO: 45)
KSNLKPFERDIST -continued

KPFERDISTEIYQAG (SEQ ID NO: 46)

GPKKSTNLVKNKC (SEQ ID NO: 47)

NCDVVIGIVNNTVY (SEQ ID NO: 48)

PELDSFKEELDKYFKNHTS (SEQ ID NO: 49)

VNIQKEIDRLNEVA (SEQ ID NO: 50)

NLNESLIDLQ (SEQ ID NO: 51)

LGKYEQYIKWP (SEQ ID NO: 52)

---

SEQUENCE LISTING

<160> NUMBER OF SEQ ID NOS: 52

<210> SEQ ID NO 1
<211> LENGTH: 1196
<212> TYPE: PRT
<213> ORGANISM: SARS-CoV-2

<400> SEQUENCE: 1

```
Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
            20                  25                  30

Ser Val Leu His Ser Thr Gln Asp Leu Phe Leu Pro Phe Phe Ser Asn
        35                  40                  45

Val Thr Trp Phe His Ala Ile His Val Ser Gly Thr Asn Gly Thr Lys
    50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
            100                 105                 110

Val Val Ile Lys Val Cys Glu Phe Gln Phe Cys Asn Asp Pro Phe Leu
        115                 120                 125

Gly Val Tyr Tyr His Lys Asn Asn Lys Ser Trp Met Glu Ser Glu Phe
    130                 135                 140

Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
                165                 170                 175

Arg Glu Phe Val Phe Lys Asn Ile Asp Gly Tyr Phe Lys Ile Tyr Ser
            180                 185                 190

Lys His Thr Pro Ile Asn Leu Val Arg Asp Leu Pro Gln Gly Phe Ser
        195                 200                 205

Ala Leu Glu Pro Leu Val Asp Leu Pro Ile Gly Ile Asn Ile Thr Arg
    210                 215                 220

Phe Gln Thr Leu Leu Ala Leu His Arg Ser Tyr Leu Thr Pro Gly Asp
225                 230                 235                 240
```

-continued

```
Ser Ser Ser Gly Trp Thr Ala Gly Ala Ala Ala Tyr Tyr Val Gly Tyr
            245                 250                 255

Leu Gln Pro Arg Thr Phe Leu Leu Lys Tyr Asn Glu Asn Gly Thr Ile
            260                 265                 270

Thr Asp Ala Val Asp Cys Ala Leu Asp Pro Leu Ser Glu Thr Lys Cys
            275                 280                 285

Thr Leu Lys Ser Phe Thr Val Glu Lys Gly Ile Tyr Gln Thr Ser Asn
            290                 295                 300

Phe Arg Val Gln Pro Thr Glu Ser Ile Val Arg Phe Pro Asn Ile Thr
305                 310                 315                 320

Asn Leu Cys Pro Phe Gly Glu Val Phe Asn Ala Thr Arg Phe Ala Ser
                    325                 330                 335

Val Tyr Ala Trp Asn Arg Lys Arg Ile Ser Asn Cys Val Ala Asp Tyr
                    340                 345                 350

Ser Val Leu Tyr Asn Ser Ala Ser Phe Ser Thr Phe Lys Cys Tyr Gly
                    355                 360                 365

Val Ser Pro Thr Lys Leu Asn Asp Leu Cys Phe Thr Asn Val Tyr Ala
                    370                 375                 380

Asp Ser Phe Val Ile Arg Gly Asp Glu Val Arg Gln Ile Ala Pro Gly
385                 390                 395                 400

Gln Thr Gly Lys Ile Ala Asp Tyr Asn Tyr Lys Leu Pro Asp Asp Phe
                    405                 410                 415

Thr Gly Cys Val Ile Ala Trp Asn Ser Asn Asn Leu Asp Ser Lys Val
                    420                 425                 430

Gly Gly Asn Tyr Asn Tyr Leu Tyr Arg Leu Phe Arg Lys Ser Asn Leu
                    435                 440                 445

Lys Pro Phe Glu Arg Asp Ile Ser Thr Glu Ile Tyr Gln Ala Gly Ser
            450                 455                 460

Thr Pro Cys Asn Gly Val Glu Gly Phe Asn Cys Tyr Phe Pro Leu Gln
465                 470                 475                 480

Ser Tyr Gly Phe Gln Pro Thr Asn Gly Val Gly Tyr Gln Pro Tyr Arg
                    485                 490                 495

Val Val Val Leu Ser Phe Glu Leu Leu His Ala Pro Ala Thr Val Cys
                    500                 505                 510

Gly Pro Lys Lys Ser Thr Asn Leu Val Lys Asn Lys Cys Val Asn Phe
                    515                 520                 525

Asn Phe Asn Gly Leu Thr Gly Thr Gly Val Leu Thr Glu Ser Asn Lys
            530                 535                 540

Lys Phe Leu Pro Phe Gln Gln Phe Gly Arg Asp Ile Ala Asp Thr Thr
545                 550                 555                 560

Asp Ala Val Arg Asp Pro Gln Thr Leu Glu Ile Leu Asp Ile Thr Pro
                    565                 570                 575

Cys Ser Phe Gly Gly Val Ser Val Ile Thr Pro Gly Thr Asn Thr Ser
                    580                 585                 590

Asn Gln Val Ala Val Leu Tyr Gln Asp Val Asn Cys Thr Glu Val Pro
                    595                 600                 605

Val Ala Ile His Ala Asp Gln Leu Thr Pro Thr Trp Arg Val Tyr Ser
                    610                 615                 620

Thr Gly Ser Asn Val Phe Gln Thr Arg Ala Gly Cys Leu Ile Gly Ala
625                 630                 635                 640

Glu His Val Asn Asn Ser Tyr Glu Cys Asp Ile Pro Ile Gly Ala Gly
                    645                 650                 655

Ile Cys Ala Ser Tyr Gln Thr Gln Thr Asn Ser Pro Arg Arg Ala Arg
```

-continued

```
                660                 665                 670
Ser Val Ala Ser Gln Ser Ile Ile Ala Tyr Thr Met Ser Leu Gly Ala
                675                 680                 685
Glu Asn Ser Val Ala Tyr Ser Asn Asn Ser Ile Ala Ile Pro Thr Asn
    690                 695                 700
Phe Thr Ile Ser Val Thr Thr Glu Ile Leu Pro Val Ser Met Thr Lys
705                 710                 715                 720
Thr Ser Val Asp Cys Thr Met Tyr Ile Cys Gly Asp Ser Thr Glu Cys
                725                 730                 735
Ser Asn Leu Leu Leu Gln Tyr Gly Ser Phe Cys Thr Gln Leu Asn Arg
                740                 745                 750
Ala Leu Thr Gly Ile Ala Val Glu Gln Asp Lys Asn Thr Gln Glu Val
                755                 760                 765
Phe Ala Gln Val Lys Gln Ile Tyr Lys Thr Pro Pro Ile Lys Asp Phe
            770                 775                 780
Gly Gly Phe Asn Phe Ser Gln Ile Leu Pro Asp Pro Ser Lys Pro Ser
785                 790                 795                 800
Lys Arg Ser Phe Ile Glu Asp Leu Leu Phe Asn Lys Val Thr Leu Ala
                805                 810                 815
Asp Ala Gly Phe Ile Lys Gln Tyr Gly Asp Cys Leu Gly Asp Ile Ala
                820                 825                 830
Ala Arg Asp Leu Ile Cys Ala Gln Lys Phe Asn Gly Leu Thr Val Leu
            835                 840                 845
Pro Pro Leu Leu Thr Asp Glu Met Ile Ala Gln Tyr Thr Ser Ala Leu
            850                 855                 860
Leu Ala Gly Thr Ile Thr Ser Gly Trp Thr Phe Gly Ala Gly Ala Ala
865                 870                 875                 880
Leu Gln Ile Pro Phe Ala Met Gln Met Ala Tyr Arg Phe Asn Gly Ile
                885                 890                 895
Gly Val Thr Gln Asn Val Leu Tyr Glu Asn Gln Lys Leu Ile Ala Asn
                900                 905                 910
Gln Phe Asn Ser Ala Ile Gly Lys Ile Gln Asp Ser Leu Ser Ser Thr
            915                 920                 925
Ala Ser Ala Leu Gly Lys Leu Gln Asp Val Val Asn Gln Asn Ala Gln
            930                 935                 940
Ala Leu Asn Thr Leu Val Lys Gln Leu Ser Ser Asn Phe Gly Ala Ile
945                 950                 955                 960
Ser Ser Val Leu Asn Asp Ile Leu Ser Arg Leu Asp Lys Val Glu Ala
                965                 970                 975
Glu Val Gln Ile Asp Arg Leu Ile Thr Gly Arg Leu Gln Ser Leu Gln
            980                 985                 990
Thr Tyr Val Thr Gln Gln Leu Ile Arg Ala Ala Glu Ile Arg Ala Ser
            995                 1000                1005
Ala Asn Leu Ala Ala Thr Lys Met Ser Glu Cys Val Leu Gly Gln
    1010                1015                1020
Ser Lys Arg Val Asp Phe Cys Gly Lys Gly Tyr His Leu Met Ser
    1025                1030                1035
Phe Pro Gln Ser Ala Pro His Gly Val Val Phe Leu His Val Thr
    1040                1045                1050
Tyr Val Pro Ala Gln Glu Lys Asn Phe Thr Thr Ala Pro Ala Ile
    1055                1060                1065
Cys His Asp Gly Lys Ala His Phe Pro Arg Glu Gly Val Phe Val
    1070                1075                1080
```

```
Ser Asn Gly Thr His Trp Phe Val Thr Gln Arg Asn Phe Tyr Glu
    1085            1090                1095

Pro Gln Ile Ile Thr Thr Asp Asn Thr Phe Val Ser Gly Asn Cys
    1100            1105                1110

Asp Val Val Ile Gly Ile Val Asn Asn Thr Val Tyr Asp Pro Leu
    1115            1120                1125

Gln Pro Glu Leu Asp Ser Phe Lys Glu Glu Leu Asp Lys Tyr Phe
    1130            1135                1140

Lys Asn His Thr Ser Pro Asp Val Asp Leu Gly Asp Ile Ser Gly
    1145            1150                1155

Ile Asn Ala Ser Val Val Asn Ile Gln Lys Glu Ile Asp Arg Leu
    1160            1165                1170

Asn Glu Val Ala Lys Asn Leu Asn Glu Ser Leu Ile Asp Leu Gln
    1175            1180                1185

Glu Leu Gly Lys Tyr Glu Gln Tyr
    1190            1195

<210> SEQ ID NO 2
<211> LENGTH: 1193
<212> TYPE: PRT
<213> ORGANISM: SARS-CoV-2

<400> SEQUENCE: 2

Gln Cys Val Asn Leu Arg Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
                20                  25                  30

Ser Val Leu His Ser Thr Gln Asp Leu Phe Leu Pro Phe Phe Ser Asn
            35                  40                  45

Val Thr Trp Phe His Ala Ile His Val Ser Gly Thr Asn Gly Thr Lys
        50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
            100                 105                 110

Val Val Ile Lys Val Cys Glu Phe Gln Phe Cys Asn Asp Pro Phe Leu
        115                 120                 125

Asp Val Tyr Tyr His Lys Asn Asn Lys Ser Trp Met Glu Ser Gly Val
    130                 135                 140

Tyr Ser Ser Ala Asn Asn Cys Thr Phe Glu Tyr Val Ser Gln Pro Phe
145                 150                 155                 160

Leu Met Asp Leu Glu Gly Lys Gln Gly Asn Phe Lys Asn Leu Arg Glu
                165                 170                 175

Phe Val Phe Lys Asn Ile Asp Gly Tyr Phe Lys Ile Tyr Ser Lys His
            180                 185                 190

Thr Pro Ile Asn Leu Val Arg Asp Leu Pro Gln Gly Phe Ser Ala Leu
        195                 200                 205

Glu Pro Leu Val Asp Leu Pro Ile Gly Ile Asn Ile Thr Arg Phe Gln
    210                 215                 220

Thr Leu Leu Ala Leu His Arg Ser Tyr Leu Thr Pro Gly Asp Ser Ser
225                 230                 235                 240

Ser Gly Trp Thr Ala Gly Ala Ala Ala Tyr Tyr Val Gly Tyr Leu Gln
```

```
                        245                 250                 255
            Pro Arg Thr Phe Leu Lys Tyr Asn Glu Asn Gly Thr Ile Thr Asp
                        260                 265                 270
            Ala Val Asp Cys Ala Leu Asp Pro Leu Ser Glu Thr Lys Cys Thr Leu
                        275                 280                 285
            Lys Ser Phe Thr Val Glu Lys Gly Ile Tyr Gln Thr Ser Asn Phe Arg
                290                 295                 300
            Val Gln Pro Thr Glu Ser Ile Val Arg Phe Pro Asn Ile Thr Asn Leu
            305                 310                 315                 320
            Cys Pro Phe Gly Glu Val Phe Asn Ala Thr Arg Phe Ala Ser Val Tyr
                            325                 330                 335
            Ala Trp Asn Arg Lys Arg Ile Ser Asn Cys Val Ala Asp Tyr Ser Val
                        340                 345                 350
            Leu Tyr Asn Ser Ala Ser Phe Ser Thr Phe Lys Cys Tyr Gly Val Ser
                        355                 360                 365
            Pro Thr Lys Leu Asn Asp Leu Cys Phe Thr Asn Val Tyr Ala Asp Ser
                370                 375                 380
            Phe Val Ile Arg Gly Asp Glu Val Arg Gln Ile Ala Pro Gly Gln Thr
            385                 390                 395                 400
            Gly Lys Ile Ala Asp Tyr Asn Tyr Lys Leu Pro Asp Asp Phe Thr Gly
                            405                 410                 415
            Cys Val Ile Ala Trp Asn Ser Asn Asn Leu Asp Ser Lys Val Gly Gly
                        420                 425                 430
            Asn Tyr Asn Tyr Arg Tyr Arg Leu Phe Arg Lys Ser Asn Leu Lys Pro
                        435                 440                 445
            Phe Glu Arg Asp Ile Ser Thr Glu Ile Tyr Gln Ala Gly Ser Lys Pro
                450                 455                 460
            Cys Asn Gly Val Glu Gly Phe Asn Cys Tyr Phe Pro Leu Gln Ser Tyr
            465                 470                 475                 480
            Gly Phe Gln Pro Thr Asn Gly Val Gly Tyr Gln Pro Tyr Arg Val Val
                            485                 490                 495
            Val Leu Ser Phe Glu Leu Leu His Ala Pro Ala Thr Val Cys Gly Pro
                        500                 505                 510
            Lys Lys Ser Thr Asn Leu Val Lys Asn Lys Cys Val Asn Phe Asn Phe
                        515                 520                 525
            Asn Gly Leu Thr Gly Thr Gly Val Leu Thr Glu Ser Asn Lys Lys Phe
                530                 535                 540
            Leu Pro Phe Gln Gln Phe Gly Arg Asp Ile Ala Asp Thr Thr Asp Ala
            545                 550                 555                 560
            Val Arg Asp Pro Gln Thr Leu Glu Ile Leu Asp Ile Thr Pro Cys Ser
                            565                 570                 575
            Phe Gly Gly Val Ser Val Ile Thr Pro Gly Thr Asn Thr Ser Asn Gln
                        580                 585                 590
            Val Ala Val Leu Tyr Gln Gly Val Asn Cys Thr Glu Val Pro Val Ala
                        595                 600                 605
            Ile His Ala Asp Gln Leu Thr Pro Thr Trp Arg Val Tyr Ser Thr Gly
                610                 615                 620
            Ser Asn Val Phe Gln Thr Arg Ala Gly Cys Leu Ile Gly Ala Glu His
            625                 630                 635                 640
            Val Asn Asn Ser Tyr Glu Cys Asp Ile Pro Ile Gly Ala Gly Ile Cys
                            645                 650                 655
            Ala Ser Tyr Gln Thr Gln Thr Asn Ser Arg Gly Ser Ala Gly Ser Val
                        660                 665                 670
```

```
Ala Ser Gln Ser Ile Ile Ala Tyr Thr Met Ser Leu Gly Ala Glu Asn
            675                 680                 685

Ser Val Ala Tyr Ser Asn Asn Ser Ile Ala Ile Pro Thr Asn Phe Thr
690                 695                 700

Ile Ser Val Thr Thr Glu Ile Leu Pro Val Ser Met Thr Lys Thr Ser
705                 710                 715                 720

Val Asp Cys Thr Met Tyr Ile Cys Gly Asp Ser Thr Glu Cys Ser Asn
                725                 730                 735

Leu Leu Leu Gln Tyr Gly Ser Phe Cys Thr Gln Leu Asn Arg Ala Leu
            740                 745                 750

Thr Gly Ile Ala Val Glu Gln Asp Lys Asn Thr Gln Glu Val Phe Ala
            755                 760                 765

Gln Val Lys Gln Ile Tyr Lys Thr Pro Pro Ile Lys Asp Phe Gly Gly
770                 775                 780

Phe Asn Phe Ser Gln Ile Leu Pro Asp Pro Ser Lys Pro Ser Lys Arg
785                 790                 795                 800

Ser Phe Ile Glu Asp Leu Leu Phe Asn Lys Val Thr Leu Ala Asp Ala
                805                 810                 815

Gly Phe Ile Lys Gln Tyr Gly Asp Cys Leu Gly Asp Ile Ala Ala Arg
            820                 825                 830

Asp Leu Ile Cys Ala Gln Lys Phe Asn Gly Leu Thr Val Leu Pro Pro
            835                 840                 845

Leu Leu Thr Asp Glu Met Ile Ala Gln Tyr Thr Ser Ala Leu Leu Ala
850                 855                 860

Gly Thr Ile Thr Ser Gly Trp Thr Phe Gly Ala Gly Ala Ala Leu Gln
865                 870                 875                 880

Ile Pro Phe Ala Met Gln Met Ala Tyr Arg Phe Asn Gly Ile Gly Val
                885                 890                 895

Thr Gln Asn Val Leu Tyr Glu Asn Gln Lys Leu Ile Ala Asn Gln Phe
            900                 905                 910

Asn Ser Ala Ile Gly Lys Ile Gln Asp Ser Leu Ser Ser Thr Ala Ser
            915                 920                 925

Ala Leu Gly Lys Leu Gln Asn Val Val Asn Gln Asn Ala Gln Ala Leu
            930                 935                 940

Asn Thr Leu Val Lys Gln Leu Ser Ser Asn Phe Gly Ala Ile Ser Ser
945                 950                 955                 960

Val Leu Asn Asp Ile Leu Ser Arg Leu Asp Pro Pro Glu Ala Glu Val
                965                 970                 975

Gln Ile Asp Arg Leu Ile Thr Gly Arg Leu Gln Ser Leu Gln Thr Tyr
            980                 985                 990

Val Thr Gln Gln Leu Ile Arg Ala Ala Glu Ile Arg Ala Ser Ala Asn
            995                 1000                1005

Leu Ala Ala Thr Lys Met Ser Glu Cys Val Leu Gly Gln Ser Lys
    1010                1015                1020

Arg Val Asp Phe Cys Gly Lys Gly Tyr His Leu Met Ser Phe Pro
    1025                1030                1035

Gln Ser Ala Pro His Gly Val Val Phe Leu His Val Thr Tyr Val
    1040                1045                1050

Pro Ala Gln Glu Lys Asn Phe Thr Thr Ala Pro Ala Ile Cys His
    1055                1060                1065

Asp Gly Lys Ala His Phe Pro Arg Glu Gly Val Phe Val Ser Asn
    1070                1075                1080
```

-continued

```
Gly Thr  His Trp Phe Val Thr  Gln Arg Asn Phe Tyr  Glu Pro Gln
    1085                 1090                 1095

Ile Ile  Thr Thr Asp Asn Thr  Phe Val Ser Gly Asn  Cys Asp Val
    1100                 1105                 1110

Val Ile  Gly Ile Val Asn Asn  Thr Val Tyr Asp Pro  Leu Gln Pro
    1115                 1120                 1125

Glu Leu  Asp Ser Phe Lys Glu  Glu Leu Asp Lys Tyr  Phe Lys Asn
    1130                 1135                 1140

His Thr  Ser Pro Asp Val Asp  Leu Gly Asp Ile Ser  Gly Ile Asn
    1145                 1150                 1155

Ala Ser  Val Val Asn Ile Gln  Lys Glu Ile Asp Arg  Leu Asn Glu
    1160                 1165                 1170

Val Ala  Lys Asn Leu Asn Glu  Ser Leu Ile Asp Leu  Gln Glu Leu
    1175                 1180                 1185

Gly Lys  Tyr Glu Gln
    1190

<210> SEQ ID NO 3
<211> LENGTH: 1271
<212> TYPE: PRT
<213> ORGANISM: SARS-CoV-2 (Delta strain)

<400> SEQUENCE: 3

Met Lys Val Lys Leu Leu Val Leu Leu Cys Thr Phe Thr Ala Thr Tyr
1               5                   10                  15

Ala Gly Thr Gln Cys Val Asn Leu Arg Thr Arg Thr Gln Leu Pro Pro
            20                  25                  30

Ala Tyr Thr Asn Ser Phe Thr Arg Gly Val Tyr Tyr Pro Asp Lys Val
        35                  40                  45

Phe Arg Ser Ser Val Leu His Ser Thr Gln Asp Leu Phe Leu Pro Phe
    50                  55                  60

Phe Ser Asn Val Thr Trp Phe His Ala Ile His Val Ser Gly Thr Asn
65                  70                  75                  80

Gly Thr Lys Arg Phe Asp Asn Pro Val Leu Pro Phe Asn Asp Gly Val
                85                  90                  95

Tyr Phe Ala Ser Thr Glu Lys Ser Asn Ile Ile Arg Gly Trp Ile Phe
            100                 105                 110

Gly Thr Thr Leu Asp Ser Lys Thr Gln Ser Leu Leu Ile Val Asn Asn
        115                 120                 125

Ala Thr Asn Val Val Ile Lys Val Cys Glu Phe Gln Phe Cys Asn Asp
    130                 135                 140

Pro Phe Leu Asp Val Tyr Tyr His Lys Asn Asn Lys Ser Trp Met Glu
145                 150                 155                 160

Ser Gly Val Tyr Ser Ser Ala Asn Asn Cys Thr Phe Glu Tyr Val Ser
                165                 170                 175

Gln Pro Phe Leu Met Asp Leu Glu Gly Lys Gln Gly Asn Phe Lys Asn
            180                 185                 190

Leu Arg Glu Phe Val Phe Lys Asn Ile Asp Gly Tyr Phe Lys Ile Tyr
        195                 200                 205

Ser Lys His Thr Pro Ile Asn Leu Val Arg Asp Leu Pro Gln Gly Phe
    210                 215                 220

Ser Ala Leu Glu Pro Leu Val Asp Leu Pro Ile Gly Ile Asn Ile Thr
225                 230                 235                 240

Arg Phe Gln Thr Leu Leu Ala Leu His Arg Ser Tyr Leu Thr Pro Gly
                245                 250                 255
```

-continued

Asp Ser Ser Ser Gly Trp Thr Ala Gly Ala Ala Tyr Tyr Val Gly
            260                 265                 270

Tyr Leu Gln Pro Arg Thr Phe Leu Lys Tyr Asn Glu Asn Gly Thr
            275                 280                 285

Ile Thr Asp Ala Val Asp Cys Ala Leu Asp Pro Leu Ser Glu Thr Lys
            290                 295                 300

Cys Thr Leu Lys Ser Phe Thr Val Glu Lys Gly Ile Tyr Gln Thr Ser
305                 310                 315                 320

Asn Phe Arg Val Gln Pro Thr Glu Ser Ile Arg Phe Pro Asn Ile
            325                 330                 335

Thr Asn Leu Cys Pro Phe Gly Glu Val Phe Asn Ala Thr Arg Phe Ala
            340                 345                 350

Ser Val Tyr Ala Trp Asn Arg Lys Arg Ile Ser Asn Cys Val Ala Asp
            355                 360                 365

Tyr Ser Val Leu Tyr Asn Ser Ala Ser Phe Ser Thr Phe Lys Cys Tyr
            370                 375                 380

Gly Val Ser Pro Thr Lys Leu Asn Asp Leu Cys Phe Thr Asn Val Tyr
385                 390                 395                 400

Ala Asp Ser Phe Val Ile Arg Gly Asp Glu Val Arg Gln Ile Ala Pro
            405                 410                 415

Gly Gln Thr Gly Lys Ile Ala Asp Tyr Asn Tyr Lys Leu Pro Asp Asp
            420                 425                 430

Phe Thr Gly Cys Val Ile Ala Trp Asn Ser Asn Asn Leu Asp Ser Lys
            435                 440                 445

Val Gly Gly Asn Tyr Asn Tyr Arg Tyr Arg Leu Phe Arg Lys Ser Asn
            450                 455                 460

Leu Lys Pro Phe Glu Arg Asp Ile Ser Thr Glu Ile Tyr Gln Ala Gly
465                 470                 475                 480

Ser Lys Pro Cys Asn Gly Val Glu Gly Phe Asn Cys Tyr Phe Pro Leu
            485                 490                 495

Gln Ser Tyr Gly Phe Gln Pro Thr Asn Gly Val Gly Tyr Gln Pro Tyr
            500                 505                 510

Arg Val Val Val Leu Ser Phe Glu Leu Leu His Ala Pro Ala Thr Val
            515                 520                 525

Cys Gly Pro Lys Lys Ser Thr Asn Leu Val Lys Asn Lys Cys Val Asn
            530                 535                 540

Phe Asn Phe Asn Gly Leu Thr Gly Thr Gly Val Leu Thr Glu Ser Asn
545                 550                 555                 560

Lys Lys Phe Leu Pro Phe Gln Gln Phe Gly Arg Asp Ile Ala Asp Thr
            565                 570                 575

Thr Asp Ala Val Arg Asp Pro Gln Thr Leu Glu Ile Leu Asp Ile Thr
            580                 585                 590

Pro Cys Ser Phe Gly Gly Val Ser Val Ile Thr Pro Gly Thr Asn Thr
            595                 600                 605

Ser Asn Gln Val Ala Val Leu Tyr Gln Gly Val Asn Cys Thr Glu Val
            610                 615                 620

Pro Val Ala Ile His Ala Asp Gln Leu Thr Pro Thr Trp Arg Val Tyr
625                 630                 635                 640

Ser Thr Gly Ser Asn Val Phe Gln Thr Arg Ala Gly Cys Leu Ile Gly
            645                 650                 655

Ala Glu His Val Asn Asn Ser Tyr Glu Cys Asp Ile Pro Ile Gly Ala
            660                 665                 670

-continued

Gly Ile Cys Ala Ser Tyr Gln Thr Gln Thr Asn Ser Arg Gly Ser Ala
            675                 680                 685

Gly Ser Val Ala Ser Gln Ser Ile Ile Ala Tyr Thr Met Ser Leu Gly
690                 695                 700

Ala Glu Asn Ser Val Ala Tyr Ser Asn Asn Ser Ile Ala Ile Pro Thr
705                 710                 715                 720

Asn Phe Thr Ile Ser Val Thr Thr Glu Ile Leu Pro Val Ser Met Thr
                725                 730                 735

Lys Thr Ser Val Asp Cys Thr Met Tyr Ile Cys Gly Asp Ser Thr Glu
                740                 745                 750

Cys Ser Asn Leu Leu Leu Gln Tyr Gly Ser Phe Cys Thr Gln Leu Asn
            755                 760                 765

Arg Ala Leu Thr Gly Ile Ala Val Glu Gln Asp Lys Asn Thr Gln Glu
            770                 775                 780

Val Phe Ala Gln Val Lys Gln Ile Tyr Lys Thr Pro Pro Ile Lys Asp
785                 790                 795                 800

Phe Gly Gly Phe Asn Phe Ser Gln Ile Leu Pro Asp Pro Ser Lys Pro
                805                 810                 815

Ser Lys Arg Ser Phe Ile Glu Asp Leu Leu Phe Asn Lys Val Thr Leu
            820                 825                 830

Ala Asp Ala Gly Phe Ile Lys Gln Tyr Gly Asp Cys Leu Gly Asp Ile
            835                 840                 845

Ala Ala Arg Asp Leu Ile Cys Ala Gln Lys Phe Asn Gly Leu Thr Val
            850                 855                 860

Leu Pro Pro Leu Leu Thr Asp Glu Met Ile Ala Gln Tyr Thr Ser Ala
865                 870                 875                 880

Leu Leu Ala Gly Thr Ile Thr Ser Gly Trp Thr Phe Gly Ala Gly Ala
                885                 890                 895

Ala Leu Gln Ile Pro Phe Ala Met Gln Met Ala Tyr Arg Phe Asn Gly
            900                 905                 910

Ile Gly Val Thr Gln Asn Val Leu Tyr Glu Asn Gln Lys Leu Ile Ala
            915                 920                 925

Asn Gln Phe Asn Ser Ala Ile Gly Lys Ile Gln Asp Ser Leu Ser Ser
930                 935                 940

Thr Ala Ser Ala Leu Gly Lys Leu Gln Asn Val Val Asn Gln Asn Ala
945                 950                 955                 960

Gln Ala Leu Asn Thr Leu Val Lys Gln Leu Ser Ser Asn Phe Gly Ala
                965                 970                 975

Ile Ser Ser Val Leu Asn Asp Ile Leu Ser Arg Leu Asp Pro Pro Glu
            980                 985                 990

Ala Glu Val Gln Ile Asp Arg Leu Ile Thr Gly Arg Leu Gln Ser Leu
            995                 1000                1005

Gln Thr Tyr Val Thr Gln Gln Leu Ile Arg Ala Ala Glu Ile Arg
    1010                1015                1020

Ala Ser Ala Asn Leu Ala Ala Thr Lys Met Ser Glu Cys Val Leu
    1025                1030                1035

Gly Gln Ser Lys Arg Val Asp Phe Cys Gly Lys Gly Tyr His Leu
    1040                1045                1050

Met Ser Phe Pro Gln Ser Ala Pro His Gly Val Val Phe Leu His
    1055                1060                1065

Val Thr Tyr Val Pro Ala Gln Glu Lys Asn Phe Thr Thr Ala Pro
    1070                1075                1080

Ala Ile Cys His Asp Gly Lys Ala His Phe Pro Arg Glu Gly Val

```
                        1085                1090                1095

Phe Val Ser Asn Gly Thr His Trp Phe Val Thr Gln Arg Asn Phe
    1100                1105                1110

Tyr Glu Pro Gln Ile Ile Thr Thr Asp Asn Thr Phe Val Ser Gly
    1115                1120                1125

Asn Cys Asp Val Val Ile Gly Ile Val Asn Asn Thr Val Tyr Asp
    1130                1135                1140

Pro Leu Gln Pro Glu Leu Asp Ser Phe Lys Glu Leu Asp Lys
    1145                1150                1155

Tyr Phe Lys Asn His Thr Ser Pro Asp Val Asp Leu Gly Asp Ile
    1160                1165                1170

Ser Gly Ile Asn Ala Ser Val Val Asn Ile Gln Lys Glu Ile Asp
    1175                1180                1185

Arg Leu Asn Glu Val Ala Lys Asn Leu Asn Glu Ser Leu Ile Asp
    1190                1195                1200

Leu Gln Glu Leu Gly Lys Tyr Glu Gln Asp Ile Arg Ser Leu Val
    1205                1210                1215

Pro Arg Gly Ser Pro Gly Ser Gly Tyr Ile Pro Glu Ala Pro Arg
    1220                1225                1230

Asp Gly Gln Ala Tyr Val Arg Lys Asp Gly Glu Trp Val Leu Leu
    1235                1240                1245

Ser Thr Phe Leu Gly Gly Ser Gly Ser Leu Glu Val Leu Phe Gln
    1250                1255                1260

Gly Pro His His His His His His
    1265                1270

<210> SEQ ID NO 4
<211> LENGTH: 19
<212> TYPE: PRT
<213> ORGANISM: Artificial Sequence
<220> FEATURE:
<223> OTHER INFORMATION: Polypeptide

<400> SEQUENCE: 4

Met Lys Val Lys Leu Leu Val Leu Leu Cys Thr Phe Thr Ala Thr Tyr
1               5                   10                  15

Ala Gly Thr

<210> SEQ ID NO 5
<211> LENGTH: 6
<212> TYPE: PRT
<213> ORGANISM: Artificial Sequence
<220> FEATURE:
<223> OTHER INFORMATION: Polypeptide

<400> SEQUENCE: 5

Leu Val Pro Arg Gly Ser
1               5

<210> SEQ ID NO 6
<211> LENGTH: 31
<212> TYPE: PRT
<213> ORGANISM: Artificial Sequence
<220> FEATURE:
<223> OTHER INFORMATION: Polypeptide

<400> SEQUENCE: 6

Pro Gly Ser Gly Tyr Ile Pro Glu Ala Pro Arg Asp Gly Gln Ala Tyr
1               5                   10                  15
```

Val Arg Lys Asp Gly Glu Trp Val Leu Leu Ser Thr Phe Leu Gly
            20                  25                  30

<210> SEQ ID NO 7
<211> LENGTH: 12
<212> TYPE: PRT
<213> ORGANISM: Artificial Sequence
<220> FEATURE:
<223> OTHER INFORMATION: Polypeptide

<400> SEQUENCE: 7

Gly Ser Gly Ser Leu Glu Val Leu Phe Gln Gly Pro
1               5                   10

<210> SEQ ID NO 8
<211> LENGTH: 6
<212> TYPE: PRT
<213> ORGANISM: Artificial Sequence
<220> FEATURE:
<223> OTHER INFORMATION: Polypeptide

<400> SEQUENCE: 8

His His His His His His
1               5

<210> SEQ ID NO 9
<211> LENGTH: 4
<212> TYPE: PRT
<213> ORGANISM: SARS-CoV-2

<400> SEQUENCE: 9

Gly Ser Ala Gly
1

<210> SEQ ID NO 10

<400> SEQUENCE: 10

000

<210> SEQ ID NO 11

<400> SEQUENCE: 11

000

<210> SEQ ID NO 12

<400> SEQUENCE: 12

000

<210> SEQ ID NO 13

<400> SEQUENCE: 13

000

<210> SEQ ID NO 14

<400> SEQUENCE: 14

000

<210> SEQ ID NO 15

<400> SEQUENCE: 15

000

<210> SEQ ID NO 16

<400> SEQUENCE: 16

000

<210> SEQ ID NO 17

<400> SEQUENCE: 17

000

<210> SEQ ID NO 18

<400> SEQUENCE: 18

000

<210> SEQ ID NO 19

<400> SEQUENCE: 19

000

<210> SEQ ID NO 20

<400> SEQUENCE: 20

000

<210> SEQ ID NO 21

<400> SEQUENCE: 21

000

<210> SEQ ID NO 22

<400> SEQUENCE: 22

000

<210> SEQ ID NO 23

<400> SEQUENCE: 23

000

<210> SEQ ID NO 24

<400> SEQUENCE: 24

000

<210> SEQ ID NO 25

<400> SEQUENCE: 25

000

<210> SEQ ID NO 26

<400> SEQUENCE: 26

000

```
<210> SEQ ID NO 27
<400> SEQUENCE: 27
000

<210> SEQ ID NO 28
<400> SEQUENCE: 28
000

<210> SEQ ID NO 29
<400> SEQUENCE: 29
000

<210> SEQ ID NO 30
<400> SEQUENCE: 30
000

<210> SEQ ID NO 31
<400> SEQUENCE: 31
000

<210> SEQ ID NO 32
<400> SEQUENCE: 32
000

<210> SEQ ID NO 33
<400> SEQUENCE: 33
000

<210> SEQ ID NO 34
<400> SEQUENCE: 34
000

<210> SEQ ID NO 35
<400> SEQUENCE: 35
000

<210> SEQ ID NO 36
<400> SEQUENCE: 36
000

<210> SEQ ID NO 37
<400> SEQUENCE: 37
000
```

<210> SEQ ID NO 38

<400> SEQUENCE: 38

000

<210> SEQ ID NO 39

<400> SEQUENCE: 39

000

<210> SEQ ID NO 40

<400> SEQUENCE: 40

000

<210> SEQ ID NO 41
<211> LENGTH: 13
<212> TYPE: PRT
<213> ORGANISM: Artificial Sequence
<220> FEATURE:
<223> OTHER INFORMATION: Polypeptide

<400> SEQUENCE: 41

Thr Glu Ser Ile Val Arg Phe Pro Asn Ile Thr Asn Leu
1               5                   10

<210> SEQ ID NO 42
<211> LENGTH: 16
<212> TYPE: PRT
<213> ORGANISM: Artificial Sequence
<220> FEATURE:
<223> OTHER INFORMATION: Polypeptide

<400> SEQUENCE: 42

Asn Ile Thr Asn Leu Cys Pro Phe Gly Glu Val Phe Asn Ala Thr Arg
1               5                   10                  15

<210> SEQ ID NO 43
<211> LENGTH: 11
<212> TYPE: PRT
<213> ORGANISM: Artificial Sequence
<220> FEATURE:
<223> OTHER INFORMATION: Polypeptide

<400> SEQUENCE: 43

Leu Tyr Asn Ser Ala Ser Phe Ser Thr Phe Lys
1               5                   10

<210> SEQ ID NO 44
<211> LENGTH: 10
<212> TYPE: PRT
<213> ORGANISM: Artificial Sequence
<220> FEATURE:
<223> OTHER INFORMATION: Polypeptide

<400> SEQUENCE: 44

Leu Asp Ser Lys Val Gly Gly Asn Tyr Asn
1               5                   10

<210> SEQ ID NO 45
<211> LENGTH: 13
<212> TYPE: PRT
<213> ORGANISM: Artificial Sequence
<220> FEATURE:
<223> OTHER INFORMATION: Polypeptide

<400> SEQUENCE: 45

Lys Ser Asn Leu Lys Pro Phe Glu Arg Asp Ile Ser Thr
1               5                   10

<210> SEQ ID NO 46
<211> LENGTH: 15
<212> TYPE: PRT
<213> ORGANISM: Artificial Sequence
<220> FEATURE:
<223> OTHER INFORMATION: Polypeptide

<400> SEQUENCE: 46

Lys Pro Phe Glu Arg Asp Ile Ser Thr Glu Ile Tyr Gln Ala Gly
1               5                   10                  15

<210> SEQ ID NO 47
<211> LENGTH: 13
<212> TYPE: PRT
<213> ORGANISM: Artificial Sequence
<220> FEATURE:
<223> OTHER INFORMATION: Polypeptide

<400> SEQUENCE: 47

Gly Pro Lys Lys Ser Thr Asn Leu Val Lys Asn Lys Cys
1               5                   10

<210> SEQ ID NO 48
<211> LENGTH: 14
<212> TYPE: PRT
<213> ORGANISM: Artificial Sequence
<220> FEATURE:
<223> OTHER INFORMATION: Polypeptide

<400> SEQUENCE: 48

Asn Cys Asp Val Val Ile Gly Ile Val Asn Asn Thr Val Tyr
1               5                   10

<210> SEQ ID NO 49
<211> LENGTH: 19
<212> TYPE: PRT
<213> ORGANISM: Artificial Sequence
<220> FEATURE:
<223> OTHER INFORMATION: Polypeptide

<400> SEQUENCE: 49

Pro Glu Leu Asp Ser Phe Lys Glu Glu Leu Asp Lys Tyr Phe Lys Asn
1               5                   10                  15

His Thr Ser

<210> SEQ ID NO 50
<211> LENGTH: 14
<212> TYPE: PRT
<213> ORGANISM: Artificial Sequence
<220> FEATURE:
<223> OTHER INFORMATION: Polypeptide

<400> SEQUENCE: 50

Val Asn Ile Gln Lys Glu Ile Asp Arg Leu Asn Glu Val Ala
1               5                   10

<210> SEQ ID NO 51
<211> LENGTH: 10
<212> TYPE: PRT
<213> ORGANISM: Artificial Sequence
<220> FEATURE:

-continued

```
<223> OTHER INFORMATION: Polypeptide

<400> SEQUENCE: 51

Asn Leu Asn Glu Ser Leu Ile Asp Leu Gln
1               5                   10

<210> SEQ ID NO 52
<211> LENGTH: 11
<212> TYPE: PRT
<213> ORGANISM: Artificial Sequence
<220> FEATURE:
<223> OTHER INFORMATION: Polypeptide

<400> SEQUENCE: 52

Leu Gly Lys Tyr Glu Gln Tyr Ile Lys Trp Pro
1               5                   10
```

We claim:

1. An immunogen, comprising a glycoengineered coronavirus spike protein comprising a plurality of truncated N-glycans, and one or more unmodified O-glycans, wherein the glycoengineered coronavirus spike protein consists of the amino acid sequence of SEQ ID NO: 2.

2. The immunogen of claim 1, wherein the plurality of truncated N-glycans are monosaccharides.

3. The immunogen of claim 2, wherein the monosaccharidesare are N-acetylglucosamines (GlcNAc).

4. The immunogen of claim 1, wherein the plurality of truncated N-glycans are located in the receptor-binding domain (RBD), thereby exposing a plurality of highly conserved epitopes having amino acid sequences of TESIVRFPNITNL (SEQ ID NO: 41), NITNLCPFGEVFNATR (SEQ ID NO: 42), LYNSASFSTFK (SEQ ID NO: 43), LDSKVGGNYN (SEQ ID NO: 44), KSNLKPFERDIST (SEQ ID NO: 45), KPFERDISTEIYQAG (SEQ ID NO: 46) and/or GPKKSTNLVKNKC (SEQ ID NO: 47).

5. The immunogen of claim 1, wherein the plurality of truncated N-glycans are located in the heptad repeat 2 (HR2) domain, thereby exposing a plurality of highly conserved epitopes having amino acid sequences of NCDVVIGIVNNTVY (SEQ ID NO: 48), PELDSFKEELDKYFKNHTS (SEQ ID NO: 49), VNIQKEIDRLNEVA (SEQ ID NO: 50), and/or NLNESLIDLQ (SEQ ID NO: 51).

6. The immunogen of claim 1, wherein the glycoengineered coronavirus spike protein is derived from a native coronavirus spike protein by glycoengineering in vitro.

7. The immunogen of claim 6, wherein the native coronavirus spike protein is the spike protein of severe acute respiratory syndrome coronavirus 2 (SAR-CoV-2) or a variant thereof.

8. The immunogen of claim 7, wherein the variant is selected from the group consisting of D614G, Alpha (B.1.1.7 and Q lineages), Beta (B.1.351 and descendent lineages), Gamma (P.1 and descendent lineages), Epsilon (B.1.427 and B.1.429), Eta (B.1.525), Iota (B.1.526), Kappa (B.1.617.1), 1.617.3, Mu (B.1.621, B.1.621.1), Zeta (P.2), Delta (B.1.617.2 and AY lineages) and Omicron (B.1.1.529 and BA lineages).

9. The immunogen of claim 1, wherein the glycoengineered coronavirus spike protein generated using endoglycosidase H (Endo H) is present as a trimer and retained the same tertiary structure as the native coronavirus spike protein and is capable of eliciting an enhanced immune response relative to the native coronavirus spike protein.

10. The immunogen of claim 9, wherein the enhanced immune response is an increased IgG titer, an increased IgM titer, an increased neutralization titer, an increased CD4 T cell response, an increased CD8 T cell response, or a combination thereof.

11. The immunogen of claim 1, wherein the glycoengineered coronavirus spike protein consists of a polypeptide consisting of 21 truncated N-glycans, each having a GlcNAc moiety.

12. An immunogenic composition, comprising: (a) the immunogen of claim 1, and (b) optionally, an adjuvant.

13. The immunogenic composition of claim 12, wherein the adjuvant is aluminum hydroxide, aluminum phosphate, incomplete Freund's adjuvant (IFA), squalene, Alum, Alhydrogel, MF59, QS-21, CpG 1018, AS03, AS37, Matrix-M or a combination thereof.

14. The immunogenic composition of claim 12, wherein the immunogenic composition is an improved coronavirus vaccine capable of eliciting an enhanced immune response relative to a vaccine using a native coronavirus spike protein.

15. The immunogenic composition of claim 14, wherein the coronavirus is SAR-CoV-2 or a variant thereof.

16. A method for eliciting an immune response against a severe acute respiratory syndrome coronavirus 2 (SARS-CoV-2) in a subject in need thereof, comprising administering to the subject an effective amount of an immunogenic composition of claim 12.

17. The method of claim 16, wherein the immune response comprises production of neutralizing antibodies against SARS-CoV-2 or a variant thereof.

18. The method of claim 17, wherein the variant is selected from the group consisting of D614G, Alpha (B.1.1.7 and Q lineages), Beta (B.1.351 and descendent lineages), Gamma (P.1 and descendent lineages), Epsilon (B.1.427 and B.1.429), Eta (B.1.525), Iota (B.1.526), Kappa (B.1.617.1), 1.617.3, Mu (B.1.621, B.1.621.1), Zeta (P.2), Delta (B.1.617.2 and AY lineages) and Omicron (B.1.1.529 and BA lineages).

19. A method for protecting a subject in need thereof from infection with SARS-CoV-2 or a variant thereof or preventing a subject in need thereof from contracting COVID-19 disease, the method comprising administering to the subject in need thereof an effective amount of the immunogenic composition of claim 12.

* * * * *